(12) United States Patent
Adelman et al.

(10) Patent No.: US 8,580,814 B2
(45) Date of Patent: *Nov. 12, 2013

(54) METHODS OF USING (+)-1,4-DIHYDRO-7-[(3S,4S)-3-METHOXY-4-(METHYLAMINO)-1-PYRROLIDINYL]-4-OXO-1-(2-THIAZOLYL)-1,8-NAPHTHYRIDINE-3-CARBOXYLIC ACID FOR TREATMENT OF CANCER

(75) Inventors: Daniel C. Adelman, Redwood City, CA (US); Jeffrey A. Silverman, Burlingame, CA (US)

(73) Assignee: Sunesis Pharmaceuticals, Inc., South San Francisco, CA (US)

(*) Notice: Subject to any disclaimer, the term of this patent is extended or adjusted under 35 U.S.C. 154(b) by 201 days.

This patent is subject to a terminal disclaimer.

(21) Appl. No.: 11/991,349

(22) PCT Filed: Sep. 5, 2006

(86) PCT No.: PCT/US2006/034699
§ 371 (c)(1),
(2), (4) Date: Jun. 18, 2009

(87) PCT Pub. No.: WO2007/028171
PCT Pub. Date: Mar. 8, 2007

(65) Prior Publication Data
US 2009/0263393 A1    Oct. 22, 2009

Related U.S. Application Data

(60) Provisional application No. 60/789,093, filed on Apr. 3, 2006, provisional application No. 60/788,927, filed on Apr. 3, 2006, provisional application No. 60/810,285, filed on Jun. 1, 2006.

(51) Int. Cl.
*A61K 31/4375* (2006.01)
*C07D 461/00* (2006.01)

(52) U.S. Cl.
USPC .......... 514/300; 514/299; 514/279; 514/277; 546/123; 546/122; 546/113; 546/112; 546/26

(58) Field of Classification Search
None
See application file for complete search history.

(56) References Cited

U.S. PATENT DOCUMENTS

| | | |
|---|---|---|
| 4,261,989 A | 4/1981 | Sasaki et al. |
| 4,810,643 A | 3/1989 | Souza |
| 4,999,291 A | 3/1991 | Souza |
| 5,078,966 A | 1/1992 | Strong et al. |
| 5,134,127 A | 7/1992 | Stella et al. |
| 5,229,496 A | 7/1993 | Deeley et al. |
| 5,391,485 A | 2/1995 | Deeley et al. |
| 5,393,870 A | 2/1995 | Deeley et al. |
| 5,489,519 A * | 2/1996 | Deeley et al. ............. 435/69.1 |
| 5,528,823 A | 6/1996 | Rudy, Jr. et al. |
| 5,580,755 A | 12/1996 | Souza |
| 5,817,669 A | 10/1998 | Tomita et al. |
| 6,171,857 B1 | 1/2001 | Hendrickson |
| 6,291,643 B1 | 9/2001 | Zou et al. |
| 6,570,002 B1 | 5/2003 | Hardwick et al. |
| 6,641,810 B2 | 11/2003 | Gold |
| 6,641,833 B2 * | 11/2003 | Dang ............................. 424/426 |
| 6,670,144 B1 | 12/2003 | Craig et al. |
| 6,696,483 B2 | 2/2004 | Singh |
| 6,723,734 B2 | 4/2004 | Kim et al. |
| 7,211,562 B2 | 5/2007 | Rosen et al. |
| 7,989,468 B2 * | 8/2011 | Adelman et al. .............. 514/300 |
| 2003/0165887 A1 | 9/2003 | Reed |
| 2003/0216316 A1 | 11/2003 | Haran-Ghera et al. |
| 2003/0232334 A1 * | 12/2003 | Morris et al. ...................... 435/6 |
| 2004/0106605 A1 * | 6/2004 | Carboni et al. ............. 514/226.8 |
| 2004/0132825 A1 * | 7/2004 | Bacopoulos et al. ......... 514/575 |
| 2005/0203120 A1 | 9/2005 | Adelman et al. |
| 2005/0215583 A1 | 9/2005 | Arkin et al. |
| 2006/0025437 A1 | 2/2006 | Adelman et al. |
| 2006/0063795 A1 | 3/2006 | Arkin et al. |
| 2006/0247267 A1 | 11/2006 | Adelman et al. |
| 2008/0063642 A1 | 3/2008 | Adelman et al. |

FOREIGN PATENT DOCUMENTS

| | | |
|---|---|---|
| JP | 09-221424 | 8/1997 |
| JP | 11-349565 | 12/1999 |
| WO | WO98/30902 | 7/1998 |
| WO | WO01/74395 | 10/2001 |
| WO | WO02/20500 | 3/2002 |
| WO | WO2004/085418 | 10/2004 |
| WO | WO2007/028171 | 3/2007 |
| WO | WO2007/146335 | 12/2007 |
| WO | WO2008/016678 | 2/2008 |
| WO | WO2009/054935 | 4/2009 |
| WO | WO2009/075841 | 6/2009 |

OTHER PUBLICATIONS

"Harrison's Principles of Internal Medicine," 15th Ed., by Braunwald et al. (Eds.), McGraw-Hill (New York), pp. 706-727 (2001).*
"Treatment of platinum-resistant ovarian cancer" by Trimble et al., Expert Opin. Pharmacother. 2, 1299-306 (2001).*
Allen, J.C., Database MEDLINE Accession No. 92345081, "Complications of Chemotherapy in Patients with Brain and Spinal Cord Tumors", Ped. Neurosurg., vol. 17, No. 4, pp. 218-224, 1991-1992.
Chiba, et al., "Practical Synthesis of AG-7352, Optically Active New Antitumor Agent." Abstract, 218th ACS National Meeting, Aug. 22-26, 1999.
Cleton, F.J., "History of the Development of Anticancer Drugs", Oxford Textbook of Oncology, vol. 1. pp. 445-453, 1995.
Emens, et al., Curr. Opinion Mol. Ther. 3(1):77-84, 2001.
Evanchik, et al., "Non-Clinical Admet, PK, and Biological Activity of SNS-595, a Novel Cell Cycle Inhibitory Antineoplastic Agent." Drug metabolism reviews, Marcel Dekker,New York, NY, US, vol. 36, No. SUPPL1, Aug. 2004 (2004-2008), p. 103.

(Continued)

Primary Examiner — Brandon Fetterolf
Assistant Examiner — Theodore R West
(74) Attorney, Agent, or Firm — Jones Day

(57) ABSTRACT

Methods of treating, preventing or managing cancer, including certain leukemias are disclosed. The methods encompass the administration of enantiomerically pure (+)-1,4-dihydro-7-[(3S,4S)-3-methoxy-4-(methylamino)-1-pyrrolidinyl]-4-oxo-1-(2-thiazolyl)-1,8-naphthyridine-3-carboxylic acid. Also provided are methods of treatment using this compound with chemotherapy, radiation therapy, hormonal therapy, biological therapy or immunotherapy. Pharmaceutical compositions and single unit dosage forms suitable for use in the methods are also disclosed.

24 Claims, 20 Drawing Sheets

(56) References Cited

OTHER PUBLICATIONS

Freireich, et al., "Quantitative Comparison of Toxicity of Anticancer Agents in Mouse, Rat, Hamster, Dog, Monkey, and Man", Cancer Chemotherapy Reports, vol. 50, No. 4, pp. 219-244, May 1966.

Glaspy, et al., Database CANCER LIT Accession No. 2002-047630, "A dose-Finding and Safety Study of Novel Erythropoiesis Stimulating Protein (NESP) for the Treatment of Anaemia in Patients Receiving Multicycle Chemotherapy", Br. J. Cancer, vol. 84 (Suppl. 1), pp. 17-23, Apr. 2001.

Goodman & Gilman, The Pharmacological Basis of Therapeutics, McGraw-Hill Medical Publishing Division, Tenth Edition, pp. 1404-1411 (2001).

Herman, et al., Database MEDLINE Accession No: 78104303, "Nabilone: A Potent Antiemetic cannabinol with Minimal Euphoria", Biomedicine. Vo. 27, No. 9-10, pp. 331-334, Dec. 1977.

Jacobs, Leonard S., "National Medical Series for Independent Study: Pharmacology", Fourth Edition, Chapter 11, pp. 253-274, 1996.

Kashimoto, et al., Database BIOSIS Accession No. 2001:366681, "Antitumor Activity of a Novel Quinolone Analog AG-7352 in Human Xenograft Models of Leukemia or Drug-Resistant Tumors and in an Experimental Metastatic Tumor Model", Proc. Am. Assoc. Can. Res. An. Mtg., vol. 42, p. 102, Mar. 2001.

Lawrence, et al., "SNS-595, a Novel S-Phase Active Cytotoxic, Demonstrates Pharmacologic Properties Appropriate for the Treatment of Advanced Hematologic Malignancies." Blood, vol. 106, No. 11, Part 2, Nov. 2005, p. 2378.

Lawrence, et al., "SNS-595, a Novel S-Phase Active Cytotoxic, Exhibits Potent In Vitro and In Vivo Activities, and Has the Potential for Treating Advanced Hematoloic Malignacies." Proceedings of the Annual Meeting of the American Association for Cancer Research, New York, NY, vol. 47, Apr. 2006, p. 1110.

Ledwidge, et al., "Effects of surface active characteristics and solid state forms on the pH solubility profiles of drug-salt systems," International Journal of Pharmaceutics 174 (1998) 187-200.

The Merck Manual (1999), pp. 973-995.

Nakano, et al., "Antitumor Activity of a Novel Quinolone DNA Topoisomerase II Inhibitor AG-7352." Proceedings of the Annual Meeting of the American Association for Cancer Research, New York, NY, vol. 40, Mar. 1999, p. 115—Abstract 767. XP008073720.

Page, Do. Ph.D., "Principles of chemotherapy", Cancer Management: A Multidisciplinary Approach, pp. 21-28.

Penichet, et al., "Antibody-cytokine fusion proteins for the therapy of cancer," J. Immunol. Methods 248:91-101, 2001.

Ryffel, B., Database CANCER LIT Accession No. 97254190, "Safety of Human Recombinant Proteins", Biomed. Environ. Sci. vol. 190, No. 1, pp. 65-72, Mar. 1997.

Sato, et al., "In Vivo Antitumor Activity of a Novel Quinolone Analogue AG-7352 Against a Borad-Spectrum of Cancers and Drug-Resistant Human Cancers." Abstract, 11th NCI-EOARTC-AACR symposium on new drugs in cancer therapy, Nov. 7-10, 2000.

Therasse, et al., "New Guidelines to Evaluate the Response to Treatment in Solid Tumors", Journal of the National Cancer Institute, Vo. 92, No. 3, Feb. 2, 2000.

Thirion, et al., "Interest of investigating p53 status in breast cancer by four different methods." Oncology Reports, vol. 9, No. 6, Nov. 2002, pp. 1167-1172.

Tolcher, et al., "Phase I and Pharmacokinetic Study of NSC 655649, a Rebeccamycin Analog with Topoisomerase Inhibitory Properties", Journal of Clinical Oncology, vol. 19, pp. 2937-2947, No. 11, Jun. 1, 2001.

Tomita, Synthesis and Structure-Activity Relationships of Novel 7-Substituted 1.4-Dihydro-4-oxo-1-(2-thiazolyl)-1,8-naphthyridine-3-carboxylic Acids as Antitumor Agents, Part 1, J.Med.Chem. 2002, vol. 45, pp. 5564-5575, 2002.

Tomita, et al., Database CAPLUS Accession No. 1999:92763, "Synthesis and Antitumor activity of Novel 7-Substituted 1, 4-dihydro-4-oxo-1-2(2-thiazolyl)-1,8-naphthyridine-3-carobxylic Acids", BK Abstracts, 217th ACS Nat Mtd., Mar. 21-25, 1999.

Tsuzuki, et al., "Practical Synthesis of (3S,4S)-3-Methoxy-4-Methylaminopyrrolidine." Tetrahedron: Asymmetry 12(2001) 2989-2997.

Tsuzuki, et al., "Process Research of a Novel Quinolone Antitumor Agent, AG-7352." English Abstract, The Japanese Society for Process Chemstry, 2004 Summer Symposium.

Tsuzuki, et al., "Synthesis and Structure—Activity Relationships of 3-Substitued 1, 4-Dihydro-4-Oxo-1-(2-Thiazolyl)-1, 8-Naphthridines as Novel Antitumor Agents." Bioorganic & Medicinal Chemistry Letters 14 (2004): 3189-3193.

Tsuzuki, et al., "Synthesis of Optically Active Amine at C-7 Position of New Antitumor Agent AG-7352." Abstract, Molecular Chirality Conference, 1999.

Tsuzuki, et al., "Efficient stereospecific synthesis of (S,S)-3-methozy-4-methylaminopyrrolidine", Tetrahedron: Asymmetry, vol. 12, pp. 1793-1799, 2001.

Tsuzuki, et al., Synthesis and Structure-Activity Relationships of Novel 7-Substituted 1,4-Dihydro-4-oxo-1-(2-thiazolyl)-1,8-naphthyridine-3-carboxylic Acids as Antitumor Agents, Part 2, vol. 47, pp. 2097-2109, 2004.

Wright, et al., "SNS-595 Has Synergistic Activity in Vitro with DNA Damaging Agents and Antimetabolites." Proceedings of the Annual Meeting of the American Association for Cancer Research, New York, NY, vol. 47, Apr. 2006, p. 504. XP001199686.

U.S.P.T.O. non-Final Office Action dated Jul. 18, 2007 for U.S. Appl. No. 11/080,283, filed Mar. 14, 2005.

U.S.P.T.O. non-Final Office Action dated Mar. 24, 2008 for U.S. Appl. No. 11/080,283, filed Mar. 14, 2005.

U.S.P.T.O. Final Office Action dated Dec. 31, 2008 for U.S. Appl. No. 11/080,283, filed Mar. 14, 2005.

U.S.P.T.O. Restriction Requirement dated Jul. 18, 2007 for U.S. Appl. No. 11/080,102, filed Mar. 14, 2005.

U.S.P.T.O. non-Final Office Action dated Nov. 7, 2007 for U.S. Appl. No. 11/080,102, filed Mar. 14, 2005.

U.S.P.T.O.non-Office Action dated Mar. 5, 2008 for U.S. Appl. No. 11/080,102, filed Mar. 14, 2005.

U.S.P.T.O. Final Office Action dated Nov. 17, 2008 for U.S. Appl. No. 11/080,102, filed Mar. 14, 2005.

U.S.P.T.O. non-Final Office Action dated Jun. 26, 2009 for U.S. Appl. No. 11/080,102, filed Mar. 14, 2005.

Lancet et al., (2011), Leukemia, p. nos. 1-7.

Stuart et al., American Society of Clinical Oncology (ASCO) Annual Meeting,, Jun. 2010.

Hirte et al., American Society of Clinical Oncology (ASCO) Annual Meeting,, Jun. 2010.

U.S.P.T.O. Final Office Action dated Dec. 18, 2009 for U.S. Appl. No. 11/080,283, filed Mar. 14, 2005.

U.S.P.T.O. Notice of Panel Decision from Pre-Appeal Brief Review dated May 18, 2010 for U.S. Appl. No. 11/080,283, filed Mar. 14, 2005.

U.S.P.T.O. Examiner's Answer dated Feb. 1, 2011 for U.S. Appl. No. 11/080,283, filed Mar. 14, 2005.

U.S.P.T.O. Notice of Allowance and Fees Due dated Jun. 1, 2011 for U.S. Appl. No. 11/080,283, filed Mar. 14, 2005.

U.S.P.T.O. Final Office Action dated Feb. 23, 2010 for U.S. Appl. No. 11/080,102, filed Mar. 14, 2005.

U.S.P.T.O. Notice of Allowance and Fees Due dated Mar. 14, 2011 for U.S. Appl. No. 11/080,102, filed Mar. 14, 2005.

U.S.P.T.O. Restriction Requirement dated Apr. 16, 2010 for U.S. Appl. No. 11/890,196, filed Aug. 2, 2007.

U.S.P.T.O. non-Final Office Action dated Nov. 19, 2010 for U.S. Appl. No. 11/890,196, filed Aug. 2, 2007.

U.S.P.T.O. Final Office Action dated Jul. 13, 2011 for U.S. Appl. No. 11/890,196, filed Aug. 2, 2007.

U.S.P.T.O. Restriction Requirement dated Mar. 3, 2011 for U.S. Appl. No. 12/747,167, filed Sep. 9, 2010.

* cited by examiner 20 mg/kg SNS-595
Day 12

METHODS OF USING (+)-1,4-DIHYDRO-7-[(3S,4S)-3-METHOXY-4-(METHYLAMINO)-1-PYRROLIDINYL]-4-OXO-1-(2-THIAZOLYL)-1,8-NAPHTHYRIDINE-3-CARBOXYLIC ACID FOR TREATMENT OF CANCER

This application is a §371 of PCT/US2006/034699, filed Sep. 5, 2006, which claims benefit under 35 U.S.C. 119(e) of U.S. patent application Ser. No. 11/218,387, filed Sep. 2, 2005, now converted to U.S. Provisional Patent Application No. 60/921,500, U.S. patent application Ser. No. 11/218,653, filed Sep. 2, 2005, now converted to U.S. Provisional Patent Application No. 60/921,501, and U.S. Provisional Patent Application Nos. 60/789,093, filed Apr. 3, 2006; 60/788,927, filed Apr. 3, 2006 and 60/810,285, filed Jun. 1, 2006, which are incorporated by reference herein in their entireties.

1. FIELD

Provided herein are methods for treating, preventing or managing cancer, including specific leukemias by administering enantiomerically pure (+)-1,4-dihydro-7-[(3S,4S)-3-methoxy-4-(methylamino)-1-pyrrolidinyl]-4-oxo-1-(2-thiazolyl)-1,8-naphthyridine-3-carboxylic acid, which is also known as SNS-595 or AG-7352. Also provided are doses, dosing regimens and dosages for SNS-595 and its administration.

2. BACKGROUND

SNS-595 is chemically named (+)-1,4-dihydro-7-[(3S,4S)-3-methoxy-4-(methylamino)-1-pyrrolidinyl]-4-oxo-1-(2-thiazolyl)-1,8-naphthyridine-3-carboxylic acid, and has the following structure:

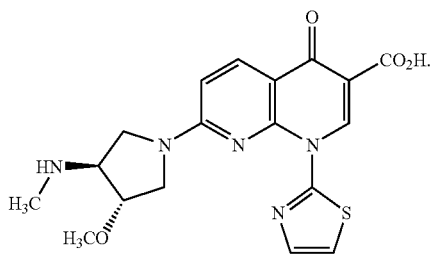 [SMILES: CN[C@H]1CN(c2ccc3c(=O)c(C(=O)O)cn(-c4nccs4)c3n2)C[C@@H]1OC]

SNS-595 is known for its anti-tumor activity. Treatment of the following cancers with SNS-595 has been proposed in the literature: bladder cancer, breast cancer, cervical cancer, colon cancer, esophageal cancer, head and neck cancer, liver cancer, lung cancer, melanoma, myeloma, neuroblastoma (i.e., CNS cancer), ovarian cancer, pancreatic cancer, prostate cancer, renal cancer, sarcoma, skin cancer, stomach cancer, testicular cancer, thyroid cancer and uterine cancer. Various dosing regimens have been reported, for example, see, U.S. Patent Application Pub. Nos. 2005-0203120; 2005-0215583 and 2006-0025437, all of which are incorporated herein by reference in their entirety.

There continues to be a need for safe and effective dosages and dosing regimens for administering SNS-595 in treating, preventing and managing various cancers, including leukemias.

3. SUMMARY

SNS-595 is a known cytotoxic agent with utility against various cancers. Herein are discussed novel treatment methods including the treatment of specific leukemias. In addition, described are unique dosing ranges, regimens and pharmaceutical doses.

The treatment, prevention or management of cancer using SNS-595, pharmaceutical compositions thereof and unique dosing is described. Generally, the types of cancers that can be treated, prevented or managed using methods provided herein include, but are not limited to: bladder cancer, breast cancer, cervical cancer, colon cancer (including colorectal cancer), esophageal cancer, head and neck cancer, liver cancer, lung cancer (both small cell and non-small cell), melanoma, myeloma, neuroblastoma (i.e., CNS cancer), ovarian cancer, pancreatic cancer, prostate cancer, renal cancer, sarcoma (including osteosarcoma), skin cancer (including squamous cell carcinoma), stomach cancer, testicular cancer, thyroid cancer, and uterine cancer. The cancer can be relapsed, refractory or resistant to conventional therapy.

In certain embodiments, the cancer includes hematologic malignancies, including, but not limited to leukemias, lymphomas (Non-Hodgkin's Lymphoma), Hodgkin's disease (also called Hodgkin's Lymphoma) and myeloma. The various forms of leukemias include, but are not limited to, chronic lymphocytic leukemia, chronic myeloid leukemia, acute lymphocytic leukemia, acute myelogenous leukemia and acute myeloblastic leukemia. The leukemia can be relapsed, refractory or resistant. In certain embodiments, the hematologic malignancy is promyelocytic leukemia, T-cell leukemia or lymphoblastic leukemia.

Further provided are methods of treating, preventing or managing cancer by administering SNS-595 in a certain manner. In certain embodiment, the methods comprise administering to a mammal a dose of about 1 mg/m² to 150 mg/m², about 1 mg/m² to 100 mg/m², 1 mg/m² to 75 mg/m², 15 mg/m² to 80 mg/m², or about 3 mg/m² to 24 mg/m² of SNS-595, on the basis of body surface area. In certain embodiment, the methods comprise administering to a mammal a dose of about 15 g/m², 25 g/m² or 50 mg/m² of SNS-595, on the basis of body surface area. Additional dosing and dosing regimens are described in more detail herein below.

Also provided herein are dosing and dosing regimens for solid cancers. The administered dose of SNS-595 can be delivered as a single dose such as, for example, an IV push of 10-15 minutes duration (e.g., a single bolus injection) or over time such as, for example, a 24-hour period (e.g., continuous infusion over time or divided bolus doses over time) and is repeated as necessary, for example, until the patient experiences stable disease or regression, or until the patient experiences disease progression or unacceptable toxicity.

In some embodiments, SNS-595 can be cyclically administered to a patient. Cycling therapy involves the administration of the active agent for a period of time, followed by a rest for a period of time and repeating this sequential administration. Cycling therapy can reduce the development of resistance to one or more of the therapies, avoid or reduce the side effects of one of the therapies and/or improves the efficacy of the treatment.

In another embodiment, SNS-595 is administered in combination with another drug ("second active agent") or another therapy conventionally used to treat, prevent or manage cancer, or the methods of dosing of SNS-595 described herein can be applied in combination therapy settings. Second active agents include known small molecule, anticancer, antitumor or cytotoxic agents and large molecules (e.g., proteins and antibodies), examples of which are provided herein, as well as stem cells or cord blood. Examples of such conventional therapies include, but are not limited to, surgery, chemotherapy, radiation therapy, hormonal therapy, biological therapy, immunotherapy, blood transfusions, and combinations thereof.

Thus, in certain embodiment, provided herein are combinations for treatment, prevention and management of solid tumors. In other embodiment, provided herein are combinations for treatment, prevention and management of leukemias and lymphomas.

Also provided are pharmaceutical compositions, single unit dosage forms, and dosing regimens which comprise SNS-595, and a second, or additional, active agent. Second active agents include specific combinations, or "cocktails," of drugs or therapy, or both.

4. BRIEF DESCRIPTION OF FIGURES

Figure 8:
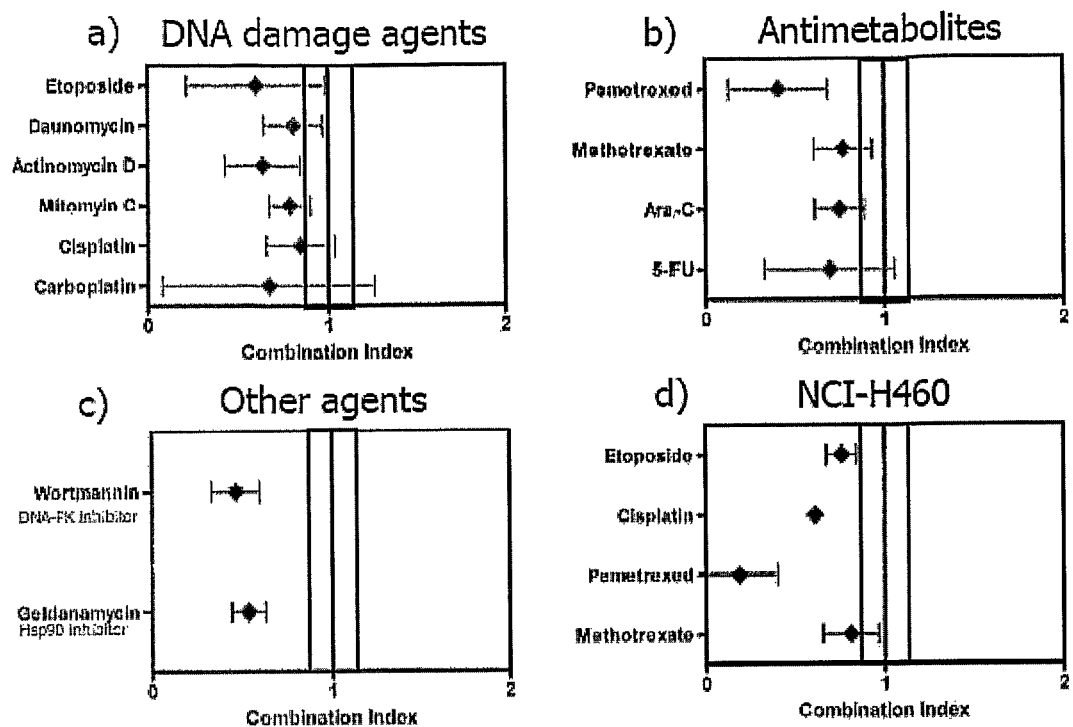
Figure 9:
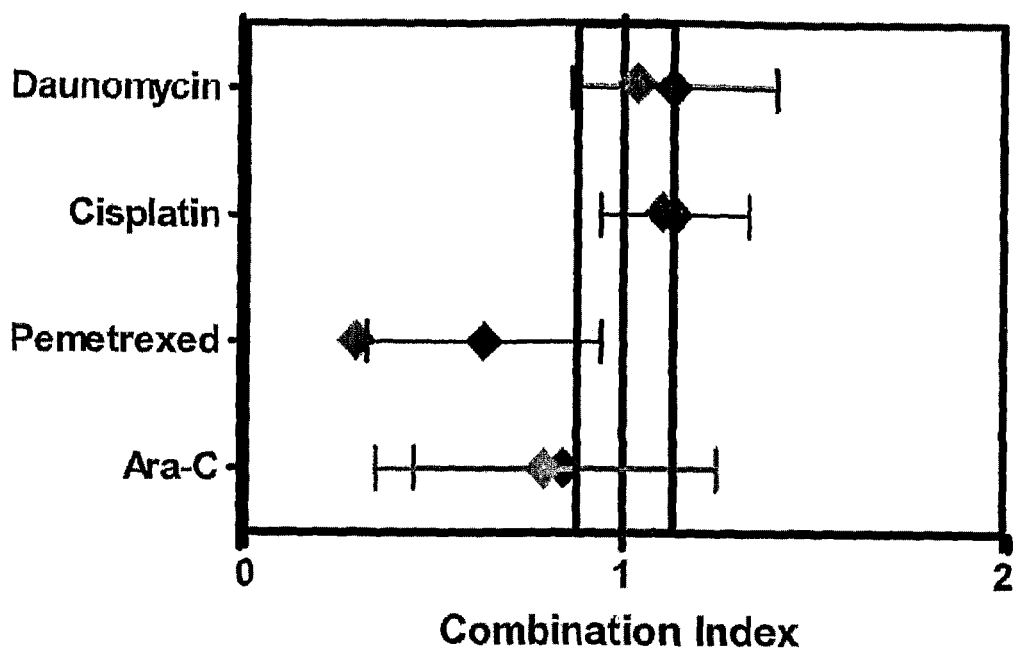
Figure 10:
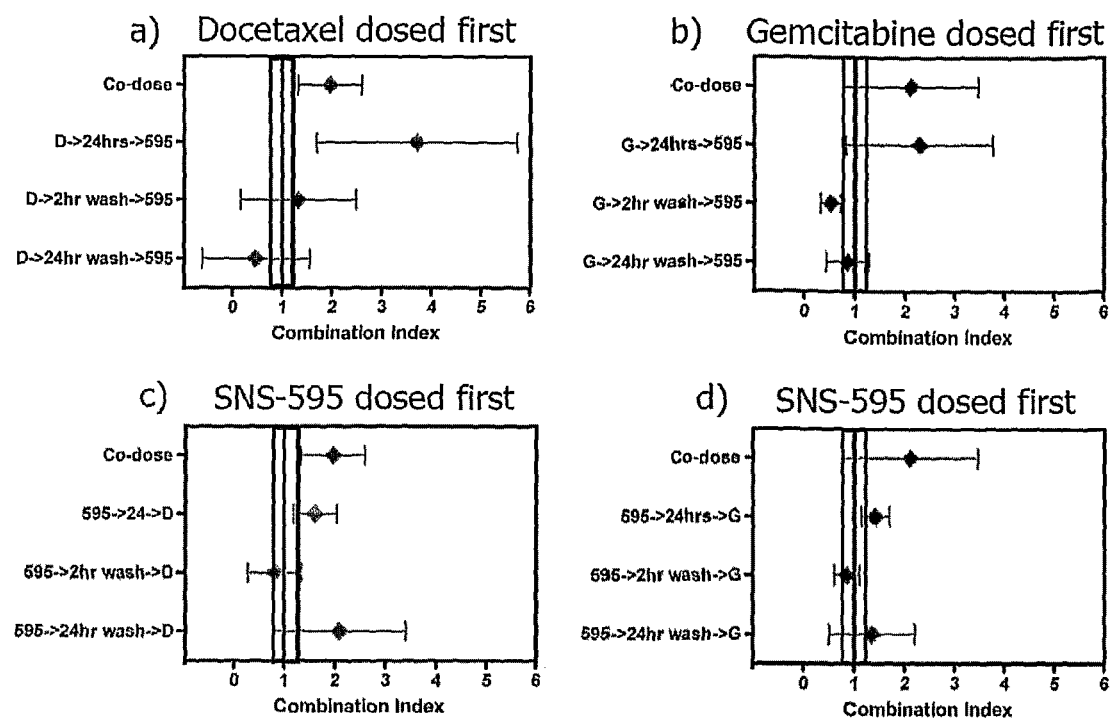

FIGS. 8a-c demonstrate synergistic/additive effect of co-dosing SNS-595 with various cytotoxic agents in HCT116 colon carcinoma cells; and FIG. 8d demonstrates synergistic/additive effect of co-dosing SNS-595 with various cytotoxic agents in H460 lung cancer cells;

FIG. 9 shows combination index when SNS-595 is dosed simultaneously with a selection of DNA damaging agents and antimetabolites in SKOV3 ovarian cancer cell line (+/+) and (−/−) for p53 expression, shown as black and grey diamonds, respectively; and FIGS. 10 a-d demonstrate effect of co-dosing SNS-595 with various cytotoxic agents in HCT 116 colon carcinoma cells.

Figure 11:
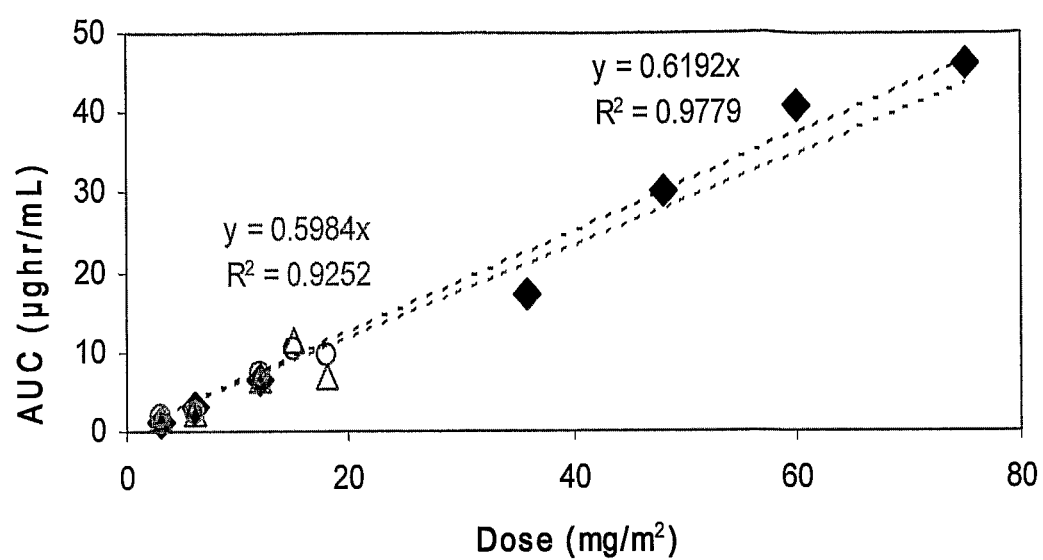

FIG. 11 provides dose linearity of three weekly doses (qwk×3; circles=week 1; triangles=week 2) and once every three week doses (q3wk; diamonds) of SNS-595 in patients with advanced solid tumors.

Figure 12:
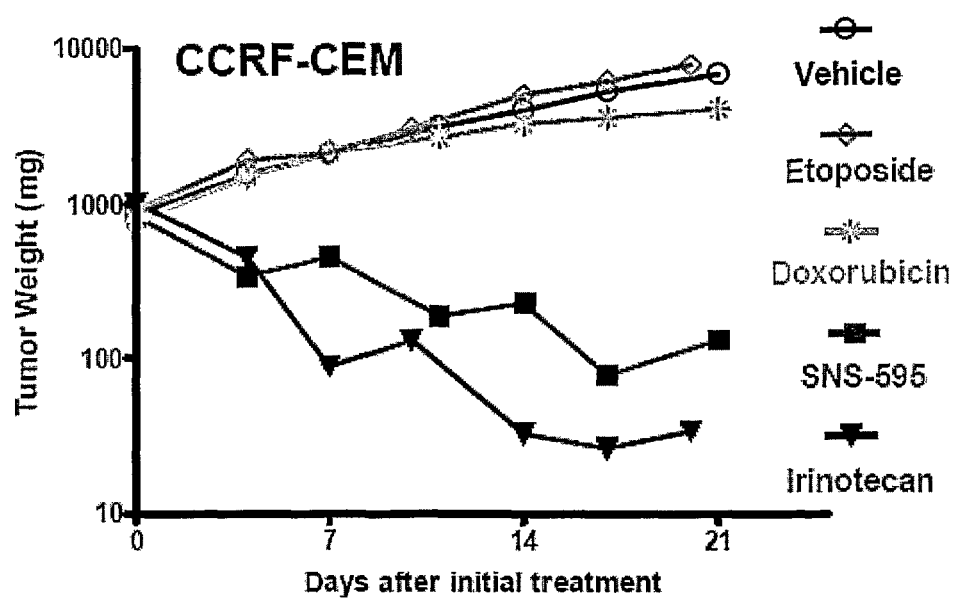

FIG. 12 provides a comparison of anti-tumor activities of SNS-595, etoposide, doxorubicin and irinotecan in CCRF-CEM xenograft model.

Figure 13:
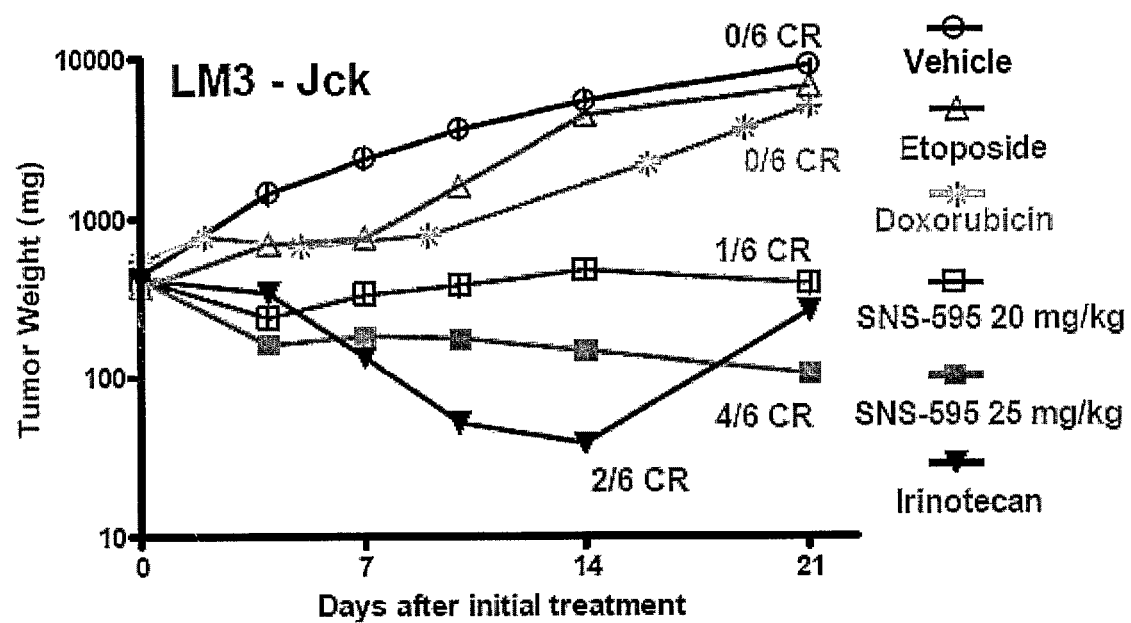

FIG. 13 provides a comparison of anti-tumor activities of SNS-595 (at 20 mg/kg and 25 mg/kg), etoposide, doxorubicin and irinotecan in LM3-Jck xenograft model.

Figure 14:
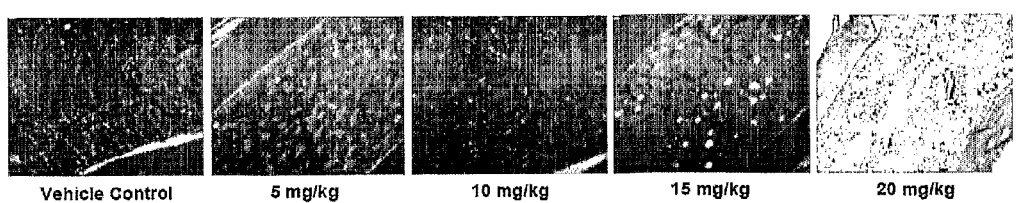
Figure 15:
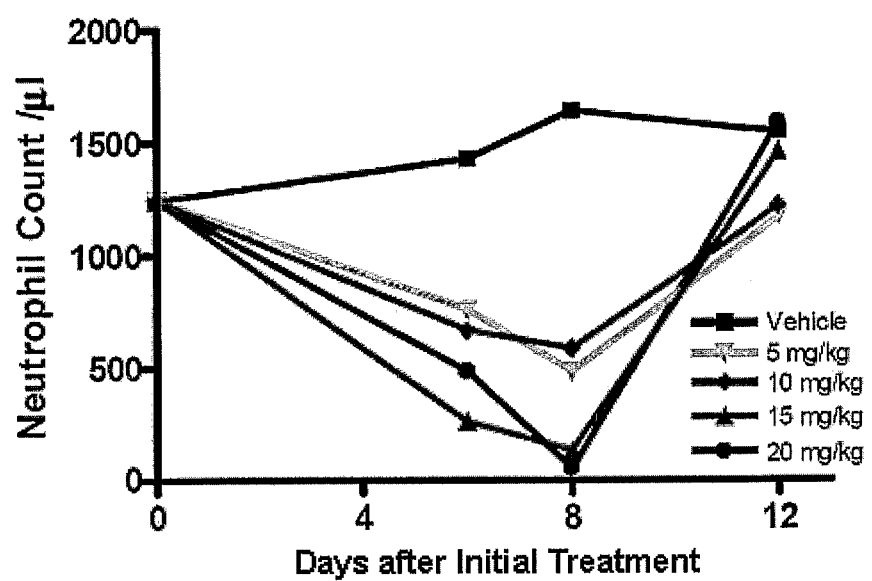
Figure 16:
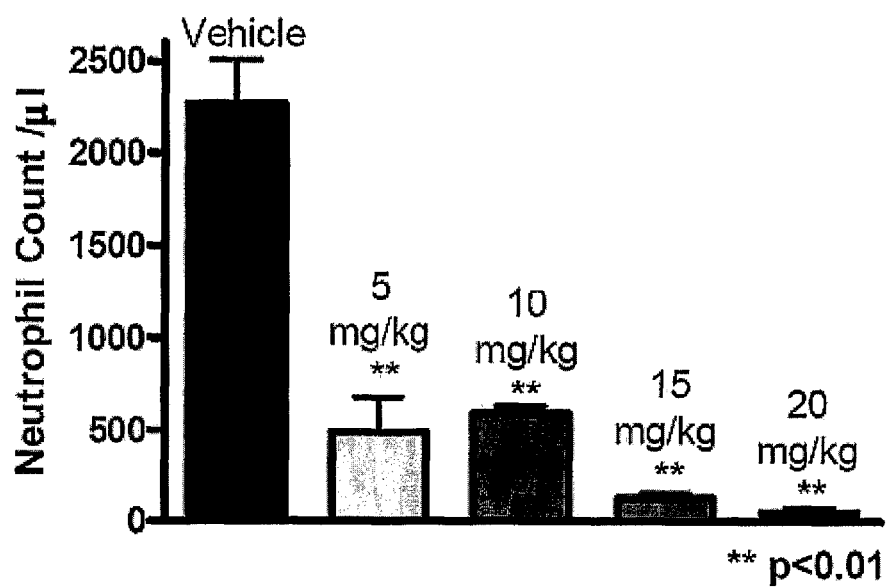
Figure 17:
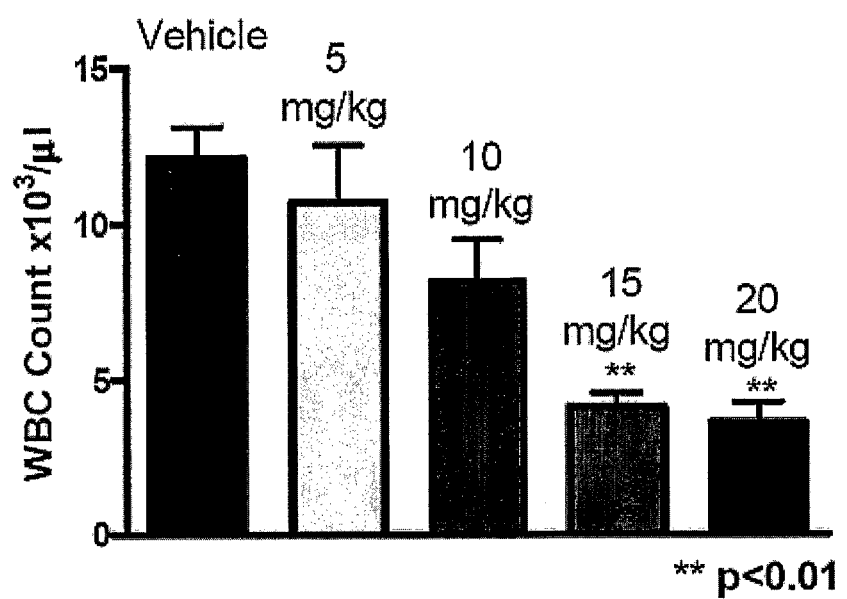
Figure 18:
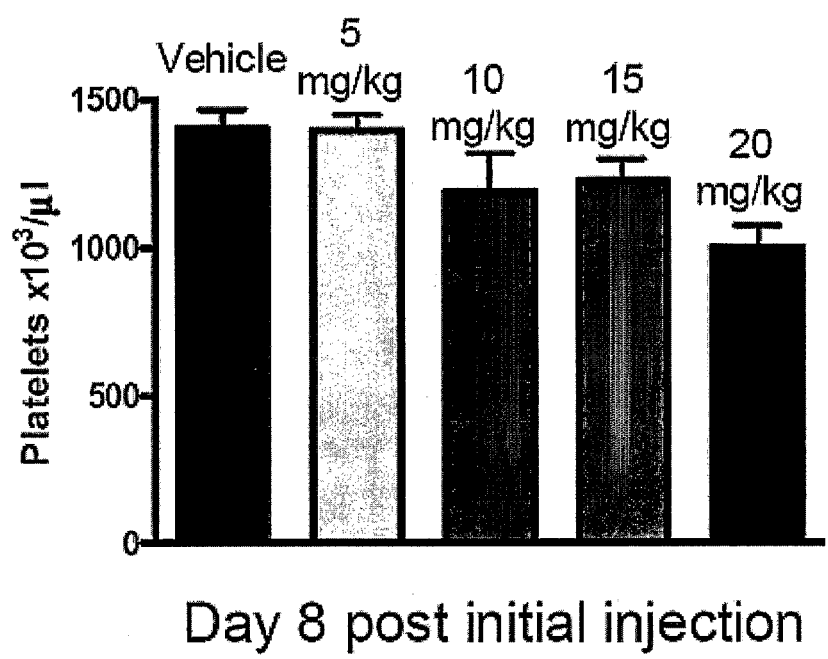
Figure 19:
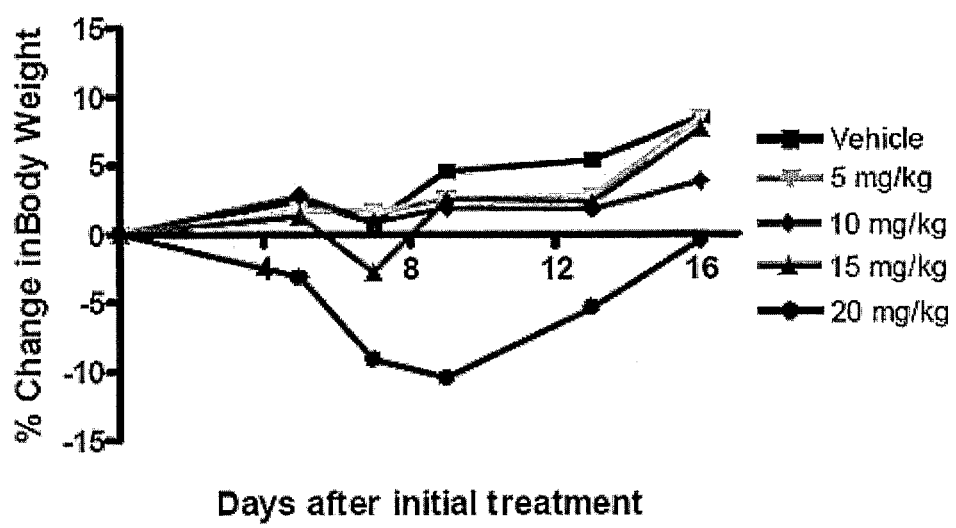
Figure 20:
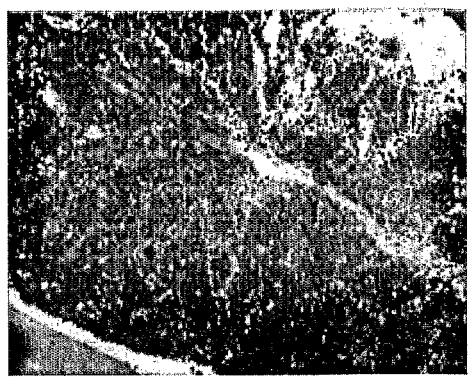

FIG. 14 shows cellularity in bone marrow 6 days post initial injection of SNS-595 in female CD-1 mice. SNS-595 was administered on day 0 and day 4. All images shown at 10× magnification;

FIG. 15 provides neutrophil response to SNS-595 dose;

FIG. 16 provides neutrophil count at various SNS-595 doses by day 8;

FIG. 17 provides WBC count at various SNS-595 doses by day 8;

FIG. 18 provides platelet count at various SNS-595 doses by day 8;

FIG. 19 provides percent change in body weight at various time intervals after administering SNS-595; and FIG. 20 shows bone marrow rebound at day 12 after administering 20 mg/kg SNS-595.

5. DEFINITIONS

Unless defined otherwise, all technical and scientific terms used herein have the same meaning as is commonly understood by one of ordinary skill in the art. All cited patents, applications, published applications and other publications are incorporated by reference in their entirety. In the event that there are a plurality of definitions for a term herein, those in this section prevail unless stated otherwise.

As used herein, enantiomerically pure (+)-1,4-dihydro-7-[(3S,4S)-3-methoxy-4-(methylamino)-1-pyrrolidinyl]-4-oxo-1-(2-thiazolyl)-1,8-naphthyridine-3-carboxylic acid is substantially free from (−)-1,4-dihydro-7-[(3S,4S)-3-methoxy-4-(methylamino)-1-pyrrolidinyl]-4-oxo-1-(2-thiazolyl)-1,8-naphthyridine-3-carboxylic acid (i.e., in enantiomeric excess). In other words, the "(+)" form of 1,4-dihydro-7-[(3S,4S)-3-methoxy-4-(methylamino)-1-pyrrolidinyl]-4-oxo-1-(2-thiazolyl)-1,8-naphthyridine-3-carboxylic acid is substantially free from the "(−)" form of the compound and is, thus, in enantiomeric excess of the "(−)" form. The term "enantiomerically pure" or "pure enantiomer" denotes that the compound comprises more than 75% by weight, more than 80% by weight, more than 85% by weight, more than 90% by weight, more than 91% by weight, more than 92% by weight, more than 93% by weight, more than 94% by weight, more than 95% by weight, more than 96% by weight, more than 97% by weight of the enantiomer.

As used herein and unless otherwise indicated, the term "enantiomerically pure (+)-1,4-dihydro-7-[(3S,4S)-3-methoxy-4-(methylamino)-1-pyrrolidinyl]-4-oxo-1-(2-thiazolyl)-1,8-naphthyridine-3-carboxylic acid" refers to at least about 80% by weight (+)-1,4-dihydro-7-[(3S,4S)-3-methoxy-4-(methylamino)-1-pyrrolidinyl]-4-oxo-1-(2-thiazolyl)-1,8-naphthyridine-3-carboxylic acid and at most about 20% by weight (−)-1,4-dihydro-7-[(3S,4S)-3-methoxy-4-(methylamino)-1-pyrrolidinyl]-4-oxo-1-(2-thiazolyl)-1,8-naphthyridine-3-carboxylic acid, at least about 90% by weight (+)-1,4-dihydro-7-[(3S,4S)-3-methoxy-4-(methylamino)-1-pyrrolidinyl]-4-oxo-1-(2-thiazolyl)-1,8-naphthyridine-3-carboxylic acid and at most about 10% by weight the (−)-enantiomer, at least about 95% by weight (+)-1,4-dihydro-7-[(3S,4S)-3-methoxy-4-(methylamino)-1-pyrrolidinyl]-4-oxo-1-(2-thiazolyl)-1,8-naphthyridine-3-carboxylic acid and at most about 5% by weight the (−)-enantiomer, at least about 97% by weight (+)-1,4-dihydro-7-[(3S,4S)-3-methoxy-4-(methylamino)-1-pyrrolidinyl]-4-oxo-1-(2-thiazolyl)-1,8-naphthyridine-3-carboxylic acid and at most about 3% by weight (−)-enantiomer.

As used herein and unless otherwise indicated, the terms "treat," "treating" and "treatment" refer to alleviating or reducing the severity of a symptom associated with the disease or condition being treated.

The term "prevention" includes the inhibition of a symptom of the particular disease or disorder. In some embodiments, patients with familial history of cancer are candidates for preventive regimens. Generally, the term "preventing" refers to administration of the drug prior to the onset of symptoms, particularly to patients at risk of cancer.

As used herein and unless otherwise indicated, the term "managing" encompasses preventing the recurrence of the particular disease or disorder in a patient who had suffered from it, lengthening the time a patient who had suffered from the disease or disorder remains in remission, reducing mortality rates of the patients, and/or maintaining a reduction in severity or avoidance of a symptom associated with the disease or condition being managed.

As used herein "subject" is an animal, typically a mammal, including human, such as a patient.

As used herein, the term "cancer" includes, but is not limited to, solid tumors and blood born tumors. The term "cancer" refers to disease of skin tissues, organs, blood, and vessels, including, but not limited to, cancers of the bladder, bone or blood, brain, breast, cervix, chest, colon, endrometrium, esophagus, eye, head, kidney, liver, lung, mouth, neck, ovaries, pancreas, prostate, rectum, stomach, testis, throat, and uterus.

As used herein, "hematologic malignancy" refers to cancer of the body's blood-forming and immune system—the bone marrow and lymphatic tissue. Such cancers include leukemias, lymphomas (Non-Hodgkin's Lymphoma), Hodgkin's disease (also called Hodgkin's Lymphoma) and myeloma.

The term "leukemia" refers to malignant neoplasms of the blood-forming tissues. The leukemia includes, but is not limited to, chronic lymphocytic leukemia, chronic myelocytic leukemia, acute lymphoblastic leukemia, acute myelogenous leukemia and acute myeloblastic leukemia. The leukemia can be relapsed, refractory or resistant to conventional therapy.

As used herein "promyelocytic leukemia" or "acute promyelocytic leukemia" refers to a malignancy of the bone marrow in which there is a deficiency of mature blood cells in the myeloid line of cells and an excess of immature cells called promyelocytes. It is usually marked by an exchange of parts of chromosomes 15 and 17.

As used herein "acute lymphocytic leukemia (ALL)", also known as "acute lymphoblastic leukemia" refers to a malignant disease caused by the abnormal growth and development of early nongranular white blood cell or lymphocytes.

As used herein "T-cell leukemia" refers to a disease in which certain cells of the lymphoid system called T lymphocytes or T cells are malignant. T cells are white blood cells that normally can attack virus-infected cells, foreign cells and cancer cells and produce substances that regulate the immune response.

The term "relapsed" refers to a situation where patients who have had a remission of cancer after therapy have a return of cancer cells.

The term "refractory or resistant" refers to a circumstance where patients, even after intensive treatment, have residual cancer cells in their body.

As used herein, the IC$_{50}$ refers to an amount, concentration or dosage of a particular test compound that achieves a 50% inhibition of a maximal response in an assay that measures such response.

As used herein, and unless otherwise specified, the terms "therapeutically effective amount" and "effective amount" of a compound refer to an amount sufficient to provide a therapeutic benefit in the treatment, prevention and/or management of a disease, to delay or minimize one or more symptoms associated with the disease or disorder to be treated. The terms "therapeutically effective amount" and "effective amount" can encompass an amount that improves overall therapy, reduces or avoids symptoms or causes of disease or disorder or enhances the therapeutic efficacy of another therapeutic agent.

As used herein and unless otherwise indicated, the term "pharmaceutically acceptable salt" includes, but is not limited to, salts of acidic or basic groups that can be present in the compounds provided herein. Under certain acidic conditions, the compound can form a wide variety of salts with various inorganic and organic acids. The acids that can be used to prepare pharmaceutically acceptable salts of such basic compounds are those that form salts comprising pharmacologically acceptable anions including, but not limited to, acetate, benzenesulfonate, benzoate, bicarbonate, bitartrate, bromide, calcium edetate, camsylate, carbonate, chloride, bromide, iodide, citrate, dihydrochloride, edetate, edisylate, estolate, esylate, fumarate, gluceptate, gluconate, glutamate, glycollylarsanilate, hexylresorcinate, hydrabamine, hydroxynaphthoate, isethionate, lactate, lactobionate, malate, maleate, mandelate, mesylate, methylsulfate, muscate, napsylate, nitrate, panthothenate, phosphate/diphosphate, polygalacturonate, salicylate, stearate, succinate, sulfate, tannate, tartrate, teoclate, triethiodide and pamoate. Under certain basic conditions, the compound can form base salts with various pharmacologically acceptable cations. Non-limiting examples of such salts include alkali metal or alkaline earth metal salts and, particularly, calcium, magnesium, sodium, lithium, zinc, potassium and iron salts.

As used herein and unless otherwise indicated, the term "hydrate" means a compound provided herein or a salt thereof, that further includes a stoichiometric or non-stoichiometric amount of water bound by non-covalent intermolecular forces.

As used herein and unless otherwise indicated, the term "solvate" means a solvate formed from the association of one or more solvent molecules to a compound provided herein. The term "solvate" includes hydrates (e.g., mono-hydrate, dihydrate, trihydrate, tetrahydrate and the like).

The terms "co-administration" and "in combination with" include the administration of two therapeutic agents (for example, SNS-595 and another anti-cancer agent or second agent) either simultaneously, concurrently or sequentially with no specific time limits. In one embodiment, both agents are present in the cell or in the patient's body at the same time or exert their biological or therapeutic effect at the same time. In one embodiment, the two therapeutic agents are in the same composition or unit dosage form. In another embodiment, the two therapeutic agents are in separate compositions or unit dosage forms.

The term "the supportive care agent" refers to any substance that treats, prevents or manages an adverse effect from SNS-595 treatment.

6. DETAILED DESCRIPTION

6.1 SNS-595

The compound for use in the methods and compositions provided herein is enantiomerically pure (+)-1,4-dihydro-7-[(3S,4S)-3-methoxy-4-(methylamino)-1-pyrrolidinyl]-4-oxo-1-(2-thiazolyl)-1,8-naphthyridine-3-carboxylic acid, which is also known as SNS-595 or AG-7352. SNS-595 has the following chemical structure:

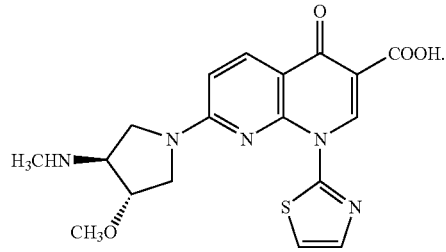

In certain embodiments, pharmaceutically acceptable salts, solvates, hydrates or prodrugs of SNS-595 are used in the methods and compositions provided herein.

SNS-595 can be prepared by methods known to one of skill in the art, for example, according to the preparation procedure for Example C-1 of U.S. Pat. No. 5,817,669, titled "Compounds, processes for the preparation thereof and anti-tumor agents," issued Oct. 6, 1998, and in Japanese Patent Application No. Hei 10-173986, to Chikugi et al., both of which are incorporated herein by reference in their entirety. Certain exemplary pharmaceutical compositions comprising SNS-595 and methods of using the same are described in U.S. Patent Application Pub. Nos. 2005-0203120; 2005-0215583 and 2006-0025437, all of which are incorporated herein by reference in their entirety.

6.2 Methods of Use

Proliferating cells undergo four phases of the cell cycle: $G_1$, 5, $G_2$, and M. These phases were first identified by observing dividing cells as the cells progressed through DNA synthesis which became known as the synthesis or S phase of the cell cycle and mitosis and is known as the mitotic or M phase or S phase of the cell cycle. The observed gaps in time between the completion of DNA synthesis and mitosis and between mitosis to the next cycle of DNA synthesis are as the $G_1$ and $G_2$ phases respectfully. Non-proliferating cells that retain the ability to proliferate under the appropriate conditions are quiescent or in the $G_o$ state and are typically characterized as having exited the cell cycle.

SNS-595 is a cell cycle inhibitor and arrests cells at the $G_2$ interface. Without being limited by a particular theory, SNS-595 mediates the activation of the DNA-PK pathway which eventually leads to apoptotic cell death. These events are S-phase specific, i.e., they occur only during the S phase of the cell cycle. Without being limited by a particular theory, treatment with SNS-595 results in an increase in the number of double-strand DNA breaks that form during the S phase. This damage impedes the ability of the cell to synthesize DNA and lengthens the time the cell spends in the S phase. Once DNA damage is detected in cells, markers for apoptosis rapidly appear. This rapid onset of apoptosis appears to be p73 dependent as shown by a more than 11 fold decrease in SNS-595 sensitivity in p73 null cells as compared to p73 containing cells.

Figure 7:
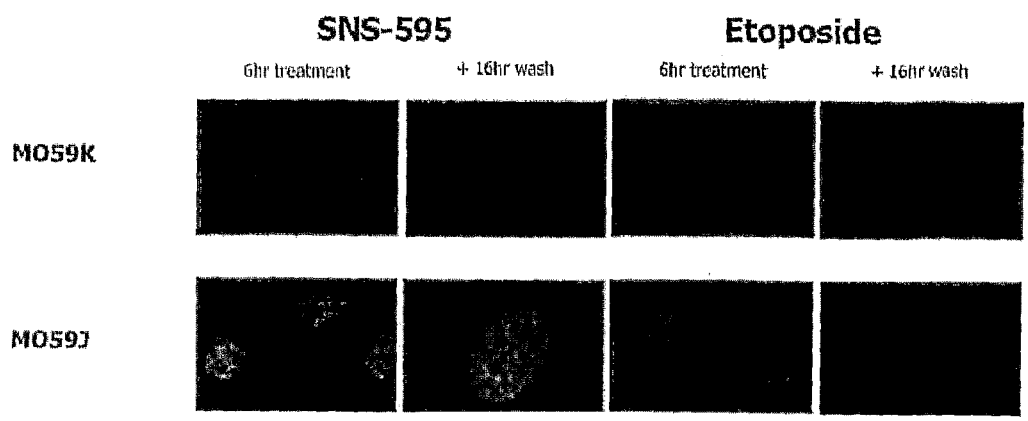
FIG. 7 shows DNA damage induced by SNS-595 and etoposide in the presence (MO59K cells) and absence (MO59J cells) of DNA-PK.

As FIG. 7 exemplifies, the formation of double-strand breaks activates, in a dose dependent manner, the DNA-PK mediated repair and apoptotic cellular machinery including but not limited to: i) DNA-PK expression; ii) H2AX phosphorylation; iii) c-Abl phosphorylation; iv) p53 phosphorylation; v) p73 phosphorylation; vi) p21 expression; vii) caspase-9 activation; and viii) caspase-3 activation. When the DNA damage is sufficiently severe such that the double-strand breaks cannot be repaired through non-homologous end joining (NHEJ), the cell rapidly enters apoptosis. Some cells are able to reach the $G_2$ phase but are subsequently arrested (mediated by cdc2/cyclin B) because the cells are too damaged to enter into the M phase and also eventually becomes apoptotic. Without being limited by a particular theory, because SNS-595 is S-phase selective, doses of SNS-595 that are cytotoxic to proliferating cells (thus are progressing through the cell cycle including the S phase) are non-lethal to non-proliferating cells.

6.2.1 Solid Tumors

Accordingly, provided herein are methods of treating, managing, or preventing cancers comprising administering a dose of about 1 mg/m$^2$ to about 100 mg/m$^2$ of SNS-595 to a mammal in need of such treatment, management or prevention. The cancer types include, but are not limited to, bladder cancer, breast cancer, cervical cancer, colon cancer (including colorectal cancer), esophageal cancer, head and neck cancer, liver cancer, lung cancer (both small cell and non-small cell), melanoma, myeloma, neuroblastoma, ovarian cancer, pancreatic cancer, prostate cancer, renal cancer, sarcoma (including osteosarcoma), skin cancer (including squamous cell carcinoma), stomach cancer, testicular cancer, thyroid cancer, and uterine cancer. In one embodiment, the methods encompass treating, preventing or managing colon, pancreas, breast, mesothelioma, cholangiocarcinoma, leiomyosarcoma, liposarcoma, melanoma, nasopharyngeal, neuroendocrine, ovarian, renal, salivary gland, small cell lung cancer, or spindle cell carcinoma.

6.2.2 Leukemias

In one embodiment, methods provided herein encompass treating, preventing or managing various types of leukemias such as chronic lymphocytic leukemia, chronic myelocytic leukemia, acute lymphoblastic leukemia, acute myelogenous leukemia, and acute myeloblastic leukemia.

In some embodiments, the methods encompass treating, preventing or managing acute leukemia, such as AML, which includes, but is not limited to undifferentiated AML (M0), myeloblastic leukemia (M1), myeloblastic leukemia (M2), promyelocytic leukemia (M3 or M3 variant [M3V]), myelomonocytic leukemia (M4 or M4 variant with eosinophilia [M4E]), monocytic leukemia (M5), erythroleukemia (M6), megakaryoblastic leukemia (M7). In some embodiments, acute lymphocytic leukemia (ALL) includes leukemia that originates in the blast cells of the bone marrow (B-cells), thymus (T-cells), and lymph nodes. The acute lymphocytic leukemia is categorized according to the French-American-British (FAB) Morphological Classification Scheme as L1—Mature-appearing lymphoblasts (T-cells or pre-B-cells), L2—Immature and pleomorphic (variously shaped) lymphoblasts (T-cells or pre-B-cells), and L3—Lymphoblasts (B-cells; Burkitt's cells).

In one embodiment, the acute myelogenous leukemia is undifferentiated AML (M0).

In one embodiment, the acute myelogenous leukemia is myeloblastic leukemia (M1).

In one embodiment, the acute myelogenous leukemia is myeloblastic leukemia (M2).

In one embodiment, the acute myelogenous leukemia is promyelocytic leukemia (M3 or M3 variant [M3V]).

In one embodiment, the acute myelogenous leukemia is myelomonocytic leukemia (M4 or M4 variant with eosinophilia [M4E]).

In one embodiment, the acute myelogenous leukemia is monocytic leukemia (M5).

In one embodiment, the acute myelogenous leukemia is erythroleukemia (M6).

In one embodiment, the acute myelogenous leukemia is megakaryoblastic leukemia (M7).

In one embodiment, the acute lymphocytic leukemia originates in the blast cells of the bone marrow (B-cells)

In one embodiment, the acute lymphocytic leukemia originates in the thymus (T-cells).

In one embodiment, the acute lymphocytic leukemia originates in the lymph nodes.

In one embodiment, the acute lymphocytic leukemia is L1 type characterized by mature-appearing lymphoblasts (T-cells or pre-B-cells).

In one embodiment, the acute lymphocytic leukemia is L2 type characterized by immature and pleomorphic (variously shaped) lymphoblasts (T-cells or pre-B-cells).

In one embodiment, the acute lymphocytic leukemia is L3 type characterized by lymphoblasts (B-cells; Burkitt's cells).

In certain embodiments, the acute myelogenous leukemia is promyelocytic leukemia, or lymphoblastic leukemia. In certain embodiments, the acute lymphocytic leukemia is T-cell leukemia. In one embodiment, methods provided herein encompass methods of treating, preventing or managing promyelocytic leukemia, T-cell leukemia or lymphoblastic leukemia. In one embodiment, the T-cell leukemia is peripheral T-cell leukemia, T-cell lymphoblastic leukemia, cutaneous T-cell leukemia, and adult T-cell leukemia.

In some embodiments, SNS-595 is used to treat drug resistant leukemias, such as chronic myelogenous leukemia (CML). Thus, treatment with SNS-595 could provide an alternative for patients who do not respond to other methods of treatment. In some embodiments, such other methods of treatment encompass treatment with Gleevac®. In some embodiments, provided herein are methods of treatment of Philadelphia chromosome positive chronic myelogenous leukemia (Ph+CML). In some embodiments, provided herein are methods of treatment of Gleevac® resistant Philadelphia chromosome positive chronic myelogenous leukemia (Ph+CML).

The methods provided herein encompass treating patients who have been previously treated for cancer, but are non-responsive to standard therapies, as well as those who have not previously been treated. Also encompassed are methods of treating patients regardless of patient's age, although some diseases or disorders are more common in certain age groups. Further provided are methods of treating patients who have undergone surgery in an attempt to treat the disease or condition at issue, as well as those who have not. Because patients with cancer have heterogenous clinical manifestations and varying clinical outcomes, the treatment given to a patient may vary, depending on his/her prognosis. The skilled clinician will be able to readily determine without undue experimentation specific secondary agents, types of surgery, and types of non-drug based standard therapy that can be effectively used to treat an individual patient with cancer.

The administered dose of SNS-595 can be delivered as a single dose such as, for example, an IV push of 10-15 minutes duration (e.g. a single bolus injection) or over time such as, for example, a 24-hour period (e.g., continuous infusion over time or divided bolus doses over time) and is repeated as necessary, for example, until the patient experiences stable disease or regression, or until the patient experiences disease progression or unacceptable toxicity. For example, stable disease for solid tumors generally means that the perpendicular diameter of measurable lesions has not increased by 25% or more from the last measurement. See e.g., Response Evaluation Criteria in Solid Tumors (RECIST) Guidelines, *Journal of the National Cancer Institute* 92(3): 205-216 (2000). Stable disease or lack thereof is determined by methods known in the art such as evaluation of patient symptoms, physical examination, visualization of the tumor that has been imaged using X-ray, CAT, PET, or MRI scan and other commonly accepted evaluation modalities.

In another embodiment, the dose is about 10 mg/m$^2$-100 mg/m$^2$. In another embodiment, the dose is about 30 mg/m$^2$-75 mg/m$^2$. In another embodiment, the dose is about 40 mg/m$^2$-80 mg/m$^2$. In another embodiment, the dose is about 50 mg/m$^2$-90 mg/m$^2$. In another embodiment, the dose is about 15 mg/m$^2$-80 mg/m$^2$.

In another embodiment the dose is about 20 mg/m$^2$-30 mg/m$^2$. In another embodiment the dose is about 25 mg/m$^2$-35 mg/m$^2$. In another embodiment the dose is about 40 mg/m$^2$-50 mg/m$^2$. In another embodiment the dose is about 45 mg/m$^2$-55 mg/m$^2$. In another embodiment the dose is about 50 mg/m$^2$-60 mg/m$^2$. In another embodiment the dose is about 55 mg/m$^2$-65 mg/m$^2$. In another embodiment the dose is about 60 mg/m$^2$-70 mg/m$^2$. In another embodiment the dose is about 65 mg/m$^2$-75 mg/m$^2$. In another embodiment the dose is about 70 mg/m$^2$-80 mg/m$^2$. In another embodiment the dose is about 75 mg/m$^2$-85 mg/m$^2$. In another embodiment the dose is about 80 mg/m$^2$-90 mg/m$^2$. In another embodiment the dose is about 85 mg/m$^2$-95 mg/m$^2$. In another embodiment the dose is about 90 mg/m$^2$-100 mg/m$^2$.

In other embodiments, SNS-595 is administered in combination with another drug ("second active agent") or another therapy for treating, managing, or preventing cancer. Second active agents include small molecules and large molecules (e.g., proteins and antibodies), examples of which are provided herein, as well as stem cells or cord blood. Methods, or therapies, that can be used in combination with the administration of an SNS-595 include, but are not limited to, surgery, immunotherapy, biological therapy, radiation therapy and other non-drug based therapies presently used to treat, prevent or manage cancer. Various dosing regimens for administration of SNS-595 alone and/or in combination therapy are discussed herein.

Also provided are pharmaceutical compositions (e.g., single unit dosage forms) that can be used in methods disclosed herein. Particular pharmaceutical compositions comprise SNS-595 and a second active agent.

6.3 Doses and Dosing Regimens

In one embodiment, the methods of treating, preventing or managing cancers provided herein comprise administering to a patient on the basis of body surface area, a dose of about 1 mg/m$^2$ to 150 mg/m$^2$ of SNS-595. In another embodiment, the methods of comprise administering a dose of about 1 mg/m$^2$ to 100 mg/m$^2$ of SNS-595. In another embodiment, the methods of comprise administering a dose of about 1 mg/m$^2$ to 75 mg/m$^2$ of SNS-595. In another embodiment, the methods of comprise administering a dose of about 1 mg/m$^2$ to 60 mg/m$^2$ of SNS-595. In another embodiment, the methods of comprise administering a dose of about 1 mg/m$^2$ to 50 mg/m$^2$ of SNS-595. In another embodiment, the methods of comprise administering a dose of about 1 mg/m$^2$ to 48 mg/m$^2$ of SNS-595. In another embodiment, the methods of comprise administering a dose of about 1 mg/m$^2$ to 24 mg/m$^2$ of SNS-595. In another embodiment, the methods of comprise administering a dose of about 3 mg/m$^2$ to 27 mg/m$^2$ of SNS-595 on the basis of body surface area. In another embodiment, the methods of comprise administering a dose of about 3 mg/m$^2$ to 24 mg/m$^2$ of SNS-595 on the basis of body surface area. In another embodiment, the methods of comprise administering a dose of about 10 mg/m$^2$ to 90 mg/m$^2$ of SNS-595 on the basis of body surface area. In another embodiment, the methods of comprise administering a dose of about 15 mg/m$^2$ to 80 mg/m$^2$ of SNS-595 on the basis of body surface area. Body surface area calculations can be calculated for example, with the Mosteller formula wherein:

$$BSA(m^2) = \text{square root of } [(\text{height(cm)} \times \text{weight(kg)})/3600].$$

In another embodiment, the dose is 3 mg/m$^2$ to 24 mg/m$^2$ on the basis of body surface area. In another embodiment, the dose is 3 mg/m² to 18 mg/m² on the basis of body surface area. In another embodiment, the dose is 3 mg/m² to 15 mg/m². In another embodiment, the dose is 1 mg/m², 2 mg/m², 3 mg/m², 4 mg/m², 5 mg/m², 6 mg/m², 7 mg/m², 8 mg/m², 9 mg/m², 10 mg/m², 11 mg/m², 12 mg/m², 13 mg/m², 14 mg/m², 15 mg/m², 16 mg/m², 17 mg/m², 18 mg/m², 19 mg/m², 20 mg/m², 21 mg/m², 22 mg/m², 23 mg/m², 24 mg/m², 25 mg/m², 26 mg/m², 27 mg/m², 30 mg/m², 36 mg/m², 42 mg/m², 48 mg/m², 50 mg/m², 55 mg/m², 60 mg/m² or 65 mg/m² on the basis of body surface area. In another embodiment, the dose is 3 mg/m², 6 mg/m², 9 mg/m², 12 mg/m², 15 mg/m², 18 mg/m², 21 mg/m² 24 mg/m², 25 mg/m², 27 mg/m², 36 mg/m², 48 mg/m² or 50 mg/m².

In one embodiment, the dose is 15 mg/m² on the basis of body surface area. In another embodiment, the dose is 25 mg/m² on the basis of body surface area. In another embodiment, the dose is 30 mg/m² on the basis of body surface area. In one embodiment, the dose is 50 mg/m² on the basis of body surface area.

In another embodiment, the dose is 15 mg/m² to 80 mg/m² on the basis of body surface area. In another embodiment, the dose is 15 mg/m² to 75 mg/m² on the basis of body surface area. In another embodiment, the dose is 20 mg/m² to 65 mg/m². In another embodiment, the dose is 30 mg/m² to 50 mg/m². In another embodiment, the dose is 15 mg/m², 20 mg/m², 25 mg/m², 30 mg/m², 35 mg/m², 40 mg/m², 45 mg/m², 50 mg/m², 55 mg/m², 60 mg/m², 65 mg/m², 70 mg/m², 75 mg/m², or 80 mg/m² on the basis of body surface area.

The administered dose of SNS-595 can be expressed in units other than as mg/m². For example, doses can be expressed as mg/kg. One of ordinary skill in the art would readily know how to convert doses from mg/m² to mg/kg to given either the height or weight of a subject or both (see, http:///wwwfda.gov/cder/cancer/animalframe.htm). For example, a dose of 1 mg/m² to 30 mg/m² for a 65 kg human is approximately equal to 0.026 mg/kg to 0.79 mg/kg. In another example, a dose of 3 mg/m² for a 65 kg human is approximately equal to 0.078 mg/kg. In another example, a dose of 15 mg/m² to 80 mg/m² for a 65 kg human is approximately equal to 0.39 mg/kg to 2.11 mg/kg.

In certain embodiments, the administered dose of SNS-595 can be delivered as a single dose such as, for example, an IV push of 10-15 minutes duration (e.g. a single bolus IV injection) or over time such as, for example, a 24-hour period (e.g., continuous infusion over time or divided bolus doses over time) and is repeated as necessary, for example, until the patient experiences stable disease or regression or until the patient experiences disease progression or unacceptable toxicity. Stable disease or lack thereof is determined by methods known in the art, such as evaluation of patient symptoms, physical examination and other commonly accepted evaluation modalities.

The amount of the pharmaceutical composition administered according to the methods provided herein will depend on the mammal being treated, the severity of the disorder or symptom of the disorder, the manner of administration, the frequency of administration and the judgment of the prescribing physician.

In some embodiments, the frequency of administration is in the range of about a daily dose to about a monthly dose. In certain embodiments, administration is once a day, once every other day, twice a week, once every week, once every two weeks, once every three weeks, or once every four weeks. In one embodiment, the pharmaceutical composition provided herein is administered weekly.

In certain embodiments, SNS-595 is cyclically administered to a patient. Cycling therapy involves the administration of an active agent for a period of time, followed by a rest for a period of time, and repeating this sequential administration. Cycling therapy can reduce the development of resistance to one or more of the therapies, avoid or reduce the side effects of one of the therapies, and/or improves the efficacy of the treatment.

Consequently, in one embodiment, SNS-595 is administered weekly in a single or divided doses in a three to six week cycle with a rest period of about 1 to about 30 days. In another embodiment, SNS-595 is administered weekly in a single or divided doses for one week, two weeks, three weeks, four weeks, five weeks or six weeks with a rest period of 1, 3, 5, 7, 9, 12, 14, 16, 18, 20, 22, 24, 26, 28, 29 or 30 days. In some embodiments, the waiting period is 14 days. In some embodiments, the waiting period is 28 days. In one embodiment, the waiting period is until there is sufficient bone marrow recovery. The frequency, number and length of dosing cycles can be increased or decreased. Thus, another embodiment encompasses the administration of SNS-595 for more cycles than are typical when it is administered alone.

In one embodiment, the methods provided herein comprise: i) administering a dose of about 1 mg/m² to 150 mg/m² of SNS-595 to a patient; ii) waiting a period of at least one day where the mammal is not administered any SNS-595; and iii) administering another dose of about 1 mg/m² to 150 mg/m² of SNS-595 to the patient. In one embodiment, steps ii)-iii) are repeated a plurality of times. In another embodiment, the method comprises administering a dose of 1 mg/m²-100 mg/m² in steps i) and iii).

In one embodiment, for example, in methods for treatment of certain leukemias, the methods provided herein comprise: i) administering a dose of about 10 mg/m²-150 mg/m² of SNS-595 to a mammal; ii) waiting a period of at least one day where the mammal is not administered any SNS-595; iii) administering another dose of about 10 mg/m²-150 mg/m² of SNS-595 to the mammal; and, iv) repeating steps ii)-iii) a plurality of times. In another embodiment, the method comprises administering a dose of 10 mg/m²-100 mg/m² in steps i) and iii).

In one embodiment, the methods provided herein comprise: i) administering a dose of about 1 mg/m² to 75 mg/m² of SNS-595 to a patient; ii) waiting a period of at least one day where the mammal is not administered any SNS-595; and iii) administering another dose of about 1 mg/m² to 75 mg/m² of SNS-595 to the patient. In one embodiment, steps ii)-iii) are repeated a plurality of times.

In one embodiment, the methods provided herein comprise: i) administering a dose of about 1 mg/m² to 48 mg/m² of SNS-595 to a patient; ii) waiting a period of at least one day where the mammal is not administered any SNS-595; and iii) administering another dose of about 1 mg/m² to 48 mg/m² of SNS-595 to the patient. In one embodiment, steps ii)-iii) are repeated a plurality of times.

In one embodiment, the methods provided herein comprise: i) administering a dose of about 1 mg/m² to 24 mg/m² of SNS-595 to a patient; ii) waiting a period of at least one day where the mammal is not administered any SNS-595; and iii) administering another dose of about 1 mg/m² to 24 mg/m² of SNS-595 to the patient. In one embodiment, steps ii)-iii) are repeated a plurality of times.

In another embodiment, the method comprises administering a dose of about 3 mg/m² to 24 mg/m² in steps i) and iii). In yet another embodiment, the method comprises administering a dose of about 15 mg/m² in steps i) and iii). In yet another embodiment, the method comprises administering a dose of about 1 mg/m² to 40 mg/m², about 1.5 mg/m² to 30 mg/m², about 2 mg/m² to 25 mg/m² or about 3 mg/m² to 24 mg/m² in steps i) and iii).

In another embodiment, the method comprises administering a dose of about 15 mg/m² to 80 mg/m² in steps i) and iii). In yet another embodiment, the method comprises administering a dose of about 15 mg/m² to 75 mg/m² in steps i) and iii). In yet another embodiment, the method comprises administering a dose of about 20 mg/m² to 65 mg/m², about 30 mg/m² to 50 mg/m², about 35 mg/m², about 40 mg/m², or about 45 mg/m² in steps i) and iii).

In the above methods, for example, if the waiting period were 6 days, then the initial dose of SNS-595 is administered on Day 1 (step i); the waiting period is six days (step ii); and the following dose of SNS-595 is administered on Day 8 (step iii). Other exemplary time periods include 2 days, 3 days, 5 days, 7 days, 10 days, 12 days, 13 days, 14 days, 15 days, 17 days, 20 days, 27 days and 28 days. In another embodiment, the waiting period is at least 2 days and steps ii) through iii) are repeated at least three times. In another embodiment, the waiting period is at least 3 days and steps ii) through iii) are repeated at least five times. In another embodiment, the waiting period is at least 3 days and steps ii) through iii) are repeated at least three times. In another embodiment, the waiting period is at least 3 days and steps ii) through iii) are repeated at least five times. In another embodiment, the waiting period is at least 6 days and steps ii) through iii) are repeated at least three times. In another embodiment, the waiting period is at least 6 days and steps ii) through iii) are repeated at least five times. In another embodiment, the waiting period is at least 14 days and steps ii) through iii) are repeated at least three times. In another embodiment, the waiting period is at least 20 days and steps ii) through iii) are repeated at least three times. In another embodiment, the waiting period is at least 20 days and steps ii) through iii) are repeated at least five times. In another embodiment, the waiting period is at least 28 days and steps ii) through iii) are repeated at least three times. In another embodiment, the waiting period is at least 27 days and steps ii) through iii) are repeated at least five times. In another embodiment, the waiting period is at least 28 days and steps ii) through iii) are repeated at least five times.

In another embodiment, the dosing method comprises administering a dose of SNS-595 twice a week (dosing on days 1, 4, 8 and 11) to a mammal. In another embodiment, the dosing method comprises administering a weekly dose of SNS-595 to a mammal. In another embodiment, the dosing method comprises administering a dose of SNS-595 to a mammal every two weeks. In another embodiment, the dosing method comprises administering a dose of SNS-595 to a mammal every three weeks. In another embodiment, the dosing method comprises administering a dose of SNS-595 to a mammal every four weeks.

In another embodiment, the dosing method comprises a cycle wherein the cycle comprises administering a dose of SNS-595 to a mammal once a week for three weeks followed by a period of at least 14 days where no SNS-595 is administered to the mammal and wherein the cycle is repeated a plurality of times. In another embodiment, the period where no SNS-595 is administered is 14 days. In another embodiment, the period where no SNS-595 is administered is 21 days.

In another embodiment, the methods provided herein comprise: i) administering a dose of about 1 mg/m² to 100 mg/m² of SNS-595 to a mammal once a week for 3 weeks; ii) waiting a period of 14 days where the mammal is not administered any SNS-595; and iii) administering another dose of about 1 mg/m² to 100 mg/m² of SNS-595 to the mammal once a week for 3 weeks. In one embodiment, steps ii)-iii) are repeated a plurality of times.

In another embodiment, the methods provided herein comprise: i) administering a dose of about 1 mg/m² to 75 mg/m² of SNS-595 to a mammal once a week for 3 weeks; ii) waiting a period of 14 days where the mammal is not administered any SNS-595; and iii) administering another dose of about 1 mg/m² to 75 mg/m² of SNS-595 to the mammal once a week for 3 weeks. In one embodiment, steps ii)-iii) are repeated a plurality of times.

In another embodiment, the methods provided herein comprise: i) administering a dose of about 1 mg/m² to 60 mg/m² of SNS-595 to a mammal once a week for 3 weeks; ii) waiting a period of 14 days where the mammal is not administered any SNS-595; and iii) administering another dose of about 1 mg/m² to 60 mg/m² of SNS-595 to the mammal once a week for 3 weeks. In one embodiment, steps ii)-iii) are repeated a plurality of times.

In another embodiment, the methods provided herein comprise: i) administering a dose of about 1 mg/m²-50 mg/m² of SNS-595 to a mammal once a week for 3 weeks; ii) waiting a period of 14 days where the mammal is not administered any SNS-595; iii) administering another dose of about 1 mg/m²-50 mg/m² of SNS-595 to the mammal once a week for 3 weeks; and, iv) repeating steps ii)-iii) a plurality of times.

In another embodiment, the methods provided herein comprise: i) administering a dose of about 1 mg/m² to 48 mg/m² of SNS-595 to a mammal once a week for 3 weeks; ii) waiting a period of 14 days where the mammal is not administered any SNS-595; and iii) administering another dose of about 1 mg/m² to 48 mg/m² of SNS-595 to the mammal once a week for 3 weeks. In one embodiment, steps ii)-iii) are repeated a plurality of times.

In another embodiment, the methods provided herein comprise: i) administering a dose of about 1 mg/m² to 24 mg/m² of SNS-595 to a mammal once a week for 3 weeks; ii) waiting a period of 14 days where the mammal is not administered any SNS-595; and iii) administering another dose of about 1 mg/m² to 24 mg/m² of SNS-595 to the mammal once a week for 3 weeks. In one embodiment, steps ii)-iii) are repeated a plurality of times.

In another embodiment, the methods provided herein comprise: i) administering a dose of about 2 mg/m² to 40 mg/m² of SNS-595 to a mammal once a week for 3 weeks; ii) waiting a period of 14 days where the mammal is not administered any SNS-595; and iii) administering another dose of 2 mg/m² to 40 mg/m² of SNS-595 to the mammal once a week for 3 weeks. In one embodiment, steps ii)-iii) are repeated a plurality of times.

In another embodiment, the methods provided herein comprise: i) administering a dose of about 3 mg/m² to 24 mg/m² of SNS-595 to a mammal once a week for 3 weeks; ii) waiting a period of 14 days where the mammal is not administered any SNS-595; and iii) administering another dose of about 3 mg/m² to 24 mg/m² of SNS-595 to the mammal once a week for 3 weeks. In one embodiment, steps ii)-iii) are repeated a plurality of times.

In another embodiment, the methods provided herein comprise: i) administering a dose of about 3 mg/m² to 24 mg/m² of SNS-595 to a mammal once a week for 3 weeks (e.g. dosing in days 1, 8 and 15); ii) waiting a period of at least 28 days where the mammal is not administered any SNS-595; and iii) administering another dose of about 3 mg/m² to 24 mg/m² of SNS-595 to the mammal once a week for 3 weeks. In one embodiment, steps ii)-iii) are repeated a plurality of times.

In another embodiment, the methods provided herein comprise: i) administering a dose of about 3 mg/m$^2$ to 24 mg/m$^2$ of SNS-595 to a mammal twice a week for 2 weeks (dosing in days 1, 4, 8 and 11); ii) waiting a period of at least 28 days where the mammal is not administered any SNS-595; and iii) administering another dose of about 3 mg/m$^2$ to 24 mg/m$^2$ of SNS-595 to the mammal twice a week for 2 weeks (dosing in days 1, 4, 8 and 11). In one embodiment, steps ii)-iii) are repeated a plurality of times.

In another embodiment, the methods provided herein comprise: i) administering a dose of about 3 mg/m$^2$ to 24 mg/m$^2$ of SNS-595 to a mammal once a week for 3 weeks (e.g. dosing in days 1, 8 and 15); ii) waiting a period of 28 days where the mammal is not administered any SNS-595; and iii) administering another dose of about 3 mg/m$^2$ to 24 mg/m$^2$ of SNS-595 to the mammal once a week for 3 weeks. In one embodiment, steps ii)-iii) are repeated a plurality of times.

In another embodiment, the methods provided herein comprise: i) administering a dose of about 3 mg/m$^2$ to 24 mg/m$^2$ of SNS-595 to a mammal twice a week for 2 weeks (dosing in days 1, 4, 8 and 11); ii) waiting a period of 28 days where the mammal is not administered any SNS-595; and iii) administering another dose of about 3 mg/m$^2$ to 24 mg/m$^2$ of SNS-595 to the mammal twice a week for 2 weeks (dosing in days 1, 4, 8 and 11). In one embodiment, steps ii)-iii) are repeated a plurality of times.

In another embodiment, the methods provided herein comprise: i) administering a dose of about 15 mg/m$^2$ to 80 mg/m$^2$ of SNS-595 to a mammal once a week for 3 weeks; ii) waiting a period of 14 days where the mammal is not administered any SNS-595; and iii) administering another dose of about 15 mg/m$^2$ to 80 mg/m$^2$ of SNS-595 to the mammal once a week for 3 weeks. In one embodiment, steps ii)-iii) are repeated a plurality of times.

In another embodiment, the methods provided herein comprise: i) administering a dose of about 15 mg/m$^2$ to 80 mg/m$^2$ of SNS-595 to a mammal once a week for 3 weeks (e.g. dosing in days 1, 8 and 15); ii) waiting a period of at least 28 days where the mammal is not administered any SNS-595; and iii) administering another dose of about 15 mg/m$^2$ to 80 mg/m$^2$ of SNS-595 to the mammal once a week for 3 weeks. In one embodiment, steps ii)-iii) are repeated a plurality of times.

In another embodiment, the methods provided herein comprise: i) administering a dose of about 15 mg/m$^2$ to 80 mg/m$^2$ of SNS-595 to a mammal twice a week for 2 weeks (dosing in days 1, 4, 8 and 11); ii) waiting a period of at least 28 days where the mammal is not administered any SNS-595; and iii) administering another dose of about 15 mg/m$^2$ to 80 mg/m$^2$ of SNS-595 to the mammal twice a week for 2 weeks (dosing in days 1, 4, 8 and 11). In one embodiment, steps ii)-iii) are repeated a plurality of times.

In another embodiment, the methods provided herein comprise: i) administering a dose of about 15 mg/m$^2$ to 80 mg/m$^2$ of SNS-595 to a mammal once a week for 3 weeks (e.g. dosing in days 1, 8 and 15); ii) waiting a period of 28 days where the mammal is not administered any SNS-595; and iii) administering another dose of about 15 mg/m$^2$ to 80 mg/m$^2$ of SNS-595 to the mammal once a week for 3 weeks. In one embodiment, steps ii)-iii) are repeated a plurality of times.

In another embodiment, the methods provided herein comprise: i) administering a dose of about 15 mg/m$^2$ to 80 mg/m$^2$ of SNS-595 to a mammal twice a week for 2 weeks (dosing in days 1, 4, 8 and 11); ii) waiting a period of 28 days where the mammal is not administered any SNS-595; and iii) administering another dose of about 15 mg/m$^2$ to 80 mg/m$^2$ of SNS-595 to the mammal twice a week for 2 weeks (dosing in days 1, 4, 8 and 11). In one embodiment, steps ii)-iii) are repeated a plurality of times.

In another embodiment, the method comprises administering a dose of 1 mg/m$^2$ to 100 mg/m$^2$ of SNS-595 to a patient once a week wherein the one-week period comprises a treatment cycle and the treatment cycle is repeated at least three times. In another embodiment, the method comprises administering a dose of 1 mg/m$^2$ to 75 mg/m$^2$ of SNS-595 to a patient once a week wherein the one-week period comprises a treatment cycle and the treatment cycle is repeated at least three times. In another embodiment, the method comprises administering a dose of 1 mg/m$^2$ to 60 mg/m$^2$ of SNS-595 to a patient once a week wherein the one-week period comprises a treatment cycle and the treatment cycle is repeated at least three times. In another embodiment, the method comprises administering a dose of 1 mg/m$^2$ to 48 mg/m$^2$ of SNS-595 to a patient once a week wherein the one-week period comprises a treatment cycle and the treatment cycle is repeated at least three times. In another embodiment, the method comprises administering a dose of 1 mg/m$^2$ to 24 mg/m$^2$ of SNS-595 to a patient once a week wherein the one-week period comprises a treatment cycle and the treatment cycle is repeated at least three times. In another embodiment, the dose is about 2 mg/m$^2$ to 40 mg/m$^2$ once a week wherein the one-week period comprises a treatment cycle and the treatment cycle is repeated at least three times. In another embodiment, the dose is about 3 mg/m$^2$ to 24 mg/m$^2$ once a week wherein the one-week period comprises a treatment cycle and the treatment cycle is repeated at least three times. In another embodiment, the dose is about 15 mg/m$^2$ once a week wherein the one-week period comprises a treatment cycle and the treatment cycle is repeated at least three times.

In another embodiment, the method comprises administering a dose of 15 mg/m$^2$ to 80 mg/m$^2$ of SNS-595 to a patient once a week wherein the one-week period comprises a treatment cycle and the treatment cycle is repeated at least three times. In another embodiment, the method comprises administering a dose of 15 mg/m$^2$ to 75 mg/m$^2$ of SNS-595 to a patient once a week wherein the one-week period comprises a treatment cycle and the treatment cycle is repeated at least three times. In another embodiment, the method comprises administering a dose of 20 mg/m$^2$ to 65 mg/m$^2$ of SNS-595 to a patient once a week wherein the one-week period comprises a treatment cycle and the treatment cycle is repeated at least three times. In another embodiment, the method comprises administering a dose of 30 mg/m$^2$ to 50 mg/m$^2$ of SNS-595 to a patient once a week wherein the one-week period comprises a treatment cycle and the treatment cycle is repeated at least three times.

In some embodiments, the method comprises administering a dose of about 1 mg/m$^2$ to 40 mg/m$^2$ of SNS-595 to a patient once a week (e.g. dosing in days 1, 8 and 15) wherein the one-week period comprises a treatment cycle and the treatment cycle is repeated at least three times followed by a waiting period of at least 28 days. In some embodiments, the method comprises administering a dose of about 1 mg/m$^2$ to 40 mg/m$^2$ of SNS-595 to a patient twice a week (dosing in days 1, 4, 8, and 11) wherein the one-week period comprises a treatment cycle and the treatment cycle is repeated at least three times followed by a waiting period of at least 28 days. In some embodiments, the method comprises administering a dose of about 1 mg/m$^2$ to 40 mg/m$^2$ of SNS-595 to a patient once a week (e.g. dosing in days 1, 8 and 15) wherein the one-week period comprises a treatment cycle and the treatment cycle is repeated at least three times followed by a waiting period of 28 days. In some embodiments, the method comprises administering a dose of about 1 mg/m² to 40 mg/m² of SNS-595 to a patient twice a week (dosing in days 1, 4, 8, and 11) wherein the one-week period comprises a treatment cycle and the treatment cycle is repeated at least three times followed by a waiting period of 28 days.

In some embodiments, the method comprises administering a dose of about 3 mg/m² to 24 mg/m² of SNS-595 to a patient once a week (e.g. dosing in days 1, 8 and 15) wherein the one-week period comprises a treatment cycle and the treatment cycle is repeated at least three times followed by a waiting period of at least 28 days. In some embodiments, the method comprises administering a dose of about 3 mg/m² to 24 mg/m² of SNS-595 to a patient twice a week (dosing in days 1, 4, 8, and 11) wherein the one-week period comprises a treatment cycle and the treatment cycle is repeated at least three times followed by a waiting period of at least 28 days. In some embodiments, the method comprises administering a dose of about 3 mg/m² to 24 mg/m² of SNS-595 to a patient once a week (e.g. dosing in days 1, 8 and 15) wherein the one-week period comprises a treatment cycle and the treatment cycle is repeated at least three times followed by a waiting period of 28 days. In some embodiments, the method comprises administering a dose of about 3 mg/m² to 24 mg/m² of SNS-595 to a patient twice a week (dosing in days 1, 4, 8, and 11) wherein the one-week period comprises a treatment cycle and the treatment cycle is repeated at least three times followed by a waiting period of 28 days.

In some embodiments, the method comprises administering a dose of about 15 mg/m² to 80 mg/m² of SNS-595 to a patient once a week (e.g. dosing in days 1, 8 and 15) wherein the one-week period comprises a treatment cycle and the treatment cycle is repeated at least three times followed by a waiting period of at least 28 days. In some embodiments, the method comprises administering a dose of about 15 mg/m² to 80 mg/m² of SNS-595 to a patient twice a week (dosing in days 1, 4, 8, and 11) wherein the one-week period comprises a treatment cycle and the treatment cycle is repeated at least three times followed by a waiting period of at least 28 days. In some embodiments, the method comprises administering a dose of about 15 mg/m² to 80 mg/m² of SNS-595 to a patient once a week (e.g. dosing in days 1, 8 and 15) wherein the one-week period comprises a treatment cycle and the treatment cycle is repeated at least three times followed by a waiting period of 28 days. In some embodiments, the method comprises administering a dose of about 15 mg/m² to 80 mg/m² of SNS-595 to a patient twice a week (dosing in days 1, 4, 8, and 11) wherein the one-week period comprises a treatment cycle and the treatment cycle is repeated at least three times followed by a waiting period of 28 days.

In another embodiment, the method comprises administering a dose of about 1 mg/m²-50 mg/m² of SNS-595 to a mammal once a week wherein the one-week period comprises a treatment cycle and the treatment cycle is repeated at least twice. In another embodiment, the dose is about 2 mg/m²-40 mg/m². In another embodiment, the dose is about 3 mg/m²-24 mg/m². In another embodiment, the dose is about 4 mg/m²-20 mg/m².

6.4 Exemplary Dosing Regimens

Exemplary dosing regimens in connection with specific cancers are provide below. These dosing regimens are intended to be illustrative, but not exclusive.

In one aspect a method of treating a solid tumor is provided. The method comprises:
  i) administering a dose of about 1 mg/m² to 100 mg/m² of SNS-595 to a patient;
  ii) waiting a period of at least six days where the subject is not administered any SNS-595;
  iii) administering another dose of about 1 mg/m² to 100 mg/m² of SNS-595 to the patient; and,
  iv) repeating steps ii)-iii) a plurality of times.

In another aspect, a method of treating solid tumors comprises administering a dose of about 1 mg/m² to 75 mg/m² of SNS-595 to a patient once a week wherein the one-week period comprises a treatment cycle and the treatment cycle is repeated at least twice. In another embodiment, the dose is about 15 mg/m² to 80 mg/m². In another embodiment, the dose is about 3 mg/m² to 24 mg/m².

In another aspect, the method of treating solid tumors comprises administering a dose of about 15 mg/m² to 40 mg/m² of SNS-595 to a patient once a week for three weeks followed by a period of at least two weeks where no SNS-595 is administered to said subject and wherein the cycle is repeated a plurality of times.

In another embodiment, the dose is about 15 mg/m² to 35 mg/m². In another embodiment, the dose is about 20 mg/m² to 30 mg/m². In another embodiment, the dose is about 20 mg/m² to 25 mg/m².

In another aspect, the method of treating solid tumors comprises administering a dose of about 35 mg/m² to 80 mg/m² of SNS-595 to a patient once in a three-week period wherein the three week period comprises a treatment cycle and the treatment cycle is repeated at least twice.

In another aspect, a method of treating hematologic malignancies are provided herein. Such methods, in certain embodiment, comprise administering a dose of about 20 mg/m² to 60 mg/m² of SNS-595 to a patient.

In patients who are considered heavily pretreated ("heavily pretreated patients"), the method comprises administering a dose of 35 mg/m² to 60 mg/m² of SNS-595 to a patient once in a three week period wherein the three week period comprises a treatment cycle and the treatment cycle is repeated at least twice. In another embodiment, the method for treating a heavily pretreated patient comprises, administering a dose of 40 mg/m² to 50 mg/m². In another embodiment, the method for treating a heavily pretreated patient, comprises administering a dose of 45 mg/m² to 50 mg/m². A heavily pretreated patient is defined as described by Tolcher et al., *J. Clin. Oncol.* 19: 2937-2947 (2001) and is a patient who has been treated previously with more than six courses of an alkylating agent-containing chemotherapy regimen, more than two courses of carboplatin or mitomycin C, any prior nitrosourea-containing regimen, irradiation to 25% of the bone-marrow containing areas, high-dose chemotherapy requiring hematopoietic stem-cell reinfusions, or widespread metastases to bone.

Patients, who have not been treated previously for their solid tumors or have been treated but are not considered heavily pretreated, are minimally pretreated ("minimally pretreated patients"). For treating minimally pretreated patients, the method comprises administering a dose of 45 mg/m² to 80 mg/m² of SNS-595 to a patient once in a three week period wherein the three week period comprises a treatment cycle and the treatment cycle is repeated at least twice. In another embodiment, the method for treating a minimally pretreated patient comprises, administering a dose of 50 mg/m² to 75 mg/m². In another embodiment, the method for treating a minimally pretreated patient, comprises administering a dose of 55 mg/m² to 70 mg/m². In another embodiment, the method for treating a minimally pretreated patient, comprises administering a dose of 55 mg/m² to 65 mg/m².

In another aspect, a method of treating a hematologic cancer such as leukemias and lymphomas is provided. The method comprises:

i) administering a dose of 10 mg/m$^2$-50 mg/m$^2$ of SNS-595 to a patient;
ii) waiting a period of at least two days where the subject is not administered any SNS-595;
iii) administering another dose of 10 mg/m$^2$-50 mg/m$^2$ of SNS-595 to the patient; and,
iv) repeating steps ii)-iii) a plurality of times.

In one embodiment, the waiting period is six days. In another embodiment, the waiting period is two days. In another embodiment, the waiting period is three days.

In one embodiment, the method of treating hematologic malignancy comprises administering a dose of about 20 mg/m$^2$, 22 mg/m$^2$, 25 mg/m$^2$, 27 mg/m$^2$ or 30 mg/m$^2$ of SNS-595 to a patient once a week wherein the one-week period comprises a treatment cycle and the treatment cycle is repeated at least twice. In one embodiment, the method of treating hematologic malignancy comprises administering a dose of about 25 mg/m$^2$ of SNS-595 to a patient once a week wherein the one-week period comprises a treatment cycle and the treatment cycle is repeated at least twice.

Other dosing schedules useful for treatment of patients with hematologic malignacies can include about 25 mg/m$^2$ to about 50 mg/m$^2$ administered twice a week for two weeks. In another embodiment, the dosing schedules use in treatment of hematologic malignancies include about 30 mg/m$^2$ to about 45 mg/m$^2$ administered twice a week for two weeks. In another embodiment, the dosing schedules for treatment of hematologic malignancies include 30, 35, 40, or 45 mg/m$^2$ administered twice a week for two weeks.

In one embodiment, the method of treating hematologic malignancy comprises administering a dose of about 40 mg/m$^2$, 45 mg/m$^2$, 50 mg/m$^2$, 55 mg/m$^2$ or 60 mg/m$^2$ of SNS-595 to a patient once in two weeks wherein the two-week period comprises a treatment cycle. In one embodiment, the method of treating hematologic malignancy comprises administering a dose of about 50 mg/m$^2$ of SNS-595 to a patient once in two weeks wherein the two-week period comprises a treatment cycle.

6.5 Combination Therapy

In the methods and compositions provided herein, SNS-595 can be used with or combined with other pharmacologically active compounds ("second active agents"). It is believed that certain combinations work synergistically in the treatment of particular types of cancers. SNS-595 can also work to alleviate adverse effects associated with certain second active agents, and some second active agents can be used to alleviate adverse effects associated with SNS-595.

6.5.1 Second Active Agents

One or more second active ingredients or agents can be used in the methods and compositions provided herein together with SNS-595. Second active agents can be large molecules (e.g., proteins) or small molecules (e.g., synthetic inorganic, organometallic or organic molecules).

Examples of large molecule active agents include, but are not limited to, hematopoietic growth factors, cytokines, and monoclonal and polyclonal antibodies, particularly therapeutic antibodies to cancer antigens. Typical large molecule active agents are biological molecules, such as naturally occurring or artificially made proteins. Proteins that are particularly useful in the methods and compositions provided herein include proteins that stimulate the survival and/or proliferation of hematopoietic precursor cells and immunologically active poietic cells in vitro or in vivo. Others stimulate the division and differentiation of committed erythroid progenitors in cells in vitro or in vivo. Particular proteins include, but are not limited to: interleukins, such as IL-2 (including recombinant IL-II ("rIL2") and canarypox IL-2), IL-10, IL-12, and IL-18; interferons, such as interferon alfa-2a, interferon alfa-2b, interferon alfa-n1, interferon alfa-n3, interferon beta-I a, and interferon gamma-I b; GM-CF and GM-CSF; and EPO.

Particular proteins that can be used in the methods and compositions include, but are not limited to: filgrastim, which is sold in the United States under the trade name Neupogen® (Amgen, Thousand Oaks, Calif.) and its derivatives including, but not limited to pegfilgrastim; sargramostim, which is sold in the United States under the trade name Leukine® (Immunex, Seattle, Wash.); recombinant EPO, which is sold in the United States under the trade name Epogen® (Amgen, Thousand Oaks, Calif.); epoetin alfa; and darbepoetin alfa.

Recombinant and mutated forms of GM-CSF can be prepared as described in U.S. Pat. Nos. 5,391,485; 5,393,870 and 5,229,496, all of which are incorporated herein by reference. Recombinant and mutated forms of G-CSF can be prepared as described in U.S. Pat. Nos. 4,810,643; 4,999,291; 5,528,823 and 5,580,755, all of which are incorporated herein by reference.

Also provided for use in combination with SNS-595 are native, naturally occurring, and recombinant proteins. Further encompassed are mutants and derivatives (e.g., modified forms) of naturally occurring proteins that exhibit, in vivo, at least some of the pharmacological activity of the proteins upon which they are based. Examples of mutants include, but are not limited to, proteins that have one or more amino acid residues that differ from the corresponding residues in the naturally occurring forms of the proteins. Also encompassed by the term "mutants" are proteins that lack carbohydrate moieties normally present in their naturally occurring forms (e.g., nonglycosylated forms). Examples of derivatives include, but are not limited to, pegylated derivatives and fusion proteins, such as proteins formed by fusing IgG1 or IgG3 to the protein or active portion of the protein of interest. See, e.g., Penichet, M. L. and Morrison, S. L., *J. Immunol. Methods* 248:91-101 (2001).

Antibodies that can be used in combination with SNS-595 include monoclonal and polyclonal antibodies. Examples of antibodies include, but are not limited to, trastuzumab (Herceptin®), rituximab (Rituxan®), bevacizumab (Avastin™), pertuzumab (Omnitarg™), tositumomab (Bexxar®), edrecolomab (Panorex®), and G250. SNS-595 can also be combined with or used in combination with, anti-TNF-α antibodies, and/or anti-EGFR antibodies such as, for example, Erbitux® or panitumumab.

Large molecule active agents may be administered in the form of anti-cancer vaccines. For example, vaccines that secrete or cause the secretion of, cytokines such as IL-2, G-CSF, and GM-CSF can be used in the methods and pharmaceutical compositions provided. See, e.g., Emens, L. A., et al., *Curr. Opinion Mol. Ther.* 3(1):77-84 (2001).

In contrast to the general rule that drugs with different mechanism of actions be selected to maximize the likelihood for additivity or synergy (see e.g., Page, R. and Takimoto, C., "Principles of Chemotherapy", *Cancer Management: A Multidisciplinary Approach* (2001), p. 23), combinations comprising SNS-595 and a second agent that also impedes DNA synthesis were found to be additive or synergistic.

As used herein, an agent impedes DNA synthesis when it directly or indirectly affects a cell's ability to synthesize DNA or to repair DNA damage. The agent can directly interact with DNA (e.g., bind to or intercalate with) or it can bind to a DNA-binding protein that is involved in DNA synthesis or DNA repair. In general, an agent that impedes DNA synthesis is active during the S phase but need not be S phase specific.

Since SNS-595 affects the DNA-PK pathway, second agent may be an agent that mediates its cytotoxicity through the DNA-PK pathway. One examples is an agent that inhibits non-homologous endjoining repair such as DNA-PK inhibitors. As used herein, and unless otherwise indicated, the term "DNA-PK inhibitor" means an agent that inhibits or interferes with a signaling pathway mediated by DNA-PK. The inhibition of the activity of DNA-PK may be direct (e.g., a catalytic inhibitor of DNA-PK itself) or indirect (e.g., an agent that interferes with the formation of the active DNA-PK complex (DNA-PK, Ku70 and Ku80)). Other examples include, but are not limited to, ligase IV inhibitors and apoptosis enhancing agents such as, but not limited to, caspase-9 activators, caspase-3 activators, and Hsp90 inhibitors.

Second active agents that are small molecules can also be used to alleviate adverse effects associated with the administration of SNS-595. However, like some large molecules, many are believed to be capable of providing a synergistic effect when administered with (e.g., before, after or simultaneously) SNS-595. Examples of small molecule second active agents include, but are not limited to, anti-cancer agents, antibiotics, immunosuppressive agents, and steroids.

Examples of anti-cancer agents include, but are not limited to, alkylating agents, anti-neoplastic agents, anti-metabolites (e.g., folate analogs, purine analogs, adenosine analogs, pyrimidine analogs, and substituted ureas), platinum coordination complexes, topoisomerase II inhibitors, and radiation.

Specific anticancer agents include, but are not limited to: acivicin; aclarubicin; acodazole hydrochloride; acronine; adozelesin; aldesleukin; altretamine; ambomycin; ametantrone acetate; amsacrine; anastrozole; anthramycin; asparaginase; asperlin; azacitidine; azetepa; azotomycin; batimastat; benzodepa; bicalutamide; bisantrene hydrochloride; bisnafide dimesylate; bizelesin; bleomycin sulfate; brequinar sodium; bropirimine; busulfan; cactinomycin; calusterone; capecitabline; caracemide; carbetimer; carboplatin; carmustine; carubicin hydrochloride; carzelesin; cedefingol; celecoxib (COX-2 inhibitor); chlorambucil; cirolemycin; cisplatin; cladribine; crisnatol mesylate; cyclophosphamide; cytarabine; dacarbazine; dactinomycin; daunorubicin hydrochloride; decitabine; dexormaplatin; dezaguanine; dezaguanine mesylate; diaziquone; docetaxel; doxorubicin; doxorubicin hydrochloride; droloxifene; droloxifene citrate; dromostanolone propionate; duazomycin; edatrexate; eflornithine hydrochloride; elsamitrucin; enloplatin; enpromate; epipropidine; epirubicin hydrochloride; erbulozole; erlotinib; esorubicin hydrochloride; estramustine; estramustine phosphate sodium; etanidazole; etoposide; etoposide phosphate; etoprine; fadrozole hydrochloride; fazarabine; fenretinide; floxuridine; fludarabine phosphate; fluorouracil; fluorocitabine; fosquidone; fostriecin sodium; gefitinib; gemcitabine; gemcitabine hydrochloride; hydroxyurea; idarubicin hydrochloride; ifosfamide; ilmofosine; iproplatin; irinotecan; irinotecan hydrochloride; lanreotide acetate; letrozole; leuprolide acetate; liarozole hydrochloride; lometrexol sodium; lomustine; losoxantrone hydrochloride; masoprocol; maytansine; mechlorethamine hydrochloride; megestrol acetate; melengestrol acetate; melphalan; menogaril; mercaptopurine; methotrexate; methotrexate sodium; metoprine; meturedepa; mitindomide; mitocarcin; mitocromin; mitogillin; mitomalcin; mitomycin; mitosper; mitotane; mitoxantrone hydrochloride; mycophenolic acid; nocodazole; nogalamycin; ormaplatin; oxisuran; paclitaxel; pegaspargase; peliomycin; pemetrexed; pentamustine; peplomycin sulfate; perfosfamide; pipobroman; piposulfan; piroxantrone hydrochloride; plicamycin; plomestane; porfimer sodium; porfiromycin; prednimustine; procarbazine hydrochloride; puromycin; puromycin hydrochloride; pyrazofurin; riboprine; safingol; safingol hydrochloride; semustine; simtrazene; sparfosate sodium; sparsomycin; spirogermanium hydrochloride; spiromustine; spiroplatin; streptonigrin; streptozocin; sulofenur; talisomycin; tecogalan sodium; taxotere; tegafur; teloxantrone hydrochloride; temoporfin; teniposide; teroxirone; testolactone; thiamiprine; thioguanidine; thioguanine; thiotepa; tiazofurin; tirapazamine; toremifene citrate; trestolone acetate; triciribine phosphate; trimetrexate; trimetrexate glucuronate; triptorelin; tubulozole hydrochloride; uracil mustard; uredepa; vapreotide; verteporfin; vinblastine sulfate; vincristine sulfate; vindesine; vindesine sulfate; vinepidine sulfate; vinglycinate sulfate; vinleurosine sulfate; vinorelbine tartrate; vinrosidine sulfate; vinzolidine sulfate; vorozole; zeniplatin; zinostatin; and zorubicin hydrochloride.

Other anti-cancer drugs include, but are not limited to: 20-epi-1,25 dihydroxyvitamin D3; 5-ethynyluracil; abiraterone; aclarubicin; acylfulvene; adecypenol; adozelesin; aldesleukin; ALL-TK antagonists; altretamine; ambamustine; amidox; amifostine; aminolevulinic acid; amrubicin; amsacrine; anagrelide; anastrozole; andrographolide; angiogenesis inhibitors; antagonist D; antagonist G; antarelix; anti-dorsalizing morphogenetic protein-1; antiandrogen, prostatic carcinoma; antiestrogen; antineoplaston; antisense oligonucleotides; aphidicolin glycinate; apoptosis gene modulators; apoptosis regulators; apurinic acid; ara-CDP-DL-PTBA; arginine deaminase; asulacrine; atamestane; atrimustine; axinastatin 1; axinastatin 2; axinastatin 3; azasetron; azatoxin; azatyrosine; baccatin III derivatives; balanol; batimastat; BCR/ABL antagonists; benzochlorins; benzoylstaurosporine; beta lactam derivatives; beta-alethine; betaclamycin B; betulinic acid; bFGF inhibitor; bicalutamide; bisantrene; bisaziridinylspermine; bisnafide; bistratene A; bizelesin; breflate; bropirimine; budotitane; buthionine sulfoximine; calcipotriol; calphostin C; camptothecin derivatives; capecitabine; carboxamide-amino-triazole; carboxyamidotriazole; CaRest M3; CARN 700; cartilage derived inhibitor; carzelesin; casein kinase inhibitors (ICOS); castanospermine; cecropin B; cetrorelix; chlorins; chloroquinoxaline sulfonamide; cicaprost; cis-porphyrin; cladribine; clomifene analogues; clotrimazole; collismycin A; collismycin B; combretastatin A4; combretastatin analogue; conagenin; crambescidin 816; crisnatol; cryptophycin 8; cryptophycin A derivatives; curacin A; cyclopentanthraquinones; cycloplatam; cypemycin; cytarabine ocfosfate; cytolytic factor; cytostatin; dacliximab; decitabine; dehydrodidemnin B; deslorelin; dexamethasone; dexifosfamide; dexrazoxane; dexverapamil; diaziquone; didemnin B; didox; diethylnorspermine; dihydro-5-azacytidine; dihydrotaxol, 9-; dioxamycin; diphenyl spiromustine; docetaxel; docosanol; dolasetron; doxifluridine; doxorubicin; droloxifene; dronabinol; duocarmycin SA; ebselen; ecomustine; edelfosine; edrecolomab; eflornithine; elemene; emitefur; epirubicin; epristeride; estramustine analogue; estrogen agonists; estrogen antagonists; etanidazole; etoposide phosphate; exemestane; fadrozole; fazarabine; fenretinide; filgrastim; finasteride; flavopiridol; flezelastine; fluasterone; fludarabine; fluorodaunorunicin hydrochloride; forfenimex; formestane; fostriecin; fotemustine; gadolinium texaphyrin; gallium nitrate; galocitabine; ganirelix; gelatinase inhibitors; gemcitabine; glutathione inhibitors; hepsulfam; heregulin; hexamethylene bisacetamide; hypericin; ibandronic acid; idarubicin; idoxifene; idramantone; ilmofosine; ilomastat; imatinib (e.g., Gleevec®); imiquimod; immunostimulant peptides; insulin-like growth factor-1 receptor inhibitor; interferon agonists; interferons; interleukins; iobenguane; iododoxorubicin; ipomeanol, 4-; iroplact; irsogladine; isobengazole; isohomohalicondrin B; itasetron; jasplakinolide; kahalalide F; lamellarin-N triacetate; lanreotide; leinamycin; lenograstim; lentinan sulfate; leptolstatin; letrozole; leukemia inhibiting factor; leukocyte alpha interferon; leuprolide+estrogen+progesterone; leuprorelin; levamisole; liarozole; linear polyamine analogue; lipophilic disaccharide peptide; lipophilic platinum compounds; lissoclinamide 7; lobaplatin; lombricine; lometrexol; lonidamine; losoxantrone; loxoribine; lurtotecan; lutetium texaphyrin; lysofylline; lytic peptides; maitansine; mannostatin A; marimastat; masoprocol; maspin; matrilysin inhibitors; matrix metalloproteinase inhibitors; menogaril; merbarone; meterelin; methioninase; metoclopramide; MIF inhibitor; mifepristone; miltefosine; mirimostim; mitoguazone; mitolactol; mitomycin analogues; mitonafide; mitotoxin fibroblast growth factor-saporin; mitoxantrone; mofarotene; molgramostim; Erbitux, human chorionic gonadotrophin; monophosphoryl lipid A+myobacterium cell wall sk; mopidamol; mustard anticancer agent; mycaperoxide B; mycobacterial cell wall extract; myriaporone; N-acetyldinaline; N-substituted benzamides; nafarelin; nagrestip; naloxone+pentazocine; napavin; naphterpin; nartograstim; nedaplatin; nemorubicin; neridronic acid; nilutamide; nisamycin; nitric oxide modulators; nitroxide antioxidant; nitrullyn; oblimersen (Genasense®); $O^6$-benzylguanine; octreotide; okicenone; oligonucleotides; onapristone; ondansetron; ondansetron; oracin; oral cytokine inducer; ormaplatin; osaterone; oxaliplatin; oxaunomycin; paclitaxel; paclitaxel analogues; paclitaxel derivatives; palauamine; palmitoylrhizoxin; pamidronic acid; panaxytriol; panomifene; parabactin; pazelliptine; pegaspargase; peldesine; pentosan polysulfate sodium; pentostatin; pentrozole; perflubron; perfosfamide; perillyl alcohol; phenazinomycin; phenylacetate; phosphatase inhibitors; picibanil; pilocarpine hydrochloride; pirarubicin; piritrexim; placetin A; placetin B; plasminogen activator inhibitor; platinum complex; platinum compounds; platinum-triamine complex; porfimer sodium; porfiromycin; prednisone; propyl bis-acridone; prostaglandin J2; proteasome inhibitors; protein A-based immune modulator; protein kinase C inhibitor; protein kinase C inhibitors, microalgal; protein tyrosine phosphatase inhibitors; purine nucleoside phosphorylase inhibitors; purpurins; pyrazoloacridine; pyridoxylated hemoglobin polyoxyethylene conjugate; raf antagonists; raltitrexed; ramosetron; ras farnesyl protein transferase inhibitors; ras inhibitors; ras-GAP inhibitor; retelliptine demethylated; rhenium Re 186 etidronate; rhizoxin; ribozymes; RII retinamide; rohitukine; romurtide; roquinimex; rubiginone B1; ruboxyl; safingol; saintopin; SarCNU; sarcophytol A; sargramostim; Sdi 1 mimetics; semustine; senescence derived inhibitor 1; sense oligonucleotides; signal transduction inhibitors; sizofuran; sobuzoxane; sodium borocaptate; sodium phenylacetate; solverol; somatomedin binding protein; sonermin; sparfosic acid; spicamycin D; spiromustine; splenopentin; spongistatin 1; squalamine; stipiamide; stromelysin inhibitors; sulfinosine; superactive vasoactive intestinal peptide antagonist; suradista; suramin; swainsonine; tallimustine; tamoxifen methiodide; tauromustine; tazarotene; tecogalan sodium; tegafur; tellurapyrylium; telomerase inhibitors; temoporfin; teniposide; tetrachlorodecaoxide; tetrazomine; thaliblastine; thiocoraline; thrombopoietin; thrombopoietin mimetic; thymalfasin; thymopoietin receptor agonist; thymotrinan; thyroid stimulating hormone; tin ethyl etiopurpurin; tirapazamine; titanocene bichloride; topsentin; toremifene; translation inhibitors; tretinoin; triacetyluridine; triciribine; trimetrexate; triptorelin; tropisetron; turosteride; tyrosine kinase inhibitors; tyrphostins; UBC inhibitors; ubenimex; urogenital sinus-derived growth inhibitory factor; urokinase receptor antagonists; vapreotide; variolin B; velaresol; veramine; verdins; verteporfin; vinorelbine; vinxaltine; vitaxin; vorozole; zanoterone; zeniplatin; zilascorb; and zinostatin stimalamer.

Specific second active agents include, but are not limited to, rituximab, oblimersen (Genasense®), remicade, docetaxel, celecoxib, melphalan, dexamethasone (Decadron®), steroids, gemcitabine, cisplatinum, temozolomide, etoposide, cyclophosphamide, temodar, carboplatin, procarbazine, gliadel, tamoxifen, topotecan, methotrexate, Arisa®, taxol, taxotere, fluorouracil, leucovorin, irinotecan, xeloda, CPT-11, interferon alpha, pegylated interferon alpha (e.g., PEG INTRON-A), capecitabine, cisplatin, thiotepa, fludarabine, carboplatin, liposomal daunorubicin, cytarabine, doxetaxol, paclitaxel, vinblastine, IL-2, GM-CSF, dacarbazine, vinorelbine, zoledronic acid, palmitronate, biaxin, busulphan, prednisone, bisphosphonate, arsenic trioxide, vincristine, doxorubicin (Doxil®), paclitaxel, ganciclovir, adriamycin, estramustine sodium phosphate (Emcyt®), sulindac, and etoposide.

In certain embodiments, the second active agent is etoposide, daunomycin, actinomycin D, mitomycin C, cisplatin, carboplatin, pemetrexed, methotrexate, Ara-C, 5-FU, wortmannin, gemcitabin, geldanamycin or a combination thereof.

In other embodiments, the second active agent is a supportive care agent. An example of supportive care agent is an antiemetic. Specific antiemetic agents include, but are not limited to, phenothiazines, butyrophenones, benzodiazapines, corticosteroids, serotonin antagonists, cannabinoids, and $NK_1$ receptor antagonists. Examples of phenothiazine antiemetics include, but are not limited to, prochlorperazine and trimethobenzamide. Examples of butyophenone antiemetic include, but are not limited to, haloperidol. Examples of benzodiazapine antiemetic include, but are not limited to, lorazepam. Examples of corticosteroid antiemetic include, but are not limited to, dexamethasone. Examples of serotonin antagonist antiemetic include, but are not limited to, ondansetron, granisetron, and dolasetron. Examples of cannabinoid antiemetic include, but are not limited to, dronabinol. Examples of $NK_1$ receptor antagonists include, but are not limited to, aprepitant. Doses and dosing regimens of antiemetic agents should depend on the specific indication being treated, age and condition of a patient, and severity of adverse effects, and may be adjusted accordingly by those of skill in the art. Examples of doses and dosing regimens can be found, for example, in *The Physician's Desk Reference*.

6.5.2 Exemplary Methods of Combination Therapy

In certain embodiments, the methods provided herein comprise administering SNS-595 in combination with one or more second active agents, and/or in combination with radiation therapy or surgery. The administration of SNS-595 and the second active agents to a patient can occur simultaneously or sequentially by the same or different routes of administration. The suitability of a particular route of administration employed for a particular active agent will depend on the active agent itself (e.g., whether it can be administered orally without decomposing prior to entering the blood stream) and the disease being treated. Recommended routes of administration for the second active agents are known to those of ordinary skill in the art. See, e.g., *Physicians' Desk Reference* (60$^{th}$ ed., 2006).

In one embodiment, the second active agent is administered intravenously or subcutaneously and once or twice daily in an amount of from about 1 to about 1,000 mg, from about 5 to about 500 mg, from about 10 to about 375 mg or from about 50 to about 200 mg. In one embodiment, the second active agent is rituximab, oblimersen (Genasense®), GM-CSF, G-CSF, EPO, taxotere, irinotecan, dacarbazine, transretinoic acid, topotecan, pentoxifylline, ciprofloxacin, dexamethasone, vincristine, doxorubicin, COX-2 inhibitor, IL2, IL8, IL18, IFN, Ara-C, vinorelbine or a combination thereof. In certain embodiments, the second active agent is etoposide, daunomycin, actinomycin D, mitomycin C, cisplatin, carboplatin, pemetrexed, methotrexate, Ara-C, 5-FU, wortmannin, geldanamycin, gemcitabin or a combination thereof.

In another embodiment, provided herein are methods of treating, preventing and/or managing hematologic malignancies, which comprise administering SNS-595 in conjunction with (e.g., before, during or after) conventional therapy including, but not limited to, surgery, immunotherapy, biological therapy, radiation therapy or other non-drug based therapy presently used to treat, prevent or manage cancer. Without being limited by theory, it is believed that SNS-595 may provide additive or synergistic effects when given concurrently with conventional therapy.

In certain embodiments, the second active agent is co-administered with SNS-595 or administered with 1-50 hours delay. In certain embodiments, SNS-595 is administered first followed by administration with the second active agent with 1-50 hours delay. In other embodiments, the second active agent is administered first followed by administration of SNS-595 with 1-50 hours delay. In some embodiment, the delay is 24 hours.

In one embodiment, SNS-595 can be administered in an amount of from about 1 to about 75 mg/m$^2$, 1 to about 60 mg/m$^2$, 1 to about 48 mg/m$^2$, 1 to about 24 mg/m$^2$, 1 to about 50 mg/m$^2$, about 1 to about 40 mg/m$^2$, about 1 to about 30 mg/m$^2$, about 3 to about 30 mg/m$^2$, about 3 to about 24 mg/m$^2$ alone or in combination with a second active agent disclosed herein, prior to, during, or after the use of conventional therapy.

In another embodiment, the methods provided herein comprise: a) administering to a patient in need thereof, a dose of about 1 mg/m$^2$ to 75 mg/m$^2$ of SNS-595 and b) administering a therapeutically effective amount of a supportive care agent.

In one embodiment, the second agent is an alkylating agent. In another embodiment, the alkylating agent is an alkyl sulfonate and the cancer being treated is leukemia or lymphoma. In another embodiment, the alkyl sulfonate is busulfan. In another embodiment, the alkyl sulfonate is busulfan and the therapeutically effective amount is a daily dose of at least 1 mg. In another embodiment, the alkyl sulfonate is busulfan and the therapeutically effective amount is a daily oral dose of between about 2 mg and 8 mg. In another embodiment, the alkyl sulfonate is busulfan and the therapeutically effective amount is a daily oral dose of between about 1 mg and about 3 mg.

In another embodiment, the alkylating agent is a nitrogen mustard and the cancer being treated is bladder cancer, breast cancer, Hodgkin's disease, leukemia, lung cancer, melanoma, ovarian cancer, or testicular cancer. In another embodiment, the nitrogen mustard is chlorambucil. In another embodiment, the nitrogen mustard is chlorambucil and the therapeutically effective amount is at least 0.1 mg/kg. In another embodiment, the nitrogen mustard is chlorambucil and the therapeutically effective amount is a daily oral dose of between about 0.1 mg/kg and about 0.2 mg/kg for three to six weeks. In another embodiment, the nitrogen mustard is chlorambucil and the therapeutically effective amount is a dose of 0.4 mg/kg every three to four weeks. In another embodiment, the nitrogen mustard is cyclophosphamide. In another embodiment, the nitrogen mustard is cyclophosphamide and the therapeutically effective amount is an intravenous dose of at least 10 mg/kg. In another embodiment, the nitrogen mustard is cyclophosphamide and the therapeutically effective amount is an intravenous dose between about 10 mg/kg and about 15 mg/kg every seven to ten days. In another embodiment, the nitrogen mustard is cyclophosphamide and the therapeutically effective amount is an oral daily dose between about 1 mg/kg and about 5 mg/kg. In another embodiment, the nitrogen mustard is melphalan. In another embodiment, the nitrogen mustard is melphalan and the therapeutically effective amount is a daily oral dose of at least 2 mg. In another embodiment, the nitrogen mustard is melphalan and the therapeutically effective amount is a daily oral dose of 6 mg for two to three weeks, no melphalan for two to four weeks and then a daily oral dose of between about 2 mg and about 4 mg. In another embodiment, the nitrogen mustard is melphalan and the therapeutically effective amount is a daily oral dose of 10 mg/m$^2$ for four days every four to six weeks.

In another embodiment, the alkylating agent is a nitrosourea and the cancer being treated is brain tumor, colorectal cancer, Hodgkin's disease, liver cancer, lung cancer, lymphoma, or melanoma. In another embodiment, the nitrosourea is carmustine. In another embodiment, the nitrosourea is carmustine and the therapeutically effective amount is at least 150 mg/m$^2$. In another embodiment, the nitrosourea is carmustine and the therapeutically effective amount is an intravenous dose between about 150 mg/m$^2$ and 200 mg/m$^2$ every six to eight weeks.

In another embodiment, the alkylating agent is a triazene and the cancer being treated is Hodgkin's disease, melanoma, neuroblastoma, or soft tissue sarcoma. In another embodiment, the triazene is dacarbazine. In another embodiment, the triazene is dacarbazine and the therapeutically effective amount is a daily intravenous dose of between about 2.0 mg/kg and about 4.5 mg/kg for ten days every four weeks. In another embodiment, the triazene is dacarbazine and the therapeutically effective amount is a daily intravenous dose of 250 mg/m$^2$ for five days every three weeks. In another embodiment, the triazene is dacarbazine and the therapeutically effective amount is an intravenous dose of 375 mg/m$^2$ every sixteen days. In another embodiment, the triazene is dacarbazine and the therapeutically effective amount is an intravenous dose of 150 mg/m$^2$ for five days every four weeks.

In another embodiment, the second agent is an anti-neoplastic antibiotic and the cancer being treated is bladder cancer, breast cancer, cervical cancer, head and neck cancer, Hodgkin's disease, leukemia, multiple myeloma, neuroblastoma, ovarian cancer, sarcoma, skin cancer, testicular cancer, or thyroid cancer. In another embodiment, the antibiotic is bleomycin. In another embodiment, the antibiotic is bleomycin and the therapeutically effective amount is at least 10 units/m$^2$. In another embodiment, the antibiotic is bleomycin and the therapeutically effective amount is an intravenous, subcutaneous, or intramuscular dose of between about 10 units/m$^2$ and about 20 units/m$^2$ weekly or twice weekly. In another embodiment, the antibiotic is dactinomycin. In another embodiment, the antibiotic is dactinomycin and the therapeutically effective amount is at least 0.01 mg/kg. In another embodiment, the antibiotic is dactinomycin and the therapeutically effective amount is a daily intravenous dose of between about 0.010 mg/kg and about 0.015 mg/kg for five days every three weeks. In another embodiment, the antibiotic is dactinomycin and the therapeutically effective amount is an intravenous dose of 2 mg/m$^2$ every three or four weeks. In another embodiment, the antibiotic is daunorubicin. In another embodiment, the antibiotic is daunorubicin and the therapeutically effective amount is at least 30 mg/m$^2$. In another embodiment, the antibiotic is daunorubicin and the therapeutically effective amount is a daily intravenous dose of between about 30 mg/m$^2$ and about 45 mg/m$^2$ for three days. In another embodiment, the antibiotic is a liposomal preparation of daunorubicin and the therapeutically effective amount is an intravenous dose of 40 mg/m$^2$ every two weeks. In another embodiment, the antibiotic is doxorubicin. In another embodiment, the antibiotic is doxorubicin and the therapeutically effective amount is at least 15 mg/m$^2$. In another embodiment, the antibiotic is doxorubicin and the therapeutically effective amount is an intravenous dose of between about 60 mg/m$^2$ and about 90 mg/m$^2$ every three weeks. In another embodiment, the antibiotic is doxorubicin and the therapeutically effective amount is a weekly intravenous dose of between about 15 mg/m$^2$ and about 20 mg/m$^2$. In another embodiment, the antibiotic is doxorubicin and the therapeutically effective amount is a cycle comprising a weekly intravenous dose of 30 mg/m$^2$ for two weeks followed by two weeks of no doxorubicin.

In another embodiment, the second agent is an anti-metabolite. In another embodiment, the anti-metabolite is a folate analog and the cancer being treated is breast cancer, head and neck cancer, leukemia, lung cancer, non-Hodgkin's lymphoma, or osteosarcoma. In another embodiment, the folate analog is methotrexate. In another embodiment, the folate analog is methotrexate and the therapeutically effective amount is at least 2.5 mg. In another embodiment, the folate analog is methotrexate and the therapeutically effective amount is a daily oral dose of between about 2.5 mg and about 5 mg. In another embodiment, the folate analog is methotrexate and the therapeutically effective amount is a twice-weekly dose of between about 5 mg/m$^2$ and about 25 mg/m$^2$. In another embodiment, the folate analog is methotrexate and the therapeutically effective amount is a weekly intravenous dose of 50 mg/m$^2$ every two to three weeks. In another embodiment, the folate analog is pemetrexed. In another embodiment, the folate analog is pemetrexed and the therapeutically effective amount is at least 300 mg/m$^2$. In another embodiment, the folate analog is pemetrexed and the therapeutically effective amount is an intravenous dose of between about 300 mg/m$^2$ and about 600 mg/m$^2$ every two or three weeks. In another embodiment, the folate analog is pemetrexed and the therapeutically effective amount is an intravenous dose of 500 mg/m$^2$ every three weeks.

In another embodiment, the anti-metabolite is a purine analog and the cancer being treated is colorectal cancer, leukemia, or myeloma. In another embodiment, the purine analog is mercaptopurine. In another embodiment, the purine analog is mercaptopurine and the therapeutically effective amount is at least 1.5 mg/kg. In another embodiment, the purine analog is mercaptopurine and the therapeutically effective amount is a daily oral dose of between about 1.5 mg/kg and about 5 mg/kg. In another embodiment, the purine analog is thioguanidine. In another embodiment, the purine analog is thioguanidine and the therapeutically effective amount is at least 2 mg/kg. In another embodiment, the purine analog is thioguanidine and the therapeutically effective amount is a daily oral dose of between about 2 mg/kg and about 3 mg/kg.

In another embodiment, the anti-metabolite is an adenosine analog and the cancer being treated is leukemia or lymphoma. In another embodiment, the adenosine analog is cladribine. In another embodiment, the adenosine analog is cladribine and the therapeutically effective amount is at least 0.09 mg/kg. In another embodiment, the adenosine analog is cladribine and the therapeutically effective amount is a daily intravenous dose of 0.09 mg/kg for seven days. In another embodiment, the adenosine analog is cladribine and the therapeutically effective amount is a daily intravenous dose of 4 mg/m$^2$ for seven days. In another embodiment, the adenosine analog is pentostatin. In another embodiment, the adenosine analog is pentostatin and the therapeutically effective amount is 4 mg/m$^2$. In another embodiment, the adenosine analog is pentostatin and the therapeutically effective amount is an intravenous dose of 4 mg/m$^2$ every other week. In another embodiment, the adenosine analog is pentostatin and the therapeutically effective amount is an intravenous dose of 4 mg/m$^2$ every three weeks.

In another embodiment, the anti-metabolite is a pyrimidine analog and the cancer being treated is bladder cancer, breast cancer, colorectal cancer, esophageal cancer, head and neck cancer, leukemia, liver cancer, lymphoma, ovarian cancer, pancreatic cancer, skin cancer, or stomach cancer. In another embodiment, the pyrimidine analog is cytarabine. In another embodiment, the pyrimidine analog is cytarabine and the therapeutically effective amount is at least 100 mg/m$^2$. In another embodiment the pyrimidine analog is cytarabine and the therapeutically effective amount is a daily intravenous dose of 100 mg/m$^2$ for seven days. In another embodiment, the pyrimidine analog is capecitabine. In another embodiment, the pyrimidine analog is capecitabine and the therapeutically effective amount is at least a daily dose of 2000 mg/m$^2$. In another embodiment, they pyrimidine analog is capecitabine and the therapeutically effective amount is a twice-daily oral dose of between about 1200 mg/m$^2$ and about 1300 mg/m$^2$ for 14 days. In another embodiment, the pyrimidine analog is capecitabine and the therapeutically effective amount is a three-week cycle wherein a twice-daily dose of about 1250 mg/m$^2$ is given for fourteen days followed by one week of rest. In another embodiment, the pyrimidine analog is fluorouracil. In another embodiment, the pyrimidine analog is fluorouracil and the therapeutically effective amount is at least 10 mg/kg. In another example, the pyrimidine analog is fluorouracil and the therapeutically effective amount is a daily intravenous dose of between about 300 mg/m$^2$ and about 500 mg/m$^2$ for at least three days. In another example, the pyrimidine analog is fluorouracil and the therapeutically effective amount is a daily intravenous dose of 12 mg/kg for three to five days. In another embodiment, the pyrimidine analog is fluorouracil and the therapeutically effective amount is a weekly intravenous dose of between about 10 mg/kg and about 15 mg/kg.

In another embodiment, the anti-metabolite is a substituted urea and the cancer being treated is head and neck cancer, leukemia, melanoma, or ovarian cancer. In another embodiment, the substituted urea is hydroxyurea. In another embodiment, the substituted urea is hydroxyurea and the therapeutically effective amount is at least 20 mg/kg. In another embodiment, the substituted urea is hydroxyurea and the therapeutically effective amount is an oral dose of 80 mg/kg every three days. In another embodiment, the substituted urea is hydroxyurea and the therapeutically effective amount is a daily oral dose of between about 20 mg/kg and about 30 mg/kg.

In another embodiment, the second agent is a platinum coordination complex and the cancer being treated is bladder cancer, breast cancer, cervical cancer, colon cancer, head and neck cancer, leukemia, lung cancer, lymphoma, ovarian cancer, sarcoma, testicular cancer, or uterine cancer. In another embodiment, the platinum coordination complex is carboplatin. In another embodiment, the platinum coordination complex is carboplatin and the therapeutically effective amount is at least 300 mg/m$^2$. In another embodiment, the platinum coordination complex is carboplatin and the therapeutically effective amount is at least 300 mg/m$^2$ every four weeks. In another embodiment, the platinum coordination complex is carboplatin and the therapeutically effective amount is 300 mg/m$^2$ every four weeks. In another embodiment, the platinum coordination complex is carboplatin and the therapeutically effective amount is at least 360 mg/m$^2$ every four weeks. In another embodiment, the platinum coordination complex is cisplatin. In another embodiment, the platinum coordination complex is cisplatin and the therapeutically effective amount is at least 20 mg/m$^2$. In another embodiment, the platinum coordination complex is cisplatin and the therapeutically effective amount is a daily intravenous dose of 20 mg/m$^2$ for four to five days every three to four weeks. In another embodiment, the platinum coordination complex is cisplatin and the therapeutically effective amount is an intravenous dose of 50 mg/m$^2$ every three weeks. In another embodiment, the platinum coordination complex is oxaliplatin. In another embodiment, the platinum coordination complex is oxaliplatin and the therapeutically effective amount is at least 75 mg/m$^2$. In another embodiment, the platinum coordination complex is oxaliplatin and the therapeutically effective amount is between about 50 mg/m$^2$ and about 100 mg/m$^2$. In another embodiment, the platinum coordination complex is oxaliplatin and the therapeutically effective amount is an IV infusion of between about 50 mg/m$^2$ and about 100 mg/m$^2$ every two weeks. In another embodiment, the platinum coordination complex is oxaliplatin and the therapeutically effective amount is an IV infusion of between about 80 mg/m$^2$ and about 90 mg/m$^2$ every two weeks. In another embodiment, the platinum coordination complex is oxaliplatin and the therapeutically effective amount is a two-hour IV infusion of 85 mg/m$^2$ every two weeks.

In another embodiment, the second agent is a topoisomerase II inhibitor and the cancer being treated is Hodgkin's disease, leukemia, small cell lung cancer, sarcoma, or testicular cancer. In another embodiment, the topoisomerase II inhibitor is etoposide. In another embodiment, the topoisomerase II inhibitor is etoposide and the therapeutically effective amount is at least 35 mg/m$^2$. In another embodiment, the topoisomerase II inhibitor is etoposide and the therapeutically effective amount is between about 50 mg/m$^2$ and about 100 mg/m$^2$. In another embodiment, the topoisomerase II inhibitor is etoposide and the therapeutically effective amount is an intravenous dose of between about 35 mg/m$^2$ and about 50 mg/m$^2$ a day at least three times in five days every three or four weeks. In another embodiment, the topoisomerase II inhibitor is etoposide and the therapeutically effective amount is an intravenous dose of between about 50 mg/m$^2$ and about 100 mg/m$^2$ a day at least three times in five days every three or four weeks. In another embodiment, the topoisomerase II inhibitor is etoposide and the therapeutically effective amount is an oral dose of 100 mg/m$^2$ a day at least three times in five days every three or four weeks. In another embodiment, the topoisomerase II inhibitor is teniposide. In another embodiment, the topoisomerase II inhibitor is teniposide and the therapeutically effective amount is at least 20 mg/m$^2$. In another embodiment, the topoisomerase II inhibitor is teniposide and the therapeutically effective amount is a weekly dose of 100 mg/m$^2$. In another embodiment, the topoisomerase II inhibitor is teniposide and the therapeutically effective amount is a twice weekly dose of 100 mg/m$^2$. In another embodiment, the topoisomerase II inhibitor is teniposide and the therapeutically effective amount is a daily dose of between about 20 mg/m$^2$ and about 60 mg/m$^2$ for five days. In another embodiment, the topoisomerase II inhibitor is teniposide and the therapeutically effective amount is a daily dose of between about 80 mg/m$^2$ and about 90 mg/m$^2$ for five days.

6.6 Pharmaceutical Compositions and Dosage Forms

The methods provided herein use pharmaceutical compositions containing SNS-595 and pharmaceutically acceptable carriers, such as diluents or adjuvants, or in combination with other active ingredient, such as another anti-cancer agent. In clinical practice SNS-595 may be administered by any conventional route, including but not limited to orally, parenterally, rectally or by inhalation (e.g. in the form of aerosols). In some embodiments, the compositions provided herein are acidic compositions (e.g., pH<4). Without being limited by a particular theory, acidic compositions provide the appropriate balance of increased solubility of SNS-595 and desirable pharmaceutical properties (e.g., increased patient comfort by causing less irritation at the delivery site).

In one embodiment, SNS-595 is administered by an IV injection. The compositions for parenteral administration can be emulsions or sterile solutions. Use may be made, as solvent or vehicle, of propylene glycol, a polyethylene glycol, vegetable oils, in particular olive oil, or injectable organic esters, for example ethyl oleate. These compositions can also contain adjuvants, in particular wetting, isotonizing, emulsifying, dispersing and stabilizing agents. Sterilization can be carried out in several ways, for example using a bacteriological filter, by radiation or by heating. They can also be prepared in the form of sterile solid compositions which can be dissolved at the time of use in sterile water or any other injectable sterile medium.

The compositions can also be aerosols. For use in the form of liquid aerosols, the compositions can be stable sterile solutions or solid compositions dissolved at the time of use in apyrogenic sterile water, in saline or any other pharmaceutically acceptable vehicle. For use in the form of dry aerosols intended to be directly inhaled, the active principle is finely divided and combined with a water-soluble solid diluent or vehicle, for example dextran, mannitol or lactose.

Pharmaceutical compositions can be used in the preparation of individual, single unit dosage forms. Pharmaceutical compositions and dosage forms comprise SNS-595 and one or more excipients.

Pharmaceutical compositions and dosage forms can also comprise one or more additional active ingredients. Examples of optional second, or additional, active ingredients are disclosed herein.

In certain embodiments, a composition provided herein is a pharmaceutical composition or a single unit dosage form. Pharmaceutical compositions and single unit dosage forms provided herein comprise a prophylactically or therapeutically effective amount of SNS-595, and typically one or more pharmaceutically acceptable carriers or excipients. The term "carrier" refers to a diluent, adjuvant (e.g., Freund's adjuvant (complete and incomplete)), excipient, or vehicle with which the therapeutic is administered. Such pharmaceutical carriers can be sterile liquids, such as water and oils, including those of petroleum, animal, vegetable or synthetic origin, such as peanut oil, soybean oil, mineral oil, sesame oil and the like. In certain embodiments, water is a carrier when the pharmaceutical composition is administered intravenously. Saline solutions and aqueous dextrose and glycerol solutions can also be employed as liquid carriers, particularly for injectable solutions. Examples of suitable pharmaceutical carriers are described in "Remington's Pharmaceutical Sciences" by E. W. Martin.

Typical pharmaceutical compositions and dosage forms comprise one or more excipients. Suitable excipients are well-known to those skilled in the art of pharmacy, and non limiting examples of suitable excipients include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like. Whether a particular excipient is suitable for incorporation into a pharmaceutical composition or dosage form depends on a variety of factors well known in the art including, but not limited to, the way in which the dosage form will be administered to a subject and the specific active ingredients in the dosage form. The composition or single unit dosage form, if desired, can also contain minor amounts of wetting or emulsifying agents, or pH buffering agents.

Further provided herein are pharmaceutical compositions and dosage forms that comprise one or more compounds that reduce the rate by which an active ingredient will decompose. Such compounds, which are referred to herein as "stabilizers," include, but are not limited to, antioxidants such as ascorbic acid, pH buffers, or salt buffers.

The pharmaceutical compositions and single unit dosage forms can take the form of solutions, suspensions, emulsion, powders and the like. Such compositions and dosage forms will contain a prophylactically or therapeutically effective amount of a prophylactic or therapeutic agent, in certain embodiments, in purified form, together with a suitable amount of carrier so as to provide the form for proper administration to the subject. The formulation should suit the mode of administration. In one embodiment, the pharmaceutical compositions or single unit dosage forms are sterile and in suitable form for administration to a subject, such as an animal subject, or a mammalian subject, and such as a human subject.

A pharmaceutical composition provided herein is formulated to be compatible with its intended route of administration. Examples of routes of administration include, but are not limited to, parenteral, e.g., intravenous, intradermal, subcutaneous, intramuscular, subcutaneous, inhalation, intranasal, transdermal, topical, transmucosal, intra-tumoral, intra-synovial and rectal administration. In a specific embodiment, the composition is formulated in accordance with routine procedures as a pharmaceutical composition adapted for intravenous, subcutaneous, intramuscular, intranasal or topical administration to human beings. In an embodiment, a pharmaceutical composition is formulated in accordance with routine procedures for subcutaneous administration to human beings. Typically, compositions for intravenous administration are solutions in sterile isotonic aqueous buffer. Where necessary, the composition may also include a solubilizing agent and a local anesthetic such as lignocamne to ease pain at the site of the injection.

Examples of dosage forms include, but are not limited to: liquid dosage forms suitable for parenteral administration to a subject; and sterile solids (e.g., crystalline or amorphous solids) that can be reconstituted to provide liquid dosage forms suitable for parenteral administration to a subject.

The composition, shape, and type of dosage forms provided herein will typically vary depending on their use. For example, a dosage form used in the initial treatment of disease may contain larger amounts of one or more of the active ingredients it comprises than a dosage form used in the maintenance treatment of the same infection. Similarly, a parenteral dosage form may contain smaller amounts of one or more of the active ingredients it comprises than an oral dosage form used to treat the same disease or disorder. These and other ways in which specific dosage forms encompassed herein will vary from one another will be readily apparent to those skilled in the art. See, e.g., *Remington's Pharmaceutical Sciences*, 20th ed., Mack Publishing, Easton Pa. (2000).

Generally, the ingredients of compositions provided herein are supplied either separately or mixed together in unit dosage form, for example, as a dry lyophilized powder or water free concentrate in a hermetically sealed container such as an ampoule or sachette indicating the quantity of active agent. Where the composition is to be administered by infusion, it can be dispensed with an infusion bottle containing sterile pharmaceutical grade water or saline. Where the composition is administered by injection, an ampoule of sterile water for injection or saline can be provided so that the ingredients may be mixed prior to administration.

Typical dosage forms provided herein comprise SNS-595 within the range of about 1 mg/m$^2$ to about 75 mg/m$^2$ per day, or weekly, given as a single once-a-day dose in the morning or as divided doses throughout the day taken with food. Particular dosage forms provided herein have about 1, 3, 6, 9, 12, 15, 18, 21, 24, 27 or 30 mg/m$^2$ of SNS-595.

6.6.1 Parenteral Dosage Forms

Parenteral dosage forms can be administered to patients by various routes including, but not limited to, subcutaneous, intravenous (including bolus injection), intramuscular, and intraarterial. Because their administration typically bypasses patients' natural defenses against contaminants, parenteral dosage forms are preferably sterile or capable of being sterilized prior to administration to a patient. Examples of parenteral dosage forms include, but are not limited to, solutions ready for injection, dry products ready to be dissolved or suspended in a pharmaceutically acceptable vehicle for injection, suspensions ready for injection, and emulsions.

Suitable vehicles that can be used to provide parenteral dosage forms are well known to those skilled in the art. Examples include, but are not limited to: Water for Injection USP; aqueous vehicles such as, but not limited to, Sodium Chloride Injection, Ringer's Injection, Dextrose Injection, Dextrose and Sodium Chloride Injection, and Lactated Ringer's Injection; water-miscible vehicles such as, but not limited to, ethyl alcohol, polyethylene glycol, and polypropylene glycol; and non-aqueous vehicles such as, but not limited to, corn oil, cottonseed oil, peanut oil, sesame oil, ethyl oleate, isopropyl myristate, and benzyl benzoate.

Compounds that increase the solubility of one or more of the active ingredients disclosed herein can also be incorporated into the parenteral dosage forms. For example, cyclodextrin and its derivatives can be used to increase the solubility of active ingredients. See, e.g., U.S. Pat. No. 5,134,127, which is incorporated herein by reference.

6.6.2 Topical and Mucosal Dosage Forms

In certain embodiments, provided herein are transdermal, topical, and mucosal dosage forms. Transdermal, topical, and mucosal dosage forms provided herein include, but are not limited to, ophthalmic solutions, sprays, aerosols, creams, lotions, ointments, gels, solutions, emulsions, suspensions, or other forms known to one of skill in the art. See, e.g., *Remington's Pharmaceutical Sciences*, 20th ed., Mack Publishing, Easton Pa. (2000); and Introduction to Pharmaceutical Dosage Forms, 4th ed., Lea & Febiger, Philadelphia (1985). Dosage forms suitable for treating mucosal tissues within the oral cavity can be formulated as mouthwashes or as oral gels. Further, transdermal dosage forms include "reservoir type" or "matrix type" patches, which can be applied to the skin and worn for a specific period of time to permit the penetration of a desired amount of active ingredients.

Suitable excipients (e.g., carriers and diluents) and other materials that can be used to provide topical and mucosal dosage forms encompassed herein are well known to those skilled in the pharmaceutical arts, and depend on the particular tissue to which a given pharmaceutical composition or dosage form will be applied. With that fact in mind, typical excipients include, but are not limited to, water, acetone, ethanol, ethylene glycol, propylene glycol, butane-1,3-diol, isopropyl myristate, isopropyl palmitate, mineral oil, and mixtures thereof to form solutions, emulsions or gels, which are non-toxic and pharmaceutically acceptable. Moisturizers or humectants can also be added to pharmaceutical compositions and dosage forms if desired. Examples of such additional ingredients are well known in the art. See, e.g., *Remington's Pharmaceutical Sciences*, 20th ed., Mack Publishing, Easton Pa. (2000).

The pH of a pharmaceutical composition or dosage form may also be adjusted to improve delivery of one or more active ingredients. Similarly, the polarity of a solvent carrier, its ionic strength, or tonicity can be adjusted to improve delivery. Compounds such as stearates can also be added to pharmaceutical compositions or dosage forms to advantageously alter the hydrophilicity or lipophilicity of one or more active ingredients so as to improve delivery. In this regard, stearates can serve as a lipid vehicle for the formulation, as an emulsifying agent or surfactant, and as a delivery-enhancing or penetration-enhancing agent. Different salts, hydrates or solvates of the active ingredients can be used to further adjust the properties of the resulting composition.

7. EXAMPLES

Certain embodiments provided herein are illustrated by the following non-limiting example.

Example 1

Pharmaceutical Composition Suitable for Injection or Intravenous Infusion

Acidic compositions (<pH 4) provided the appropriate balance of increased solubility of SNS-595 and desirable pharmaceutical properties (e.g. increased patient comfort by causing less irritation at the delivery site). An illustrative example of a suitable composition comprises: 10 mg SNS-595 per mL of aqueous solution of 4.5% sorbitol that is adjusted to pH 2.5 with methanesulfonic acid. One protocol for making such a solution includes the following for making a 100 mg/10 mL presentation: 100 mg of SNS-595 and 450 mg D-sorbitol are added to distilled water; the volume is brought up to a volume of 10 mL; and the pH of the resulting solution is adjusted to 2.5 with methanesulfonic acid. The resulting composition is also suitable for lyophilization. The lyophilized form is then reconstituted with sterile water to the appropriate concentration prior to use.

Example 2

Clinical Trial Data of SNS-595 in Patients with Advanced Solid Tumor Cancer The safety and efficacy of SNS-595 were investigated in two dose-escalating studies. As demonstrated below, SNS-595 provides good safety profiles and evidence of anti-tumor activity in patients with refractory solid tumors.

SNS-595 was administered to patients with advanced solid cancers as an IV infusion over 10 minutes on 2 schedules. In the first schedule (A), a weekly dose of SNS-595 was administered for three weeks followed by at least 7 days off (qwk× 3). In the second schedule (B), a dose of SNS-595 was administered once every three weeks (q3wk).

In both schedules, the starting dose of SNS-595 was 3 mg/m$^2$, and doses were escalated by sequential cohorts of 3. The doses were doubled until the first related adverse event at or above Grade 2 or until the first abnormal lab value. The doses were then escalated by a modified Fibonacci schema.

No other therapy, for example mitomycin-C, BCNU, nitrosourea drugs or MAb therapy, was given within 42 days of the study.

In study A, 21 patients (9 male, 12 female) were treated in 6 cohorts (dose range 3-24 mg/m$^2$/wk). In study B, 41 (25 male, 16 female) patients were treated in 9 cohorts (dose range 3-75 mg/m$^2$/wk). The median ages were 61 yrs (Study A) and 59 yrs (Study B), sex 12F/9M (Study A), 16F/25M (Study B), all patients had baseline European Cooperative Oncology Group Performance Status (ECOG PS) 0-2. Patient eligibility included refractory solid tumors and adequate organ function. Table 1 provides patient demographics in both the studies.

TABLE 1

| Patient demographics | | | |
|---|---|---|---|
| | qwk x3 | q3wk | total |
| n (# treated) | 21 | 41 | 62 |
| Sex | | | |
| Male | 9 (43%) | 25 (61%) | 34 (55%) |
| Female | 12 (57%) | 16 (39%) | 28 (45%) |
| Ethnic Background | | | |
| Asian | 2 (10%) | 1 (2%) | 3 (5%) |
| Black | 2 (10%) | 4 (10%) | 6 (10%) |
| Hispanic | 0 | 1 (2%) | 1 (2%) |
| Native Hawaiian/ Pacific Islander | 0 | 2 (5%) | 2 (3%) |
| White | 17 (81%) | 33 (81%) | 50 (81%) |

TABLE 1-continued

Patient demographics

|  | qwk x3 | q3wk | total |
|---|---|---|---|
| Age (yrs) | | | |
| Mean | 59.3 | 58.5 | 58.8 |
| Median | 61 | 59 | 60 |
| Range | 19-81 | 33-79 | 19-81 |
| Previous Therapies | | | |
| MP | 9 (43%) | 17 (41%) | 26 (42%) |
| HP | 12 (57%) | 24 (59%) | 36 (58%) |

Table 2 provides a list of tumor types treated in both the studies.

TABLE 2

Tumor types treated

|  | qwk x3 | q3wk | total |
|---|---|---|---|
| n (# treated) | 21 | 41 | 62 |
| Ovarian | 1 | 9 | 10 |
| Colon | 3 | 6 | 9 |
| NSCLC | 0 | 6 | 6 |
| Pancreas | 3 | 2 | 5 |
| Renal | 1 | 4 | 5 |
| Melanoma | 1 | 3 | 4 |
| Adeno CA (origin unk) | 0 | 3 | 3 |
| Breast | 2 | 0 | 2 |
| Sarcomas | 0 | 3 | 3 |
| Cholangiocarcinoma | 1 | 1 | 2 |
| Mesothelioma | 2 | 0 | 2 |
| Neuroendocrine | 1 | 1 | 2 |
| Bladder | 0 | 1 | 1 |
| Leiomyosarcoma | 1 | 1 | 2 |
| Liposarcoma | 1 | 0 | 1 |

TABLE 2-continued

Tumor types treated

|  | qwk x3 | q3wk | total |
|---|---|---|---|
| Müllerian | 0 | 1 | 1 |
| Nasopharyngeal | 1 | 0 | 1 |
| Salivary Gland | 1 | 0 | 1 |
| Small Cell Lung Cancer | 1 | 0 | 1 |
| Spindle Cell Carcinoma | 1 | 0 | 1 |

Figure 1:
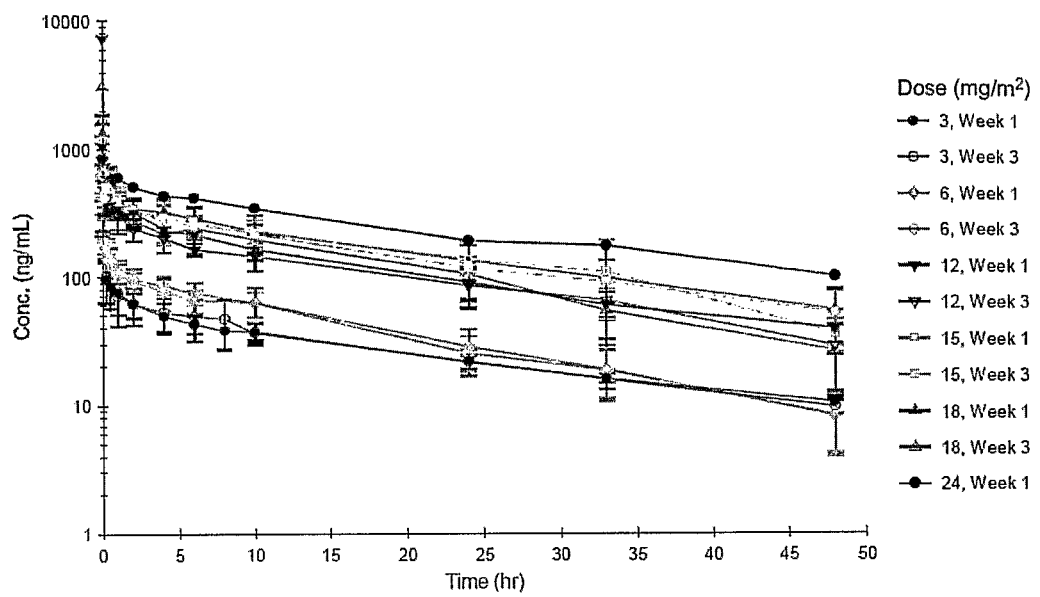
FIG. 1 depicts the plasma concentrations of SNS-595 over time among the various patient cohorts dosed in the qwk×3 schedule.

For patients dosed according to schedule A, PK samples were collected on treatment Days 1 and 15 and were assayed using noncompartmental analysis. Plasma SNS-595 concentrations were determined using a validated LC-MS/MS assay. AUC (area under curve) increased proportionally with dose and mean $AUC_{Inf}$ and ranged between 1.7 and 15 µg*hr/ml, respectively, for 3 to 24 mg/m² dose levels. The terminal half-life is approximately 19 hours. No evidence of drug dependent alterations in pharmacokinetic parameters was observed after 3 weekly doses. FIG. 1 depicts the plasma concentrations of SNS-595 over time among the various patient cohorts. Table 3 provides the pharmacokinetic parameters for patents dosed according to schedule A.

TABLE 3

Average of Week 1 and Week 3 Pharmacokinetic Parameters

| Dose (mg/m²) | n (Week 1, Week 3) | T ½ hr | $C_{max}$ µg/ml | $AUC_{inf}$ µg · hr/ml | $Cl_{obs}$ L/hrm² | $V_{ssobs}$ L/m² |
|---|---|---|---|---|---|---|
| 3 | 7 (4, 3) | 23.3 ± 7.2 | 0.577 ± 0.795 | 1.71 ± 0.20 | 1.77 ± 0.23 | 52.7 ± 18.2 |
| 6 | 6 (3, 3) | 13.5 ± 2.2 | 0.531 ± 0.28 | 2.09 ± 0.53 | 3.05 ± 0.84 | 51.0 ± 8.22 |
| 12 | 6 (3, 3) | 19.9 ± 5.3 | 1.84 ± 2.7 | 6.81 ± 1.68 | 1.87 ± 0.53 | 44.6 ± 8.53 |
| 15 | 10 (5, 5) | 26.4 ± 15.2 | 0.865 ± 0.318 | 10.8 ± 4.7 | 1.59 ± 0.56 | 43.8 ± 7.90 |
| 18 | 6 (4, 2) | 15.8 ± 4.2 | 1.69 ± 0.83 | 8.50 ± 2.86 | 2.36 ± 0.88 | 47.19 ± 8.06 |
| 24 | 1 (1, 0) | 24.2 | 0.6 | 15.2 | 1.58 | 50.0 |
| Average | | 18.5 ± 4.6 | — | — | 2.22 ± 0.58 | 47.6 ± 10.7 |
| Range | | 10-33 | 0.6-1.8 | 2-15 | 1.4-4.3 | 30-75 |

For patients dosed according to schedule B, pharmacokinetic parameters were evaluated in 36 patients (21 heavily pretreated and 15 minimally pretreated) after a single dose of 3 to 75 mg/m². Clearance (CL), volume of distribution, and terminal half-life ($T_{1/2}$) remained unchanged across all patients up to 48 mg/m². In minimally pretreated patients, PK parameters remained unchanged up to 75 mg/m². CL was 2.2 L/hr/m2 (range of 1.0-3.8 L/hr/m²), the volume of distribution was 53 L/m² (range of 31-76 L/m²), and the $T_{1/2}$ was approximately 21 hr (range of 13-49 hr). Exposure was similar for both heavily and minimally pretreated patients and increased linearly with doses up to 48 mg/m². Exposure for minimally pretreated patients showed a greater than dose linear AUC (area under the curve) at the 60 mg/m² dose level. Table 4 shows pharmacokinetic parameters for patients dosed according to schedule B.

TABLE 4

Week 3 Pharmacokinetic Parameters

| Dose (mg/m$^2$) | n | T ½ hr | C$_{max}$ μg/ml | AUC$_{inf}$ μg · hr/ml | Cl$_{obs}$ L/hrm$^2$ | V$_{ssobs}$ L/m$^2$ |
|---|---|---|---|---|---|---|
| 3 | 3 | 16.4 ± 4.8 | 0.139 ± 0.08 | 1.14 ± 0.26 | 2.72 ± 0.58 | 57.7 ± 8.7 |
| 6 | 2 | 22.2 ± 1.9 | 0.347 ± 0.22 | 3.04 ± 0.32 | 1.98 ± 0.21 | 59.8 ± 0.5 |
| 12 | 3 | 18.0 ± 4.1 | 2.25 ± 1.07 | 6.32 ± 0.22 | 1.90 ± 0.07 | 45.2 ± 8.9 |
| 24 | 3 | 15.7 ± 3.2 | 2.70 ± 2.57 | 12.63 ± 0.86 | 1.91 ± 0.13 | 40.7 ± 8.8 |
| 36 | 6 | 22.5 ± 4.2 | 3.38 ± 1.92 | 18.05 ± 0.73 | 2.00 ± 0.08 | 61.4 ± 12.8 |
| 48 | 10 | 26.4 ± 13.1 | 3.08 ± 1.92 | 29.41 ± 11.34 | 1.92 ± 0.91 | 58.8 ± 14.5 |
| 60 | 8 | 25.0 ± 17.9 | 3.86 ± 1.68 | 40.71 ± 23.67 | 1.88 ± 0.88 | 48.0 ± 7.3 |
| 75 | 4 | 25.0 ± 4.9 | 5.05 ± 1.72 | 46.09 ± 6.12 | 1.65 ± 0.22 | 56.3 ± 9.4 |
| Average | | 21.3 ± 5.3 | — | — | 2.0 ± 0.4 | 53.2 ± 4.1 |
| Range | | 13-56 | 0.1-5 | 1-46 | 1-3.8 | 31-76 |

In study A, pharmacokinetics were assessed on Days 1 and 15 (after the first and third doses). As seen in Table 5, SNS-595 shows highly reproducible pharmacokinetics and low inter-patient variability. No accumulation or change in pharmacokinetic parameters was observed after repeat dosing. Exposure increased linearly over an 8-fold dose range (1.6-15 μg·hr/mL), clearance (CL), volume of distribution (Vss) and T$_{1/2}$ averaged 2 L/hr/m$^2$, 48 L/m$^2$, 19 hr, respectively, and did not change from Day 1 to 15.

In study B, pharmacokinetics were assessed on Day 1 after the first dose; exposure increased linearly over the 24-fold dose range (1.1-46 μg·hr/mL), CL, Vss, and T$_{1/2}$ averaged 2 L/hr/m$^2$, 53 L/m$^2$, and 21 hrs, respectively.

Average pharmacokinetic parameters are provided for both studies in Table 5.

TABLE 5

Average of wk 1 and wk 3 Pharmacokinetic Parameters

| | qwk x3, Week 1 | qwk x3, Week 3 | q3wk |
|---|---|---|---|
| n | 20 | 16 | 39 |
| Dose Range (mg/m$^2$) | 3-24 | 3-18 | 3-75 |
| AUCinf Range (μg · hr/mL) | 2-15 | 2-7 | 1-46 |
| T$_{1/2}$ (hr) ± SD | 22 ± 11 | 19 ± 8 | 21 ± 5 |
| Clobs (L/hr/m2) ± SD | 1.9 ± 0.7 | 2.2 ± 0.9 | 2.0 ± 0.4 |
| Vss (L/m2) ± SD | 48 ± 12 | 47 ± 8 | 53 ± 4 |

FIG. 11 demonstrates dose linearity in Studies A and B.

Table 6 provides data for hematologic effects observed in the studies.

TABLE 6

Hematologic Effects

| Dose | Schedule | n | # ANC ≤500 | # Febrile Neut. |
|---|---|---|---|---|
| 3 mg/m$^2$ | qwk x3 | 4 | 0 | 0 |
| 6 mg/m$^2$ | qwk x3 | 3 | 0 | 0 |
| 12 mg/m$^2$ | qwk x3 | 3 | 0 | 0 |
| 15 mg/m$^2$ | qwk x3 | 6 | 0 | 0 |
| 18 mg/m$^2$ | qwk x3 | 4 | 0 | 0 |
| 24 mg/m$^2$ | qwk x3 | 1 | 0 | 0 |
| 3 mg/m$^2$ | q3wk | 3 | 0 | 0 |
| 6 mg/m$^2$ | q3wk | 3 | 0 | 0 |
| 12 mg/m$^2$ | q3wk | 3 | 0 | 0 |
| 24 mg/m$^2$ | q3wk | 3 | 0 | 0 |
| 36 mg/m$^2$ | q3wk | 6 | 0 | 0 |
| 48 mg/m$^2$ | q3wk | 6 | 1 | 0 |
| 48 mg/m$^2$ (HP) | q3wk | 5 | 2 | 0 |
| 60 mg/m$^2$ | q3wk | 8 | 3 | 1 |
| 75 mg/m$^2$ | q3wk | 4 | 0 | 0 | n = number of patients in cohort
*Absolute Neutrophil Count (cells/μL) ≤500 lasting more than 7 days In the description herein, the term "maximum tolerated dose" or "MTD" refers to the dose level below a dose of SNS-595 where ≥2 of 6 patients experienced dose limiting toxicity (DLT). The term, "heavily pretreated" or "HP" patient refers to a patient who has previously received >6 courses of an alkylating agent, chemotherapy or >2 courses of platinum, mitomycin-C or any nitrosourea, or XRT to >25% of bone. The term, "minimally pretreated" or "MP" patient refers to a patient who does not fulfill the HP definition. (See, Tolcher et al, *JCO* 2001; 19:2937-2947).

As used herein, dose limiting toxicity (DLT) refers to absolute neutrophil count (ANC) ≤500 for ≥7 days or febrile neutropenia or platelet nadir <25000 or bleeding or non-hematologic adverse events (AE) ≥Grade 3 (as described in Common Terminology Criteria for Adverse Events *Version 3.0* (CTCAE v3.0)), wherein adverse events required >14 days dose delay.

Tables 7-9 provide safety data for both the studies.

TABLE 7

Frequent (>10% patients) adverse events

| Body System preferred term | qwk x3 n = 21 | q3wk n = 41 | total n = 62 |
|---|---|---|---|
| Cardiac Disorders | | | |
| edema peripheral | | 0/4* | |
| Gastrointestinal Disorders | | | |
| abd pain | 1/5 | 0/8 | 1/13 (8%) |
| constipation | 0/7 | 1/12 | 1/19 (5%) |
| diarrhea | 0/4 | 0/8 | 0/12 (0%) |

TABLE 7-continued

Frequent (>10% patients) adverse events

| Body System | qwk x3 | q3wk | total |
|---|---|---|---|
| nausea | 0/8 | 2/26 | 2/34 (6%) |
| vomiting | 0/5 | 1/17 | 1/22 (5%) |
| General Conditions | | | |
| fatigue | 1/4 | 1/13 | 2/17 (12%) |
| Metabolism & Nutrition Disorders | | | |
| anorexia | | 0/7 | 0/7 (0%) |
| Musculoskeletal & Connective Tissue Disorders | | | |
| backpain | | 0/7 | 0/7 (0%) |
| pain in extremity | 0/5 | | |
| Nervous System Disorders | | | |
| dizziness | | 0/6 | 0/6 (0%) |
| headache | 0/3 | 0/8 | 0/11 (0%) |
| Skin & Subcutaneous Tissue Disorders | | | |
| alopecia | | 0/8 | 0/8 (0%) |

*no. patients with Grade ≥ 3/no. patients with any Grade

TABLE 8

Hematologic Effects

| | Qwk x3 | q3wk | total |
|---|---|---|---|
| | n = 21 | n = 41 | n = 62 |
| Grade 4 Neutropenia (ANC < 500/mm³) | 0 | 10 (24%) | 10 (16%) |
| Febrile Neutropenia | 0 | 1 (2%) | 1 (2%) |
| Grade 4 Thrombocytopenia (<25,000/mm³) | 0 | 2 (5%) | 2 (3%) |

TABLE 9

Serious Adverse Events (SAE) Possibly Related to Study Drug

| SAE preferred term 1 patient for each of the following | CTCAE v3.0 Grade | |
|---|---|---|
| | qwk x3 | q3wk |
| Sepsis | not observed | Grade 3 |
| Vomiting | not observed | Grade 3 |
| Pneumonia | not observed | Grade 3 |
| Febrile Neutropenia | not observed | Grade 2 |

TABLE 9-continued

Serious Adverse Events (SAE) Possibly Related to Study Drug

| SAE preferred term 1 patient for each of the following | CTCAE v3.0 Grade | |
|---|---|---|
| | qwk x3 | q3wk |
| Pancytopenia | not observed | Grade 4 |
| Thrombosis | not observed | Grade 2 |

As seen from the data, neutropenia was the dose limiting toxicity (DLT) for both studies. In study A, the dose-limiting toxicity (DLT) of neutropenia was seen in the first patient at the 24 mg/m² level. 5 patients were then treated at 18 mg/m² where 2 developed DLT of neutropenia. In study B, for the heavily pretreated patients, the dose limiting toxicity (DLT) consisting of Grade 4 neutropenia for greater than 7 days was observed at 60 mg/m². For minimally pretreated patients, one dose limiting toxicity was seen at a dose of 75 mg/m².

The MTD for study A was 15 mg/m²; the MTD for study B was 48 mg/m² for heavily pretreated (HP) patients and 60 mg/m² for minimally pretreated (MP) patients.

For both studies two patients had grade 4 thrombocytopenia; non-hematologic toxicities were mostly grade 1/2 without dose-limiting gastrointestinal toxicity or neurotoxicity.

Table 10 provides evidence of clinical activity of SNS-595 for both the studies. For study A, best responses included one patient that achieved partial response (PR) and six that achieved stable disease SD (range 16-24 wks). For study B, best responses included one PR and 11 SD (range 18-58 wks). Table 11 provides details of Partial/Minor Responses (PR/MR) in both the studies.

TABLE 10

Evidence of Clinical Activity

| Initial Dosage (mg/m²) | Scheduled | Tumor Type | Weeks on Therapy | Best Response |
|---|---|---|---|---|
| 6 | qwk x3 | Renal Cell | 16 | SD |
| 12 | qwk x3 | Leiomyosarcoma | 16 | SD |
| | | Melanoma | 16 | SD |
| 15 | qwk x3 | Mesothelioma | 28 | PR |
| | | Mesothelioma | 18 | SD |
| | | Nasopharyngeal | 16 | SD |
| 24 | qwk x3 | Salivary Gland | 24 | SD |
| 3 | q3wk | Lung | 18 | SD |
| 6 | q3wk | Renal Cell | 18 | SD |
| 12 | q3wk | Lung | 53 | SD |
| 24 | q3wk | Adenocarcinoma (unknown origin) | 18 | SD |
| 36 | q3wk | Ovarian | 18 | SD |
| | | Colon | 33 | SD |
| 48 | q3wk | Ovarian | 24 | PR |
| | | Ovarian | 30 | SD |
| | | Lung | 46 | SD |
| 60 | q3wk | Ovarian | 33 | SD |
| | | Neuroendocrine | 58 | SD |
| 75 | q3wk | Müllerian | 46 | SD |

TABLE 11

Details of Partial/Minor Responses (PR/MR)

| Best Response | Tumor | Criterion | Baseline | C2 | C4 | C6 |
|---|---|---|---|---|---|---|
| PR | Ovarian | CA125 (U/mL) | 467 | 272 | 176 | 120 |
| | | P-aortic node (cm) | 1.7 | 1.6 | 1.5 | 1.3 |
| | | Aortic node (cm) | 2.4 | 2.0 | 2.2 | 2.0 |
| | | Iliac node (cm) | 5.5 | 5.0 | 4.7 | 3.9 |
| SD (MR) | Nasopharyngeal | Rt upper lobe nodule 1 (cm) | 2.3 | 1.5 | — | — |
| | | Rt upper lobe nodule 2 (cm) | 1.5 | 1.3 | — | — |
| | | Left upper lobe nodule (cm) | 1.1 | 1.0 | — | — |
| | | Lingular nodule | 1.6 | 1.5 | — | — |
| SD (MR) | Ovarian | CA125 (U/mL) | 567 | 811 | 419 | 274 |
| | | Liver met (cm) | 7.4 | 6.9 | 5.7 | 5.7 |
| | | Aortic node (cm) | 1.7 | 1.5 | 1.2 | 1.8 |
| | | P-aortic node (cm) | 1.8 | 1.1 | 1.1 | 1.2 |
| SD (MR) | Ovarian | CA125 (U/mL) | 50 | 18 | 16 | 15 |
| | | Rectosigmoid (cm) | 2.5 | 0.0 | 0.0 | 0.0 |
| | | 3 mets unchanged | | | | |
| SD (MR) | Müllerian | RML Lung (cm) | 3.9 | 3.9 | 3.7 | 2.4 |
| | | RUL Lung (cm) | 4.7 | 4.5 | 4.5 | 5.0 |
| | | RMLL Lung (cm) | 2.5 | 2.5 | 2.5 | 2.6 |

Significantly, SNS-595 shows evidence of clinical activity in patients with advanced solid cancers including two patients that achieved partial responses and seventeen patients that achieved stable disease for over sixteen weeks.

As seen from the data, SNS-595 was well tolerated and showed clinical activity with both once a week and once three weeks dosing. The dose limiting toxicity was non-cumulative neutropenia. SNS-595 demonstrated predictable pharmacokinetics with low inter- and intra patient variability. No change in pharmacokinetic parameters was observed after repeat dosing.

Useful doses for treatment of solid tumors in patients in need thereof include 48 mg/m$^2$ once in three weeks and 15 mg/m$^2$ weekly as described in this example.

Example 3

High Content Screening and Microscopy

Cells were plated as sub-confluent populations and allowed to grow for 36 hours. Cells were then treated with the compound at the given concentration for the given time period. Cells were fixed using 4% formaldehyde and permeabilized with 0.1% triton. Cells were exposed to primary antibodies for 1 hour at 25° C. at a 1:100 dilution in 10% FBS/PBS (anti-pATM—Chemicon, anti-gH2AX-Cell Signaling Technology). Cells were exposed to secondary antibodies for 1 hour at 25° C. at a 1:100 dilution in 10% FBS/PBS. Hoechst staining was carried out in 10% FBS/PBS at 500 ng/ml concentrations. High content screening was carried out on a Cellomics Arrayscan instrument using the Spot Detector algorithm.

Figure 2:
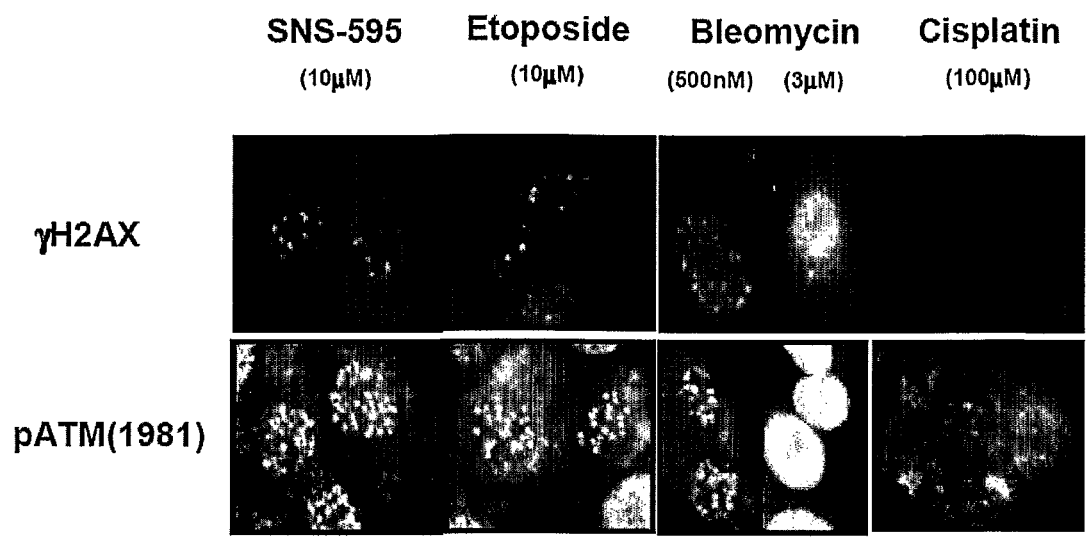
FIG. 2 illustrates nuclear foci formation in HCT116 cells after treatment with SNS-595, etoposide, bleomycin and cisplatin.

FIG. 2 shows HCT116 cells that were dosed with various compounds for 6 hour time periods. Cells were then fixed and analyzed for protein phosphorylation state (gH2AX images obtained using a fluorescence microscope, pATM images obtained with the ArrayScan VTi). As seen in the figure, SNS-595 treatment leads to nuclear foci formation.

Figure 3:
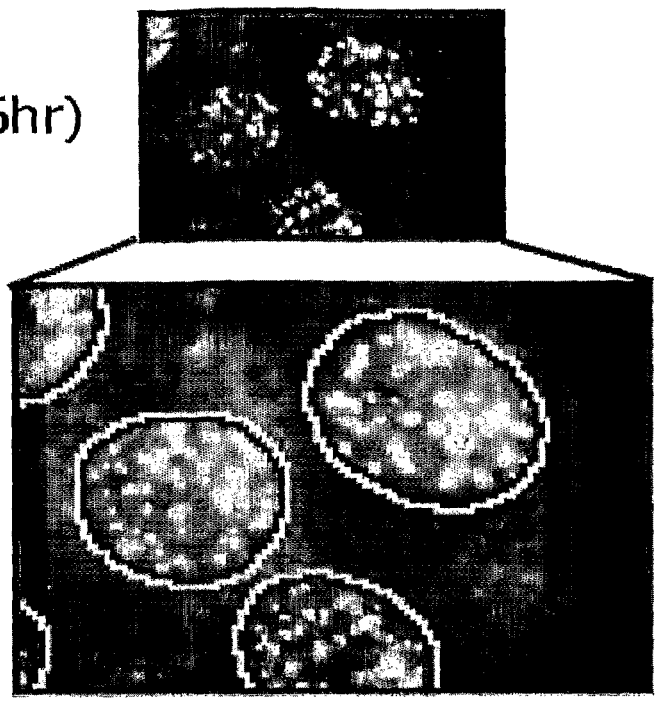
FIG. 3 depicts foci quantitation by measuring foci fluorescent intensity.
Figure 4:
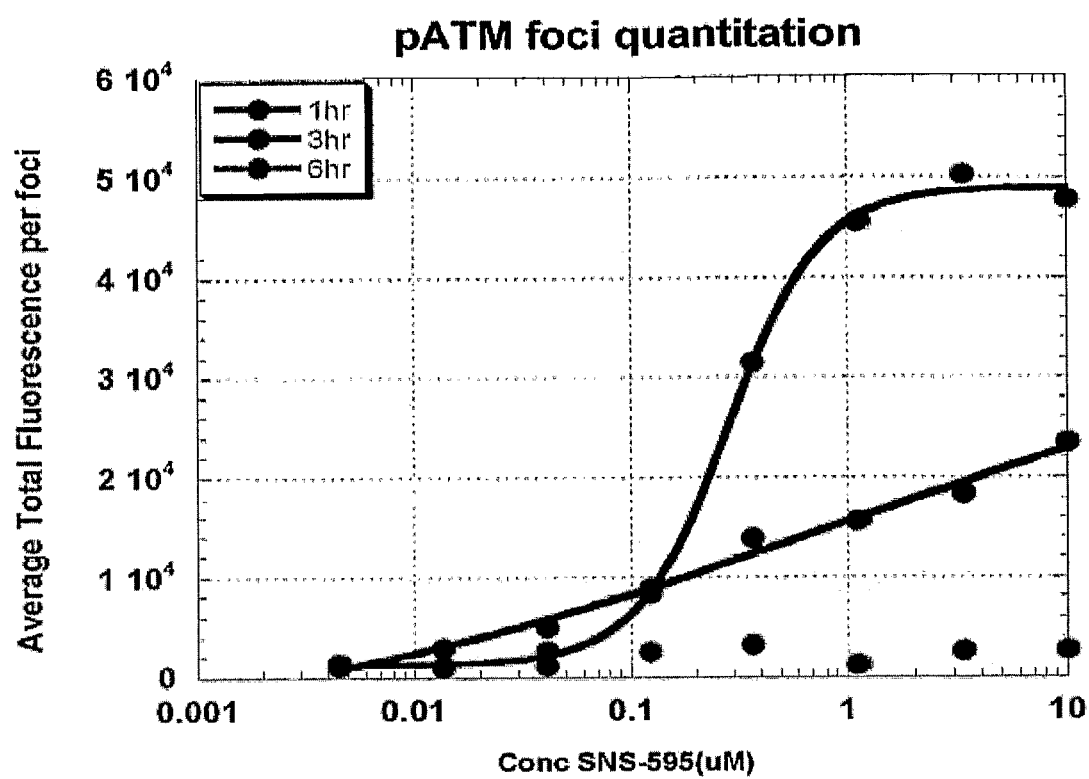
FIG. 4 illustrates dependence of foci formation on dose and time.
Figure 5:
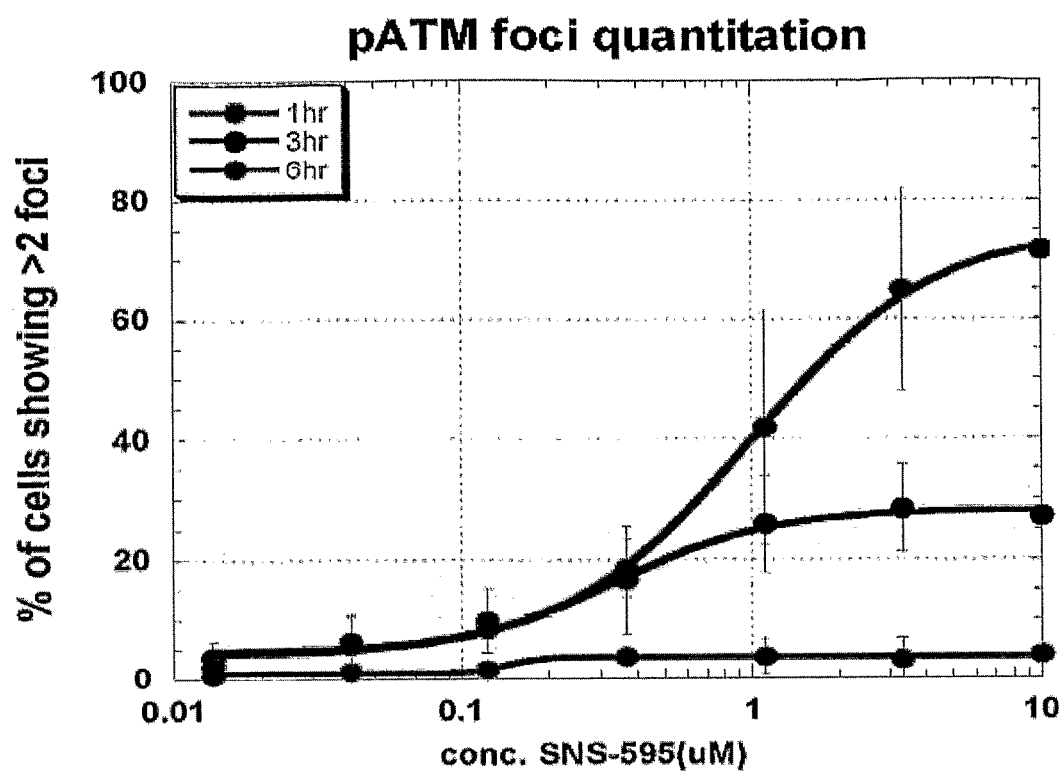
FIG. 5 shows cells with more than 2 foci as a function of time and SNS-595 concentration.

FIGS. 3-5 illustrate dependence of foci formation on dose and time. Cells were then fixed and analyzed for phospho-ATM. Cellomics Arrayscan software was used to identify foci (FIG. 3, orange spots). Foci quantitation was carried out by measuring either foci fluorescent intensity (FIG. 4) or cells with more than 2 foci (FIG. 5) as a function of time and SNS-595 concentration.

Example 4

MTT Assay and Sensitization Treatments

Cells were plated at 4000 cells per well in a 96 well plate, incubated for 24 hours and then treated with compound for 72 hours. Cells were then incubated with 5% MTT for 1-2 hours and lysed. MTT was colorimetrically read at 570 nm and $EC_{50}$'s were determined using linear regression analysis.

Sensitization was carried out with various chemical treatments. Cells were pre-treated for 16 hours with chemical sensitizer before addition of drug (concentrations were as follows: caffeine, 2 mM, DNAPK inhibitor II (make), 10 uM, and wortmannin, 100 nM. Data is provided in Table 12. Sensitization was measured as the fold decrease in the $EC_{50}$ for cytotoxicity as measured by an MTT assay.

TABLE 12

DNA damage sensor dependence of SNS-595

| Compound | DSB Mechanism | ATRFLOX[1] | DNAPKcs(−/−)[2] | Caffeine[3] | Cell Line | G2 Arrest[4] | S-Lag[5] | Timing of apoptosis[6] |
|---|---|---|---|---|---|---|---|---|
| SNS-595 | Replication dependent | 1 | 10 | 0.5 | HCT-116 | + | + | 0.4 |

TABLE 12-continued

DNA damage sensor dependence of SNS-595

| Compound | DSB Mechanism | ATRFLOX[1] | DNAPKcs(−/−)[2] | Caffeine[3] | Cell Line | G2 Arrest[4] | S-Lag[5] | Timing of apoptosis[6] |
|---|---|---|---|---|---|---|---|---|
| Etoposide | Topoisomerase II | 1 | 7 | 8 | ATRFLOX[1] | + | + | 0.35 |
| Bleomycin | Chemical | 1 | 4 | 10 | DNAPKcs(−/−)[2] | + | + | 0.25 |
| Camptothecin | Topoisomerase I Replication dependent | 5 | 0.7 | 6 | Caffeine[3] | − | + | 0.25 |

[1]HCT-116 cells with 6 fold lower ATR levels.
[2]MO59J (DNAPKcs(−/−)) vs MO59K (DNAPKcs(+/+)).
[3]HCT-116 cells treated with 2 mM caffeine to disrupt both ATM and ATR kinase activities.
[4]FACS analysis, asynchronous cell population.
[5]FACS analysis, synchronous cell population.
[6]Fraction of cell cycle to achieve 50% maximal caspase-3 activation if dosed at 30 fold above the EC50 for cytotoxicity.

The data indicates that SNS-595 displays a unique PIKK dependence. While both ATM/ATR and DNAPK are activated following treatment with SNS-595, only DNAPK is required for DNA repair and cells are sensitized to SNS-595 only when DNAPKcs activity is diminished. ATM/ATR mediates a G2-checkpoint arrest. Loss of the G2-checkpoint does not sensitize cells to SNS-595. In contrast to SNS-595, all other DSB-inducing agents tested utilize ATM/ATR for repair, and display sensitization when either ATM or DNAPK activities are inhibited.

Example 5

Repair of DNA Damage in the Absence of DNA-Damage Sensing Kinases ATM and ATR

Figure 6:
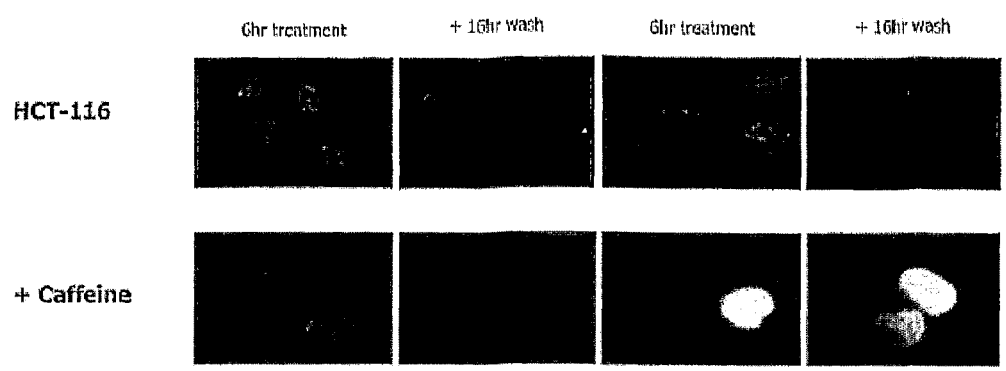
FIG. 6, illustrates DNA damage induced by SNS-595 and etoposide in the presence and absence of caffeine, which is an inhibitor of ATM and ATR.

HCT-116 cells were treated with 10 mM SNS-595 or 10 mM etoposide for 6 h with or without 2 mM caffeine. Compound was then removed and cells were allowed to recover for 16 hours. Cells were analyzed for gH2AX foci before and after drug washout. As seen in FIG. 6, DNA damage induced by SNS-595 is readily repaired in the absence of ATM and ATR. In contrast, other drugs, (e.g. Etoposide), utilize ATM and ATR for DNA repair. Caffeine treatment inhibits the activities of ATM and ATR, leading to defects in homologous recombination, nucleotide excision repair, and mismatch repair.

Example 6

Repair of DNA Damage in the Absence of DNA-Damage Sensing Kinase DNA-PK

M059K (wt) and M059J (DNAPKcs(−/−)) cells were treated with 10 mM SNS-595 or 10 mM etoposide for 6 hours. Compound was then removed and cells were allowed to recover for 16 hours. Cells were analyzed for gH2AX foci before and after drug washout. As seen in FIG. 7, SNS-595 damage is not effectively repaired in the absence of DNA-PK. By comparison, damage induced by other drugs (e.g. Etoposide), is readily repaired.

Example 7

Combination Studies with SNS-595

Cell lines and Cell Culture: HCT116 and NCI-H460 cell lines were obtained from ATCC. SKOV3(p53−/−) and SKOV3(p53+/+) were obtained from the lab of Dr. George Stark of the Lerner Institute of the Cleveland Clinic. All cell lines were cultured in RPMI media supplemented with 10% FBS 1% Sodium Bicarbonate solution and 1% Antibiotic Solution (Cellgro).

MTT assay: Cells were plated at 4000 cells per well (except SKOV3 (p53−/−) which were plated at 8000 cells per well) in a 96 well plate, incubated for 24 hours and then treated with compound. Compound treatment lasted 72 hours. Cells were then incubated with 5% MTT for 1-2 hours, and lysed. MTT was colorimetrically read at 570 nm. The fraction of dead cells was determined by the following formula:

Fraction of Dead cells=1−[Abs of sample well−Avg (Abs of no cell control)]/[Avg(Abs of DMSO only control)−Avg(abs of no cell control)]

Scheduling studies: When compounds were dosed with a schedule that included a washout, cells were washed with 100 µl of fresh warm media for 30 minutes, followed by another wash after 90 minutes.

Statistical Analysis: The data (Fraction of Dead cells) was analyzed using Calculsyn.V2 (Biosoft) and is herein represented as the value of the Combination Index at Fraction affected (Fa)=0.5. All data is shown with error bars indicating the 95% confidence intervals of the mean value.

A combination is said to be additive if it yields a Combination Index of 0.85-1.2. A combination is said to be synergistic if it yields a Combination Index less than 0.85 and a combination is said to be antagonistic if it yields a Combination Index of more than 1.2. See FIGS. 8-10.

As seen in FIGS. 8a-8d, SNS-595 dosed simultaneously with various cytotoxics in HCT116 colon carcinoma cell line (8a, 8b and 8c) and H460 lung cancer cell line 8(d) showed significantly synergistic or at least additive combination indices. As seen in FIG. 9, SNS-595 dosed simultaneously with a selection of DNA damaging agents and antimetabolites showed no significant change in the combination index between SKOV3 ovarian cancer cell line with or without p53 expression.

As seen in FIGS. 10a-10d, SNS-595 might have been antagonistic when SNS-595 was co-dosed, or dosed with 24 hours delay, with docetaxel (see, FIGS. 10a and 10c) and gemcitabin (see, FIGS. 10b and 10d) in HCT116 colon carcinoma cells. Antagonism might have been reduced by dosing SNS-595 first (see, FIGS. 10c and 10d, co-dose and 24 hrs) versus dosing the other agents first (see, FIGS. 10a and 10b, co-dose and 24 hrs). Additivity or possibly synergy was achieved when cells were treated with the first agent, washed and then treated with the second agent (see, FIGS. 10a-d, 2 hr wash and 24 hr wash).

Example 8

MTT Cell Viability Assay-Leukemia Cells

The following cell lines were used in this assay: HL-60 (promyelocytic leukemia); Jurkat (T cell leukemia); CCRF-CEM (lymphoblastic leukemia); CEM/C2 (camptothecan resistant derivative of CCRF-CEM).

Cells were seeded in 96 wells plates at 3000 cells per well and incubated for 16 hours. Compound dilutions were performed in DMSO from 10 mM with 3 fold dilutions. Titrations were diluted 1:100 in media to achieve final compound concentrations. The 96 well plates were aspirated and compound dilutions in media were added (100 ml/well). MTT analysis was carried out after 72 hours of incubation at 37° C. Briefly, 20 ml of MTT solution was added to each well. Cells were incubated at 37° C. for 1-2 hours. Cells were lysed with the addition of 100 ml/well cell lysis buffer and MTT was solubilized overnight at 37° C. Plates were read on a spectromax machine with an absorbance measurement at 570 nM. $IC_{50}$'s were calculated (data provided in Table 13) using regression analysis within GraphPad Prism. As provided in Table 13, SNS-595 shows potent anti-proliferative activity against hematologic cell lines tested.

TABLE 13

$IC_{50}$ data for various cell lines

| Cell Line | $IC_{50}$ ng/mL | | | |
|---|---|---|---|---|
| | SNS-595 | Etoposide | Doxorubicin | Irinotecan |
| HL-60 | 53 | 136 | 24 | 905 |
| Jurkat | 23 | nd | Nd | nd |
| CCRF-CEM | 18 | nd | 3 | 479 |
| CEM/C2 | 10 | nd | 17 | 44400 |

Example 9

Xenograft Models

LM3-Jck human malignant lymphoma tumor lobes (2-3 mm square) were transplanted subcutaneously into nude mice. Tumors were allowed to grow to approximately 7-14 mm in diameter. Mice were pair-matched into no treatment, irinotecan (100 mg/kg, IV, q4d×3), doxorubicin (12 mg/kg, IV, Single shot), etoposide (12 mg/kg, IV, q1d×5), and SNS-595 (25 and 20 mg/kg, IV, q7d×5) treatment groups. Acceptable toxicity was defined as a mean group weight loss of 30% or less and not more than one toxic death among 6 treated animals. Anti-tumor activities of the drugs were assessed 21 days after the start of administration.

CCRF-CEM acute lymphoblastic leukemia tumor lobes of 2-3 mm square were transplanted subcutaneously into nude mice. Tumors were allowed to grow to approximately 8-20 mm in diameter. Mice were pair-matched into no treatment, irinotecan (100 mg/kg, IV, q4d×3), doxorubicin (12 mg/kg, IV, q7d×3), etoposide (12 mg/kg, IV, q1d×5), and SNS-595 (25 and 20 mg/kg, IV, q7d×5) treatment groups. Acceptable toxicity was defined as a mean group weight loss of 30% or less and not more than one toxic death among 6 treated animals. Anti-tumor activities of the drugs were assessed 20 or 21 days after the start of administration. Table 14 provides data for tumor inhibition (TI) and survival rate in the CCRF-CEM and LM3-Jck xenograft models.

TABLE 14

Comparative anti-tumor activity of SNS-595 and other anti-cancer drugs

| Treatment | Dose (mg/kg) | CCRF-CEM | | LM3-JcK | |
|---|---|---|---|---|---|
| | | IR (%) | Survival Ratio | IR (%) | Survival Ratio |
| SNS-595 q7d X3, IV | 20 | —* | — | 98.9* | 6/6 |
| | 25 | 98.1* | 6/6* | 98.5* | 6/6 |
| Irinotecan q4d x3, IV | 100 | 99.7* | 5/6 | 97.7* | 6/6 |
| Doxorubicin q7d X3, IV | 12 | 50.3* | 6/6 | 57.2* | 6/6 |
| Etoposide qd X 5, IV | 12 | 28.3 | 6/6 | 3.0 | 6/6 |

As seen from the data in Table 14, SNS-595 administered at 20 and 25 mg/kg shows strong antitumor activity with complete tumor regressions against LM-3 Jck malignant lymphoma. Tumor inhibition rate (IR) of SNS-595 was similar to that of irinotecan and superior to etoposide and doxorubicin in both the CCRF-CEM and LM3-Jck xenograft models.

Example 10

Bone Marrow/Cytology Assay

Female CD-1 mice were administered 5, 10, 15, or 20 mg/kg SNS-595 intravenously on Day 0 and Day 4. Blood was drawn on days 6, 8, and 12 post initial injection for hematological analysis. Femurs were extracted on day 6 fixed in Streck and H&E stained prior to bone marrow cellularity analysis. Two days after the second administration of SNS-595, bone marrow isolated from femurs showed a dose-dependent reduction in cellularity. At 20 mg/kg, cellularity was reduced to 7.5%, while circulating neutrophils were reduced from a pre-dose level of 1244±55 cells/mL to a nadir of 51±24 cells/mL blood on day 8. Absolute neutrophil counts subsequently rebounded and soon returned to normal levels. Total WBCs also reached a nadir on day 8, but returned to normal levels. Dose dependent decrease in the hematopoietic bone marrow cellularity is shown in FIG. 14. The FIG. shows cellularity in bone marrow 6 days post initial injection of SNS-595 at various doses.

FIG. 15 shows neutrophil counts from blood samples on days 4, 6, 8, and 12 post initial injection. As seen in FIG. 16, all SNS-595 dose groups demonstrated a significant decrease in peripheral neutrophils by day 8. As seen in FIG. 17, animals receiving 20 mg/kg injections of SNS-595 had less than 50 cells/ml on day 8.

FIG. 18 shows that there is a minor platelet response at day 8 to SNS-595 injection. FIG. 19 shows percent change in body weight at various times after administering SNS-595. FIG. 20 shows bone marrow rebound at day 12 post injection of 20 mg/kg SNS-595.

Example 11

Clinical Trial Data of SNS-595 in Patients with Hematologic Malignancies

SNS-595 was administered to patients with advanced or refractory acute leukemias as a slow IV push. Diagnoses included AML (19 patients) and ALL (2 patients). All patients had disease refractory to or relapsed from prior therapy (median 3 prior regimens (range 1-6)).

A total of 21 patients (9 female and 12 male; median age=64 yrs, range 21-80) were treated in five cohorts using two schedules. In the first schedule (A), a weekly dose of SNS-595 was administered for three weeks followed by 7 days off (qwk×3). In the second schedule (B), a dose of SNS-595 was administered twice a week for two weeks (biwk×2). The cycle duration, including days off, was 28 days for both schedules. Schedule A had a total of 3 doses per cycle, and schedule B had a total of 4 doses per cycle. Additional cycles were permitted if patients achieved stable disease or better. The starting dose was 18 mg/m² on schedule A and 9 mg/m² on schedule B, and dosage was escalated by cohort. Cohorts of 3-6 patients were accrued to doses using a modified Fibonacci sequence.

Pharmacokinetic analyses for SNS-595 were performed on plasma samples collected during cycle 1. Table 15 provides certain pharmacokinetic parameters derived from the study.

TABLE 15

Pharmacokinetic Parameters

| Dose (mg/m²) | Schedule | T ½ hr | $AUC_{inf}$ µg · hr/ml | $Cl_{obs}$ L/hrm² | $V_{ssobs}$ L/m² |
|---|---|---|---|---|---|
| 18 | qwk x3 | 24 ± 4 | 8.0 ± 1.4 | 2.3 ± 0.4 | 72 ± 21 |
| 27 | qwk x3 | 22 ± 10 | 17.8 ± 5 | 1.6 ± 0.4 | 47 ± 21 |
| 9* | biwk x2 | 24 ± 5 | 4.3 ± 1.3 | 2.3 ± 0.7 | 65 ± 2 |
| 13.5* | biwk x2 | 21 ± 7 | 5.9 ± 2.9 | 2.5 ± 1.2 | 61 ± 6 |

*Similar PK after Days 4, 8, and 11 administration.

Plasma SNS-595 concentrations were determined using a validated LC-MS/MS assay. Plasma exposures at the first two dose levels for each schedule increased linearly, resulting in AUCs of 4.3-17.8 ughr/mL for 9-27 mg/m² doses. CL, Vss and terminal half-lives were similar to those in solid tumor patients, and averaged ~2 L/hr/m², 58 L/m², and 23 hr, respectively. Six patients distributed across all dosing groups shown in Table 15 experienced greater than 50% reductions in peripheral blasts following cycle 1.

No dose limiting toxicities (DLTs) have been observed up to 27 mg/m² on the qwk×3 schedule or up to 13.5 mg/m² on the biwk×2 schedule. Non-dose limiting toxicities included nausea/vomiting, diarrhea, and mucositis. Grade 4 neutropenic fever was observed in only one patient.

Other patient cohorts were administered dosages of 38 mg/m² and 50 mg/m², respectively, according to Schedule A (qwk×3). Still other patient cohorts were administered dosages of 19 mg/m² and 25 mg/m², respectively, according to Schedule B (biwk×2). Safety data are shown in Table 16.

TABLE 16

Serious Adverse Events (SAE) Possibly Related to Study Drug

| Event Name 1 patient for each of the following | CTCAE v3.0 Grade | |
|---|---|---|
| | qwk x3 | biwk x2 |
| Pneumonia with Neutropenia | Grade 3 | not observed |
| Infection with Neutropenia | Grade 3 | not observed |
| Neutropenic Fevers | not observed | Grade 4 |
| Infection | not observed | Grade 3 |

Useful dosing schedules for treatment of hematologic malignancies can include from about 50 mg/m² to about 80 mg/m² administered once a week for three weeks, Another dose finding use in treatment of hematologic malignancies is about 55 mg/m² to about 75 mg/m² administered once a week for three weeks. Other doses doses finding use in treatment of hematologic malignancies include 60, 65, 70 or 75 mg/m² administered once a week for three weeks.

Other dosing schedules useful for treatment of patients with hematologic malignacies can include about 25 mg/m² to about 50 mg/m² administered twice a week for two weeks. Another dose finding use in treatment of hematologic malignancies is about 30 mg/m² to about 45 mg/m² administered twice a week for two weeks. Other doses finding use in treatment of hematologic malignancies include 30, 35, 40, or 45 mg/m² administered twice a week for two weeks.

The embodiments of the invention described above are intended to be merely exemplary, and those skilled in the art will recognize, or will be able to ascertain using no more than routine experimentation, numerous equivalents of specific compounds, materials, and procedures. All such equivalents are considered to be within the scope of the invention and are encompassed by the appended claims.

What is claimed is:

1. A method of treating acute myelogenous leukemia comprising administering a dose of 50 to 90 mg/m² of an enantiomerically pure (+)-1,4-dihydro-7-[(3S,4S)-3-methoxy-4-(methylamino)-1-pyrrolidinyl]-4-oxo-1-(2-thiazolyl)-1,8-naphthyridine-3-carboxylic acid to a human with acute myelogenous leukemia.

2. The method of claim 1, wherein the acute myelogenous leukemia is a myeloblastic leukemia or promyelocytic leukemia.

3. The method of claim 1, wherein the leukemia is relapsed, refractory or resistant to therapy selected from surgery, chemotherapy, radiation therapy, hormonal therapy, biological therapy, immunotherapy, blood transfusions, and combinations thereof.

4. The method of claim 1, wherein the dose is from 50 mg/m² to 80 mg/m² administered once a week for at least two weeks.

5. The method of claim 4, wherein the dose is from 55 mg/m² to 75 mg/m².

6. The method of claim 5, wherein the dose is 60 mg/m².

7. The method of claim 5, wherein the dose is 65 mg/m².

8. The method of claim 5, wherein the dose is 70 mg/m².

9. The method of claim 5, wherein the dose is 75 mg/m².

10. The method of claim 1, wherein the dose is administered once a week for three weeks.

11. The method of claim 1, wherein the dose is administered twice a week.

12. The method of claim 11, wherein the dose is from 80 mg/m² to 90 mg/m².

13. The method of claim 11, wherein the dose is 65 mg/m² to 75 mg/m².

14. The method of claim 11, wherein the dose is administered for two weeks.

15. The method of claim 1, wherein the enantiomerically pure (+)-1,4-dihydro-7-[(3S,4S)-3-methoxy-4-(methylamino)-1-pyrrolidinyl]-4-oxo-1-(2-thiazolyl)-1,8-naphthyridine-3-carboxylic acid is administered as an IV injection.

16. The method of claim 1, wherein the dose is administered in an IV push of 10-15 minutes duration.

17. A method of treating acute myelogenous leukemia comprising administering a dose of 85 to 95 mg/m² of an enantiomerically pure (+)-1,4-dihydro-7-[(3S,4S)-3-methoxy-4-(methylamino)-1-pyrrolidinyl]-4-oxo-1-(2-thiazolyl)-1,8-naphthyridine-3-carboxylic acid to a human with acute myelogenous leukemia.

18. A method of treating acute myelogenous leukemia comprising administering a dose of 90 to 100 mg/m$^2$ of an enantiomerically pure (+)-1,4-dihydro-7-[(3S,4S)-3-methoxy-4-(methylamino)-1-pyrrolidinyl]-4-oxo-1-(2-thiazolyl)-1,8-naphthyridine-3-carboxylic acid to a human with acute myelogenous leukemia.

19. The method of claim 17 or 18, wherein the acute myelogenous leukemia is a myeloblastic leukemia or promyelocytic leukemia.

20. The method of claim 17 or 18, wherein the leukemia is relapsed, refractory or resistant to therapy selected from surgery, chemotherapy, radiation therapy, hormonal therapy, biological therapy, immunotherapy, blood transfusions, and combinations thereof.

21. The method of claim 17 or 18, wherein the dose is administered once a week for three weeks.

22. The method of claim 17 or 18, wherein the dose is administered twice a week.

23. The method of claim 17 or 18, wherein the enantiomerically pure (+)-1,4-dihydro-7-[(3S,4S)-3-methoxy-4-(methylamino)-1-pyrrolidinyl]-4-oxo-1-(2-thiazolyl)-1,8-naphthyridine-3-carboxylic acid is administered as an IV injection.

24. The method of claim 17 or 18, wherein the dose is administered in an IV push of 10-15 minutes duration.

* * * * *

UNITED STATES PATENT AND TRADEMARK OFFICE
CERTIFICATE OF CORRECTION

Page 1 of 1

PATENT NO.        : 8,580,814 B2
APPLICATION NO.   : 11/991349
DATED             : November 12, 2013
INVENTOR(S)       : Adelman et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 767 days.

Signed and Sealed this
Seventh Day of July, 2015

Michelle K. Lee
*Director of the United States Patent and Trademark Office*